US012611549B2

(12) United States Patent
    Cohen et al.

(10) Patent No.: US 12,611,549 B2
(45) Date of Patent: Apr. 28, 2026

(54) SYSTEMS AND METHODS FOR MODULATED MULTI-SPECTRAL MAGNETIC STIMULATION

(71) Applicants: Round River Research Corporation, Edina, MN (US); Daniel E. Cohen, Eden Prairie, MN (US); Jennifer Palmquist, Eden Prairie, MN (US); David Cohen, Deephaven, MN (US); Bruce C. Johnson, Saint Paul, MN (US); Ellen Cohen, Edina, MN (US); Dan Alan Preston, Bainbridge Island, WA (US)

(72) Inventors: Daniel E. Cohen, Eden Prairie, MN (US); Jennifer Palmquist, Eden Prairie, MN (US); David Cohen, Deephaven, MN (US); Bruce C. Johnson, Saint Paul, MN (US); Ellen Cohen, Edina, MN (US); Dan Alan Preston, Bainbridge Island, WA (US)

( * ) Notice: Subject to any disclaimer, the term of this patent is extended or adjusted under 35 U.S.C. 154(b) by 853 days.

(21) Appl. No.: 17/290,748

(22) PCT Filed: Oct. 30, 2019

(86) PCT No.: PCT/US2019/058970
    § 371 (c)(1),
    (2) Date: Apr. 30, 2021

(87) PCT Pub. No.: WO2020/092653
    PCT Pub. Date: May 7, 2020

(65) Prior Publication Data
    US 2022/0001191 A1      Jan. 6, 2022

Related U.S. Application Data

(60) Provisional application No. 62/900,343, filed on Sep. 13, 2019, provisional application No. 62/752,507, filed on Oct. 30, 2018.

(51) Int. Cl.
    *A61N 2/00*      (2006.01)
    *A61N 2/12*      (2006.01)
    (Continued)

(52) U.S. Cl.
    CPC ............... *A61N 2/12* (2013.01); *A61N 2/006* (2013.01); *A61M 2205/3303* (2013.01);
    (Continued)

(58) Field of Classification Search
    None
    See application file for complete search history.

(56) References Cited

U.S. PATENT DOCUMENTS

| | | | |
|---|---|---|---|
| 5,085,627 A | 2/1992 | Fedorinov | |
| 5,442,710 A | 8/1995 | Komatsu | |
| (Continued) | | | |

FOREIGN PATENT DOCUMENTS

| | | | |
|---|---|---|---|
| JP | S56156164 A | 12/1981 | |
| JP | H02055066 A | 1/1993 | |
| (Continued) | | | |

OTHER PUBLICATIONS

Extended European Search Report of European App. No. 19880603.6PCT/US2019/058970 mailed on Jul. 13, 2022.
(Continued)

*Primary Examiner* — Carrie R Dorna
(74) *Attorney, Agent, or Firm* — Polsinelli PC

(57) ABSTRACT

It is well understood in the medical industry that medical disorders can manifest as serious problems for the affected subjects, their families, and society. Today, psychiatrists, neurologists and other physicians treat these disorders with a variety of medications, many of which have significant negative side effects. The teachings provided herein are directed to a novel system and methods for treating certain neurological, psychological, psychiatric and medical disor-
(Continued)

ders by delivering a "magnetic stimulation" to a subject's neural and perineural system using either a static or electromagnetic field to generate a modulated variable power multi-spectral magnetic stimulation on three axis; the modulated stimulation using methods that have predictable, controlled, modifiable, and repeatable characteristics.

17 Claims, 46 Drawing Sheets

(51) Int. Cl.

| | |
|---|---|
| *G16H 10/60* | (2018.01) |
| *G16H 40/67* | (2018.01) |
| *H04W 4/80* | (2018.01) |
| *H04W 84/12* | (2009.01) |

(52) U.S. Cl.
CPC ............. *G16H 10/60* (2018.01); *G16H 40/67* (2018.01); *H04W 4/80* (2018.02); *H04W 84/12* (2013.01)

(56) References Cited

U.S. PATENT DOCUMENTS

| | | | | |
|---|---|---|---|---|
| 5,632,720 | A | 5/1997 | Kleitz | |
| 5,685,514 | A | 11/1997 | Carnahan | |
| 6,001,055 | A | 12/1999 | Souder | |
| 8,936,542 | B1 * | 1/2015 | Bates .................... | A61H 7/007 |
| | | | | 600/9 |
| 2002/0111614 | A1 * | 8/2002 | Werny .................... | A61N 2/12 |
| | | | | 606/33 |
| 2008/0214968 | A1 * | 9/2008 | Milne ................ | A61H 23/0263 |
| | | | | 601/67 |
| 2011/0021898 | A1 * | 1/2011 | Wei ........................ | G16H 40/60 |
| | | | | 600/365 |
| 2011/0054240 | A1 | 3/2011 | Bender | |
| 2011/0277246 | A1 | 11/2011 | Willingham | |
| 2012/0051579 | A1 | 3/2012 | Cohen | |
| 2013/0238049 | A1 * | 9/2013 | Simon ................ | A61N 1/36034 |
| | | | | 607/42 |
| 2014/0010387 | A1 | 1/2014 | Cohen | |
| 2014/0235925 | A1 * | 8/2014 | Paz .......................... | A01G 7/00 |
| | | | | 47/1.01 R |
| 2014/0371515 | A1 | 12/2014 | John | |
| 2017/0113056 | A1 * | 4/2017 | Stocco ................. | A61N 1/0476 |

FOREIGN PATENT DOCUMENTS

| | | |
|---|---|---|
| JP | H11285539 | 10/1999 |
| JP | H11285539 A | 10/1999 |
| JP | 2018115414 A | 7/2018 |
| WO | 2013173640 | 11/2013 |
| WO | 2017193078 A1 | 11/2017 |

OTHER PUBLICATIONS

International Search Report and Written Opinion of PCT/US2016/058292 mailed on Jan. 3, 2017.
International Search Report and Written Opinion for PCT/US2019/058970, dated Jan. 21, 2020, 8 pages.
Report of Decision to Grant Issued Oct. 8, 2024 in JP 2021-549729, Japan.
Jul. 13, 2022 Extended European Search Report & Opinion and Feb. 9, 2023 Response in EU 19880603.6, Europe.
Communication Pursuant to Article 94(3) in EU 19880603.6 on Jul. 30, 2024, Europe.
Examination Report issued May 22, 2024 in AU 2019372125, Australia.
Report of Office Action received on Jul. 10, 2024 in MX/a/2021/004903 and Response to Office Action, Mexico.
First Examination Report issued Dec. 26, 2022 and Aug. 22, 2023 Response in IN 202117023648, India.

* cited by examiner

500

600

2600

2700

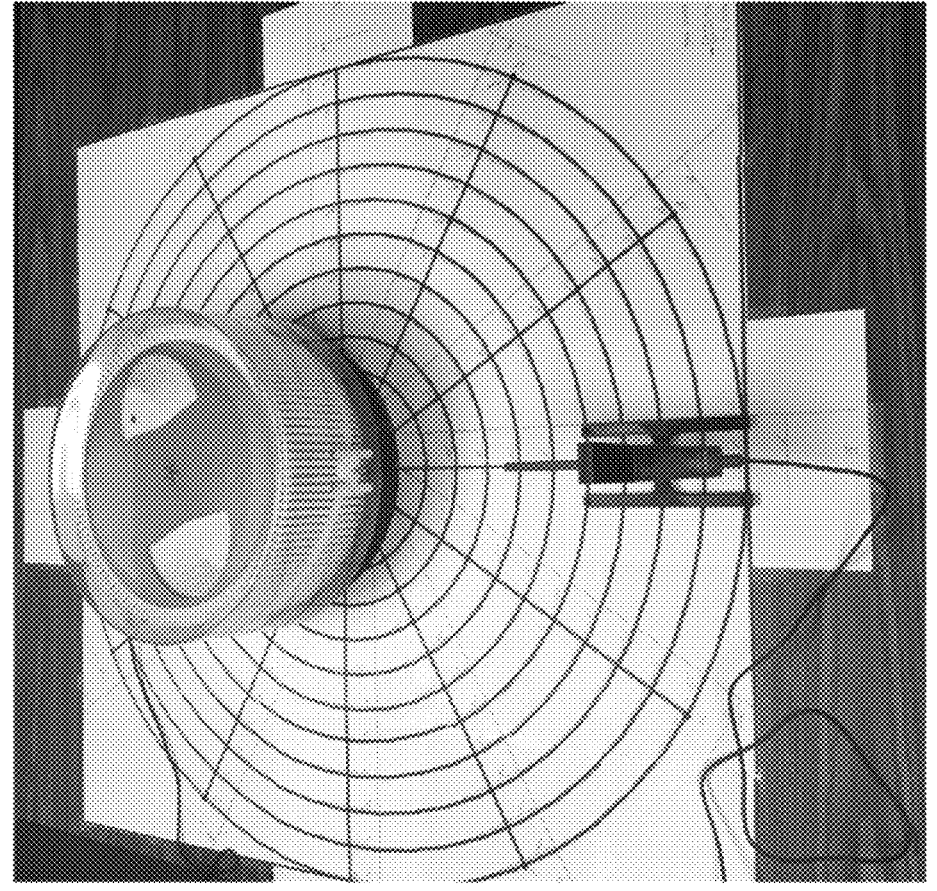
FIG. 28
2800

2900

2902
2903
2901

2902
2901
2903

Figure 30:
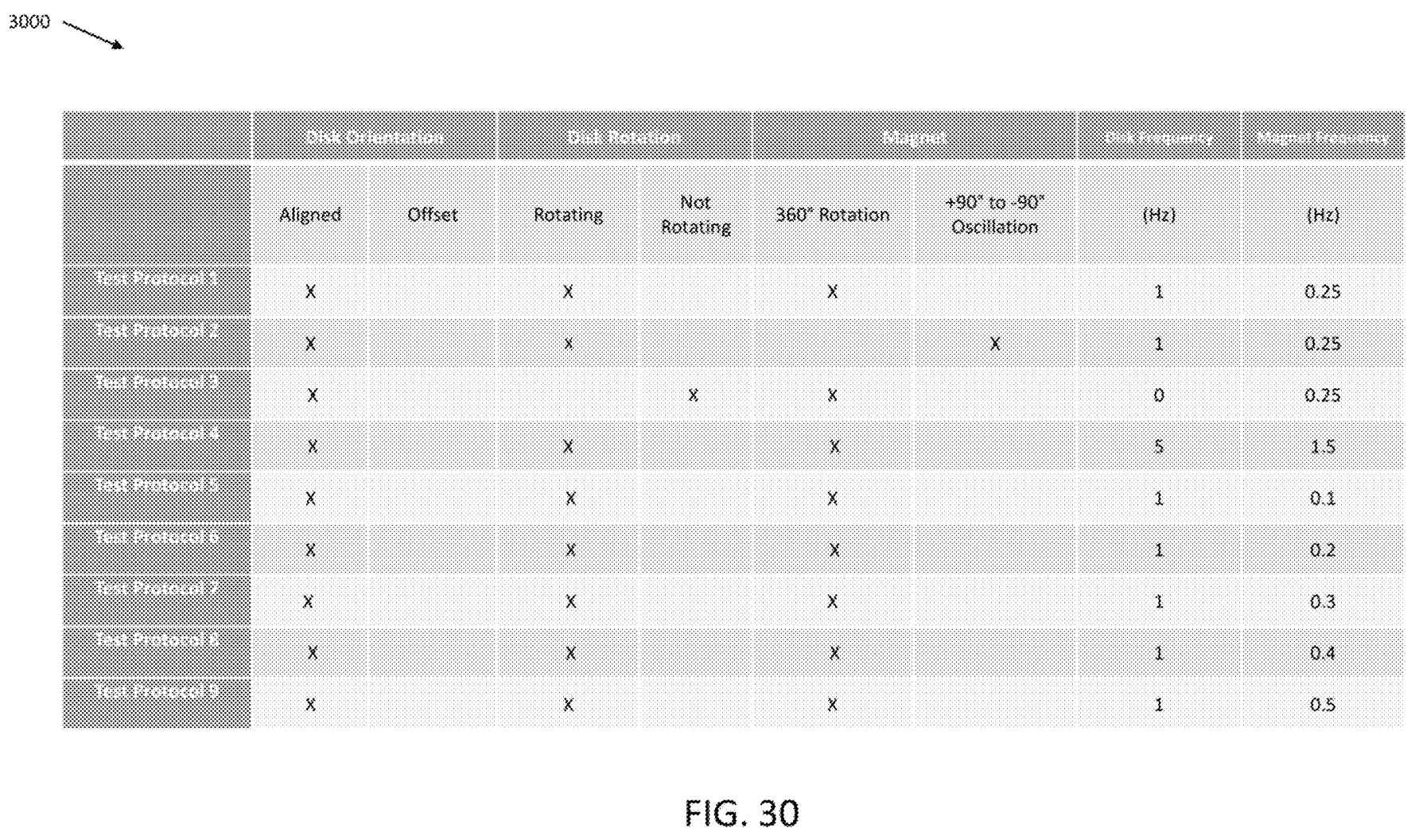

| | Aligned | Offset | Rotating | Not Rotating | 360° Rotation | +90° to -90° Oscillation | (Hz) | (Hz) |
|---|---|---|---|---|---|---|---|---|
| | X | | X | | X | | 1 | 0.25 |
| | X | | X | | | X | 1 | 0.25 |
| | X | | | X | X | | 0 | 0.25 |
| | X | | X | | X | | 5 | 1.5 |
| | X | | X | | X | | 1 | 0.1 |
| | X | | X | | X | | 1 | 0.2 |
| | X | | X | | X | | 1 | 0.3 |
| | X | | X | | X | | 1 | 0.4 |
| | X | | X | | X | | 1 | 0.5 |

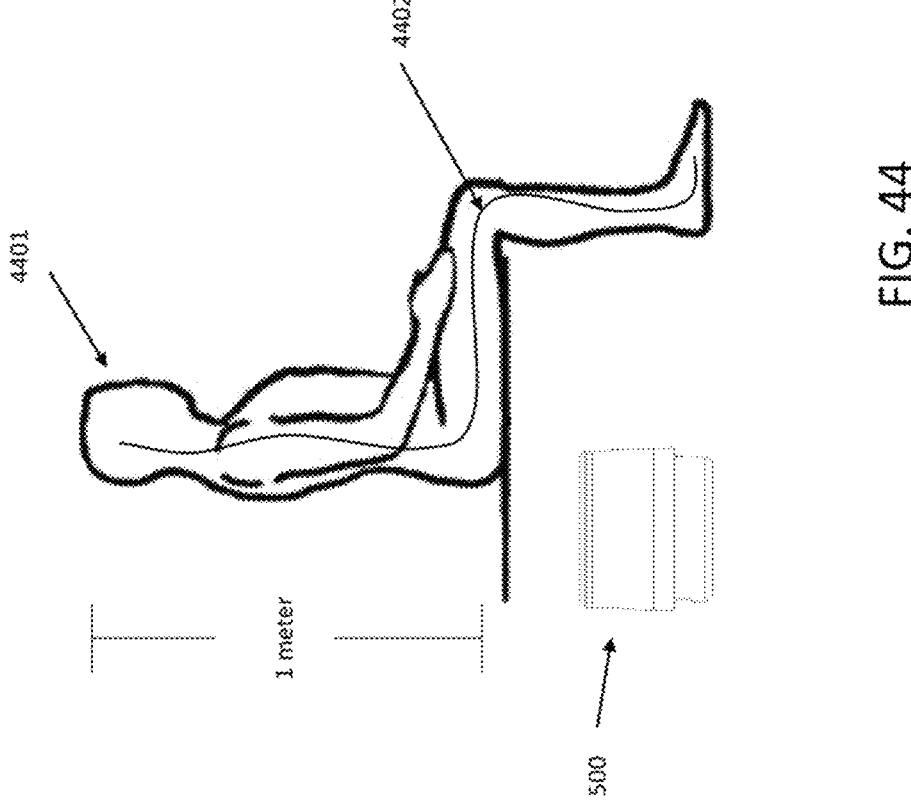
FIG. 44

SYSTEMS AND METHODS FOR MODULATED MULTI-SPECTRAL MAGNETIC STIMULATION

RELATED APPLICATIONS

This application claims priority to U.S. Provisional Patent Application No. 62/752,507, filed on Oct. 30, 2018, and U.S. Provisional Patent Application No. 62/900,343, filed on Sep. 13, 2019, the contents of which are incorporated by reference herein in their entirety.

COPYRIGHT NOTICE

TECHNICAL FIELD OF THE INVENTION

This invention relates generally to novel systems and methods for treating certain neurological, psychological, psychiatric and medical disorders by delivering a "magnetic stimulation" to a subject's neural and perineural system using either a static or electro-magnetic field to generate a variably modulated multi-spectral magnetic stimulation on three axis; the modulated stimulation using methods that have predictable, controlled, modifiable, and repeatable characteristics.

BACKGROUND

It is well understood in the medical industry that medical disorders can manifest as serious problems for the affected subjects, their families, and society. Today, psychiatrists, neurologists and other physicians treat these disorders with a variety of medications, many of which have significant negative side effects. The teachings provided herein are directed to a novel system and methods for treating certain neurological, psychological, psychiatric and medical disorders by delivering a "magnetic stimulation" to a subject's neural and perineural system using a magnetic field to generate a modulated variable power, multi-spectral magnetic multi-axis stimulation; the stimulation effect is done using methods that have predictable, controlled, modifiable, and repeatable characteristics. The stimulation generated by these fields pass through clothing, tissue and bone to reach otherwise inaccessible areas, and it operates without stimulating pain fibers at the skin surface.

Following Luigi Galvani's discovery in the 1700s that the application of electrical current to nerves could elicit muscular contractions, electrical stimulation led to a rapid advancement in our understanding of the function and organization of the nervous system. The modern use of electrical stimulation, targeting deep cerebral structures for management of neurological disorders, did not occur until the 1950s, when Robert Heath implanted electrodes in patients with chronic pain.

Alternatively, according to Faraday's law of induction, time-varying magnetic fields generated by alternating current through a coil can induce extracellular electrical fields and neuronal activation. In 1896, d'Arsonval et al. developed a large alternating power source that when applied to a coil external to the skull, activated neurons within the brain, providing empirical evidence to support the notion of the stimulation of nervous tissue by electromagnetic induction. However, this technology was not widely utilized until the 1980s when electronic and power source advancements led to the development of a reliable system, termed transcranial magnetic stimulation (TMS). In seminal studies, Barker et al. were able to generate a muscle twitch response of the contralateral limbs by TMS activation of cortex. Since the development of TMS, many scientists have pioneered its use as a non-invasive means of modulating brain activity for either neuroscientific investigations or as a therapeutic modality.

In a discussion of related art, the majority of systems marketed today focus on magnetic stimulators used for transcranial magnetic stimulation. Fifteen years after its introduction by Anthony Barker, transcranial magnetic stimulation (TMS) appears to be 'coming of age' in cognitive neuroscience and promises to reshape the way we investigate brain—behavior relations. Among the many methods now available for imaging the activity of the human brain, magnetic stimulation is currently one technique that allows interaction with brain function. As illustrated by several experiments over the past couple of years, this property of TMS allows us to investigate the relationship between focal cortical activity and behavior, to trace the timing at which activity in a particular cortical region contributes to a given task, and to map the functional connectivity between brain regions.

TMS of the nervous system have been invaluable for investigating various functions of the nervous system. Despite this success, these technologies have technical and practical limitations impeding their full potential. New studies have been conducted suggesting that peripheral axons are excited by the spatial gradients of the induced electric field in both peripheral and central neurons. It was found the amplitude of the stimulation required for an action potential generation was inversely proportional to the square of the diameter of the stimulated compartment. Due to the importance of the fiber's diameter, magnetic stimulation of neurons depolarized the soma followed by initiation of an action potential in the initial segment of the axon. Passive dendrites affect this process primarily as current sinks, not sources. The simulations predict that neurons with low current threshold are more susceptible to magnetic stimulation and may be relevant for the design of multi-intensity TMS protocols and may aid the interpretation of results of TMS of the CNS.

It is also well documented in the art an emerging and complementary approach to remotely control biological processes based on magnetic stimulation. So far, the effect of magnetic fields on cellular response has been investigated in different contexts. A first instance is the field of 'magnetosensation', i.e. the ability to detect magnetic fields. A second area of research focuses on the influence of magnetic fields on biological processes in general. Here, usually strong magnetic fields (>1 T) have been applied to show that biopolymers with high diamagnetic anisotropy can respond to the external magnetic field.

With respect now to the magnetic influence in cellular processes and the remote activation of cellular processes, it is now better understood and rapidly becoming an important aspect of the fields of nanotechnology and bioengineering. New tools for stimulation including magnetic stimulation laid the ground for a new field, sometimes termed 'magnetogenetics'. Here, the recent advances in magnetogenetics highlight its potential for both fundamental and applied biomedical research.

The underlying and pre-eminent goal in neuroscience is to understand how the brain functions at the anatomical, physiological and molecular level. This aim has been greatly advanced by the development of tools for the stimulation and manipulation of neuronal activity. While these new approaches have provided unique insights into the circuitry that underlie complex behavioral responses, it has some limitations. Specifically, the necessity to deliver a stimulation to the cells of interest without requiring an invasive surgery lend well to the use of magnetism generally in the field of magnetogenetics by activating neurons with a magnetic stimulus as magnetic fields pass freely through organic tissue and could therefore activate any neuronal population no matter its anatomical location through an exploitation of the sensitivity of magnetoreceptors for this purpose.

It is generally accepted that certain mechanisms within the neural system used to facilitate the transmission of a stimulus generated from a static or modulated static magnetic field include ion channels in the nervous system. These channels refer to proteins allowing charged particles to cross membranes found in neurons and glia, where they are involved in maintaining the electrochemical gradients that allow neurons to produce action potentials and neurons and glia to release and recycle neurotransmitters.

Ion channels are pore-forming membrane proteins that allow ions to pass through the channel pore. Their functions include establishing a resting membrane potential, shaping action potentials and other electrical signals by gating the flow of ions across the cell membrane, controlling the flow of ions across secretory and epithelial cells, and regulating cell volume. Ion channels are present in the membranes of all excitable cells. Ion channels are one of the two classes of ionophoric proteins, the other being ion transporters.

Ion channels are located within the membrane of all excitable cells, and of many intracellular organelles. They are often described as narrow, water-filled tunnels that allow only ions of a certain size and/or charge to pass through; this characteristic is called selective permeability. In many ion channels, passage through the pore is governed by a "gate", which may be opened or closed in response to chemical, electrical or a magnetic force.

With the above aspects of the known art summarized regarding the field of magnetic stimulation, it is well known that magnetic stimulus impacts the human body from the brain to nano-particles of magnetic and paramagnetic materials; from the central nervous system comprising the neural and perineural systems; to the individual cells comprising the body all connected by one or more ion channels acting as mechanisms for the transport of magnetic stimulus. These are only now being understood; but it is with consensus they exist. To date the effects of magnetic stimulation directly on the brain have been primarily reached by clinical means through many years of clinical trials with little understanding of the mechanisms. What has not been discussed or documented in the art are systems and methods for stimulating the nervous system by delivering a "magnetic stimulation" to a subject's neural and perineural system using either a static or electromagnetic field to generate a modulated variable power multi-spectral magnetic stimulation on three axis; the modulated stimulation using methods that have predictable, controlled, modifiable, and repeatable characteristics.

SUMMARY OF THE INVENTION

Although the best understanding of the present invention will be had from a through reading of the specification and claims presented below, this summary is provided in order to acquaint the reader with some of the new and useful features of the present invention. Of course, this summary is not intended to be a complete litany of all of the features of the present invention, nor is it intended in any way to limit the breadth of the claims, which are presented at the end of the detailed description of this application.

The present invention provides among other things systems and methods for stimulating the nervous system by delivering a "magnetic stimulation" to a subject's neural and perineural system using either a static or electro-magnetic field to generate a modulated variable power multi-spectral magnetic stimulation on three axis; the modulated stimulation using methods that have predictable, controlled, modifiable, and repeatable characteristics.

Other features of the present invention will be apparent from the accompanying drawings and from the detailed description that follows.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112, ¶6. Thus, the use of the words "function," "means" or "step" in the Detailed Description or Description of the Drawings or claims is not intended to somehow indicate a desire to invoke the special provisions of 35 U.S.C. § 112, ¶6, to define the invention. To the contrary, if the provisions of 35 U.S.C. § 112, ¶6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ", if the claims also recite any structure, material or acts in support of that means or step, or that perform the recited function, then it is the clear intention of the inventors not to invoke the provisions of 35 U.S.C. § 112, ¶6. Moreover, even if the provisions of 35 U.S.C. § 112, ¶6 are invoked to define the claimed inventions, it is intended that the inventions not be limited only to the specific structure, material or acts that are described in the embodiments, but in addition, include any and all structures, materials or acts that perform the claimed function as described in alternative embodiments or forms of the invention, or that are well known present or later-developed, equivalent structures, material or acts for performing the claimed function.

BRIEF DESCRIPTION OF THE DRAWINGS

In the following examples of the illustrated embodiments, references are made to the accompanying drawings which form a part hereof, and in which is shown by way of illustration various embodiments in which the systems, methods, processes, and/or apparatuses disclosed herein may be practiced. It is to be understood that other embodiments may be utilized, and structural and functional changes may be made without departing from the scope.

FIG. 5 depicts a diagram with two views of an embodiment of the present invention with the lid on.

FIG. 28 depicts a photograph of the test setup of the present invention.

FIG. 30 depicts a table that outlines the various test protocols used over the course of testing the present invention

FIG. 44 depicts an illustration showing different frames of reference for different observers for the theory of relativity.

DETAILED DESCRIPTION

Figure 1:
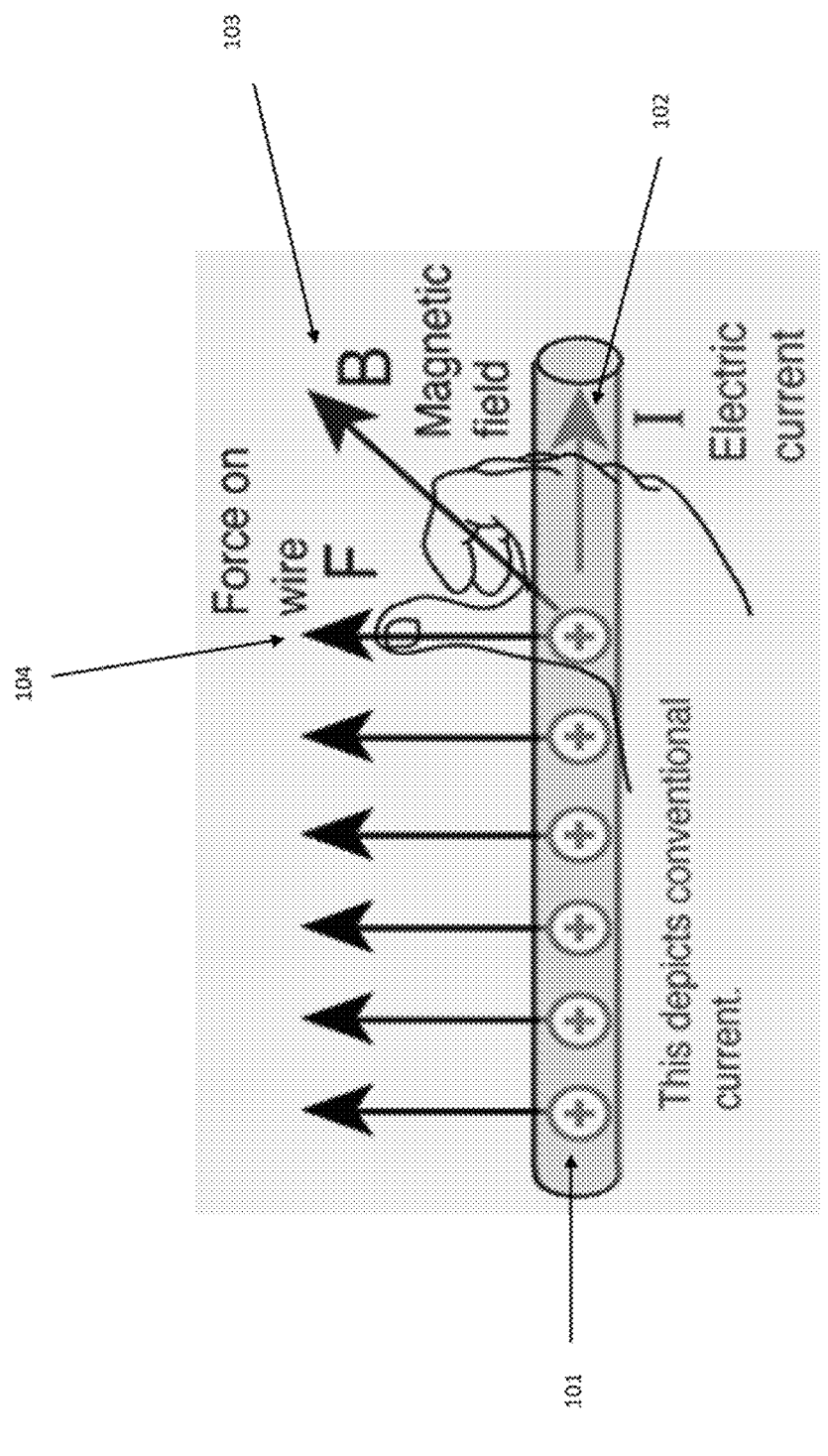
FIG. 1 depicts the right-hand rule for the electromagnetic force on a current carrying wire in a magnetic field.

In the following description, and for the purposes of explanation, numerous specific details, process durations, and/or specific formula values are set forth in order to provide a thorough understanding of the various aspects of exemplary embodiments. However, it will be understood by those skilled in the relevant arts that the apparatus, systems, and methods herein may be practiced without all of these specific details, process durations, and/or specific formula values.

Other embodiments may be utilized, and structural and functional changes may be made without departing from the scope of the apparatus, systems, and methods herein. It should be noted that there are different and alternative configurations, devices, and technologies to which the disclosed embodiments may be applied. The full scope of the embodiments is not limited to the examples that are described below.

To reduce the complexity and length of the Detailed Specification, Applicant(s) herein expressly incorporate(s) by reference all of the following materials identified in each paragraph below. The incorporated materials are not necessarily "prior art" and Applicant(s) expressly reserve(s) the right to swear behind any of the incorporated materials. A more complete understanding may be derived by referring to the description when considered in connection with the following Attachments.

If the Examiner believes that any of the above-incorporated material constitutes "essential material" within the meaning of 37 CFR 1.57(c)(1)-(3), applicant(s) will amend the specification to expressly recite the essential material that is incorporated by reference as allowed by the applicable rules.

The method and apparatus described herein discloses systems and methods for an apparatus that produces magnetic field pulsations to provide a beneficial or energetic effect to a user. It is well accepted that magnetic field pulsations can directly impact the human nervous system. The nervous system is composed of neurons and glial cells, which far outnumber neurons throughout the nervous system.

The progenitor glial cell, the primitive astrocyte, differentiates into all the other types of glial cells (astrocytes, oligodendrocytes, microglia and ependymal cells, in the central nervous system and Schwann cells in the peripheral nervous system). Primitive astrocytes also differentiate into neurons themselves. Glial cells provide nutritive support for neurons in addition to having other interactions with neurons.

It has long been established that neurons communicate with other neurons through a synapse, a structure that permits a neuron to pass an electrical or chemical signal to another neuron. These signals predispose the receiving neuron to activate or fire, often causing the conduction of a nerve impulse down its axon. Neuronal firing can be viewed as a binary digital event, it is either activated and fires or not. Neuronal firing is accomplished by changes in molecular aspects of the neuron's cell membrane allowing an unequal influx of sodium ions and efflux of potassium ions altering the electrical gradient that had been established by the active sodium-potassium pump mechanism, located in the neuron's cell membrane.

Normally, the active sodium-potassium pump mechanism creates an ionic imbalance causing the inside of the neuron to have a more negative electric charge as compared to the extracellular fluid surrounding the neuron. If equal amounts of sodium and potassium ions were transported across the membrane by the pump, the net charge transfer would be zero, as both ions are positive; there would be no net flow of current and no effect on the membrane potential. Actions of the sodium-potassium pump, in many neurons cause three sodium ions to be transported out of the cell for every potassium ion transported in; sometimes the ratio is three sodium ions for every two potassium ions, and in a few neurons it is two sodium ions for one potassium ion. This inequality of ionic transfer produces a net efflux of positive charge, maintaining a polarized membrane with the inner surface slightly negative in relation to the outer surface. Because it creates this potential difference across the membrane, the sodium-potassium pump is said to be electrogenic.

The glial cell is an important regulator of the potassium ion in the extracellular fluid at the outer surface of the neuron's membrane, as it has the ability to concentrate potassium ions internally, thereby reducing the ability of the neuron to concentrate potassium ions internally. Glial cells, therefore, play a regulatory role in neuronal firing by influencing the electrical gradient across the neuron's cell membrane.

Glial cells can also uptake neurotransmitters within the synapse, further impacting neuronal firing and therefore neuronal firing rates.

It is particularly noteworthy that oligodendrocytes centrally and Schwann cells peripherally, communicate with similar cells, adjacent to them, through gap junctions in their cell membranes. This allows ionic transfer from the cytoplasm of one glial cell to the cytoplasm of adjacent glial cells. Oligodendrocytes can also communicate with astrocytes in a similar manner. These glial cells, therefore, form an analog network or circuitry, independent of the digital neuronal circuitry. This glial cell network was termed "the DC perineural system" by its discoverer, Robert O. Becker, M.D. (The Body Electric, 1985, Robert O. Becker, M.D. and Gary Selden).

Dr. Becker's research on the perineural system found that the Schwann cells carry the electrical signals that cause bone fractures to heal. This provided the foundation for the development of bone growth stimulators to heal recalcitrant bone fractures.

It is well accepted that the nervous system in its entirety, including the brain, consisting of the cerebral hemispheres, functions as the organ of conscious human perception and experience, as we understand it. What we experience in this life physically, emotionally, mentally and arguably spiritually, is registered by the cells in the nervous system in the form of innumerably complex chemical reactions and electromagnetic impulses. Even though, principally the brain, presumably experiences these phenomena directly, as evidenced by reactions to these events from the brain itself, it remains conceivable that these registrations in the brain are also somehow transmitted to or impact another form of energy and/or matter, not presently recognized by science or medicine. It is also conceivable that the nervous system, including the brain, brainstem, cerebellum, spinal cord, peripheral nerves and its extension, the autonomic nervous system, could potentially receive inputs from another form of energy and/or matter it may be in communication with.

Although the current in the DC perineural system is direct current (DC), there exists a strong scientific basis to understand that, if influenced by electrical, electromagnetic or magnetic energy, it could also convey frequency content and vary in amplitude. Therefore, given the existence of an analog perineural conduction network that can potentially modify neuronal firing, it is theorized that the DC perineural system could be used to influence and entrain neuronal firing rates. This could have profound applications for affecting sleep, in addition to potentially treating or healing a multitude of other medical, psychological and emotional conditions, as well as modifying states of consciousness.

The phenomenon of sleep or at least a state resembling sleep, first appears in certain species of fish and has progressively become a more complex phenomenon in higher animal species. In mammals, particularly human beings, sleep has been studied extensively in laboratory settings, resulting in an appreciation that mammalian sleep is comprised of cyclical state changes that can be documented through standard scientific measurement techniques.

The first widely accepted classification of different stages of sleep was first published in 1968 (Rechtschaffen A, Kales A, eds. A manual of standardized terminology, techniques and scoring system of sleep stages in human subjects. Los Angeles: Brain Information Service/Brain Research Institute, University of California, 1968). On the basis of these scoring rules (R&K), sleep recordings are divided into 7 discrete stages (wake, stage 1 or S1, stage 2 or S2, stage 3 or S3, stage 4 or S4, stage REM, and movement time). This scoring system is based upon measurements taken during polysomnography, which typically measures the electroencephalogram (EEG), electro-oculogram (EOG), electromyogram (EMG) of the chin and legs, electrocardiogram (EKG), blood oxygen saturation, respiratory activity (respiratory flow and effort), and sometimes other measurements as well.

Almost 40 years later, the American Academy of Sleep Medicine (AASM) modified the standard guidelines for sleep classification by Rechtschaffen and Kales and developed a new guideline for terminology, recording method, and scoring rules for sleep-related phenomena. (Iber C, Ancoli-Israel S, Chesson A, Quan SF, eds. The AASM manual for the scoring of sleep and associated events: rules, terminology, and technical specification, 1st ed. Westchester, IL: American Academy of Sleep Medicine, 2007.). In summary, the major changes of the new manual comprise EEG derivations, the merging of Stages 3 and 4 into N3 (N1=Stage 1, N2=Stage 2), the abolition of the stage "movement time," and the simplification of many context rules.

It should be noted that the primary measurements used in determining sleep and its' stages are generally limited to the analysis of EEG, EOG and chin EMG measurements. The structures of the nervous system that directly manifest EEG, EOG and chin EMG signals are the cerebral hemispheres, the thalamus (part of the upper brainstem called the diencephalon) and cranial nerves 3, 4, 6 and 12. This represents a limited subset of the entire nervous system. However, as a result of the focused attention on these signals, the initiation, maintenance and quality of sleep is often perceived as derived from these aspects of the nervous system, particularly the cerebral hemispheres and thalamus. The focus on the cerebrum has occurred, because that is what directly generates the EEG. The various brainwave states, generally define 4 of the 5 stages of sleep, according to the existing guidelines. As such, adherence to these guidelines in clinical practice and research, creates a high degree of focus on the cerebral hemispheres and EEG.

Other areas of the nervous system have been overlooked as a result, in terms of causing EEG changes, especially cyclical changes. In particular, the autonomic nervous system, which does not directly create brainwaves (EEG), eye movements (EOG) or chin muscle activity (EMG), has been largely ignored as potentially playing a major role in creating sleep and sleep EEG changes.

Adherence to the present guidelines has limited the exploration of alternative measurement and monitoring techniques, as well as therapeutic interventions that may more directly target potential underlying causative mechanisms of sleep and its' stages. For instance, the main thrust of sleep therapeutics has proceeded mainly along pharmaceutical lines, targeting mainly cerebral activity. Pharmaceutical interventions to improve sleep quality, mainly promote sleep through chemical agents that tend to primarily inhibit cerebral activity, causing sedation or reducing anxiety and thought.

A common drug used in the treatment of insomnia to improve sleep is Ambien. Ambien's active ingredient is a chemical named zolpidem. Zolpidem is similar in structure to another class of medication, used to improve sleep, called benzodiazepines. Benzodiazepines have a variety of effects on the nervous system. They have the ability to reduce anxiety and they also work as sedatives. The different effects of benzodiazepines are mediated by different types of receptors on the neuron's cell membrane. Zolpidem is not a benzodiazepine, but it binds to some of the same receptors to which benzodiazepine drugs bind. Zolpidem binds to the receptors in the nervous system that are responsible for benzodiazepine's sedative properties. As a result, zolpidem can cause sedation without generating many of the other effects of benzodiazepines.

Zolpidem binds to a subtype of GABA receptors. GABA is a neurotransmitter that primarily works to inhibit the activity of neurons. At some postsynaptic receptor sites GABA opens chloride channels, causing in most cells a hyperpolarization of the membrane as negative chloride ions diffuse inward to reach its equilibrium potential. When zolpidem binds to this receptor at some locations in the nervous system, it slows or stops activity at these locations, however, binding to this receptor at other locations of the nervous system can produce unwanted side effects.

Zolpidem is often classified as a hypnotic. It diminishes activity in parts of the cerebrum that are responsible for processing thoughts. By slowing cognition, zolpidem makes it easier for patients to fall asleep. Some formulations of Ambien release a constant amount of zolpidem over a period of time, which makes it easier for patients to both fall asleep and stay asleep. Unfortunately, due to the widespread nature of GABA receptors throughout the nervous system, it is difficult to target specific areas of the nervous system that may have a more specific regulatory role in sleep and avoid some of the unwanted side effects.

Developments in the digital frequency analysis of heart rate variability in the 1970's, 80's, 90's and thereafter, have been largely ignored by the general professional sleep community, particularly in the United States. Such measurements yield relevant information pertaining to the activity of the autonomic nervous system (ANS) and its sympathetic and parasympathetic divisions. The frequency range of the digital, frequency analysis of heart rate variability (HRV) data varies between 0.003 Hz and 0.5 Hz, in its broadest range. This range is further subdivided into 3 frequency bandwidths; the VLF band (typically, 0.003 Hz to 0.04 Hz), the LF band (typically, 0.04 Hz to 0.15 Hz) and the HF band (typically, 0.15 Hz to 0.4 Hz).

Measurements of ANS activities has been correlated to EEG activity and the various sleep stages and point to a possible underlying causative role in the development of the various stages of sleep, in addition to performing a regulatory role in the ultradian cycling of endocrine functioning, including the timing and coordination of hormonal release, such as growth hormone and thyroid stimulating hormone.

Deeper stages of sleep (slow wave or delta sleep or Stages S3 and S4 or N3 of sleep) are accompanied by brainwaves between 0.5 Hz and 3.5 Hz, termed the delta frequency band. This deep sleep stage lessens in quality and duration as humans age, which is unfortunate as this sleep stage is particularly restorative and regenerative. The EEG can also record other brainwave patterns, such as theta brainwave band (3.5-7.5 Hz) during periods of light sleep and meditation, the alpha brainwave band (7.5-12.5 Hz) during periods of peaceful relaxation and the beta brainwave band (12.5-35 Hz) during active mental processing.

An article entitled, "Inverse coupling between ultradian oscillations in delta wave activity and heart rate variability during sleep.", written by Gabrielle Brandenberger, Jean Ehrhart, FrancËois Piquard, Chantal Simon, from Laboratoire des ReÂgulations Physiologiques et des Rythmes Biologiques chez l'Homme, 4 rue Kirschleger, 67085 Strasbourg Cedex, France, nicely documents the relationship between activity of the autonomic nervous system and sleep stages, particularly related to delta sleep.

A more complete understanding of the systems, methods, processes, and/or apparatuses disclosed herein may be derived by referring to the illustrative figures and the like-referenced numbers where these elements or acts as depicted are explained in terms of the science, the laws of physics or engineering definitions as known in the art and incorporated herein.

Magnetism: Is a class of physical phenomena that are mediated by magnetic fields. Electric currents and the magnetic moments of elementary particles give rise to a magnetic field, which acts on other currents and magnetic moments. The most familiar effects occur in ferromagnetic materials, which are strongly attracted by magnetic fields and can be magnetized to become permanent magnets, producing magnetic fields themselves. Only a few substances are ferromagnetic; the most common ones are iron, cobalt and nickel and their alloys such as steel.

The magnetic state (or magnetic phase) of a material depends on temperature and other variables such as pressure and the applied magnetic field. A material may exhibit more than one form of magnetism as these variables change.

Electromagnetism: Is a branch of physics involving the study of the electromagnetic force, a type of physical interaction that occurs between electrically charged particles. The electromagnetic force is carried by electromagnetic fields composed of electric fields and magnetic fields, is responsible for electromagnetic radiation such as light, and is one of the four fundamental interactions (commonly called forces) in nature. The other three fundamental interactions are the strong interaction, the weak interaction, and gravitation. At high energy the weak force and electromagnetic force are unified as a single electroweak force.

There are numerous mathematical descriptions of the electromagnetic field. In classical electrodynamics, electric fields are described as electric potential and electric current. In Faraday's law, magnetic fields are associated with electromagnetic induction and magnetism, and Maxwell's equations describe how electric and magnetic fields are generated and altered by each other and by charges and currents.

Magnetostatics: Is the study of magnetic fields in systems where the currents are steady (not changing with time). It is the magnetic analogue of electrostatics, where the charges are stationary. The magnetization need not be static; the equations of magnetostatics can be used to predict fast magnetic switching events that occur on time scales of nanoseconds or less. Magnetostatics is even a good approximation when the currents are not static—as long as the currents do not alternate rapidly.

Electrostatic: A branch of physics that studies electric charges at rest. Since classical physics, it has been known that some materials such as amber attract lightweight particles after rubbing. Electrostatic phenomena arise from the forces that electric charges exert on each other. Such forces are described by Coulomb's law. Even though electrostatically induced forces seem to be rather weak, some electrostatic forces such as the one between an electron and a proton, that together make up a hydrogen atom, is about 36 orders of magnitude stronger than the gravitational force acting between them.

Electromotive force, abbreviated emf (measured in volts), is the electrical action produced by a non-electrical source. A device that converts other forms of energy into electrical energy (a "transducer"), such as a battery (converting chemical energy) or generator (converting mechanical energy), provides an emf as its output.

Coulomb's inverse-square law: Is an experimental law of physics that quantifies the amount of force between two stationary, electrically charged particles. The electric force between charged bodies at rest is conventionally called electrostatic force or Coulomb force. The quantity of electrostatic force between stationary charges is always described by Coulomb's law. The law was first published in 1785 by French physicist Charles-Augustin de Coulomb, and was essential to the development of the theory of electromagnetism, maybe even its starting point, because it was now possible to discuss quantity of electric charge in a meaningful way.

Faraday's law of induction (briefly, Faraday's law) is a basic law of electromagnetism predicting how a magnetic field will interact with an electric circuit to produce an electromotive force (EMF)—a phenomenon called electromagnetic induction. It is the fundamental operating principle of transformers, inductors, and many types of electrical motors, generators and solenoids Magnetic Force on a Current-Carrying Conductor: In physics (specifically in electromagnetism) the Lorentz force is the combination of electric and magnetic force on a point charge due to electromagnetic fields. Variations on this basic formula describe the magnetic force on a current-carrying wire (sometimes called Laplace force), the electromotive force in a wire loop moving through a magnetic field and the force on a charged particle which might be traveling near the speed of light (relativistic form of the Lorentz force).

Figure 2:
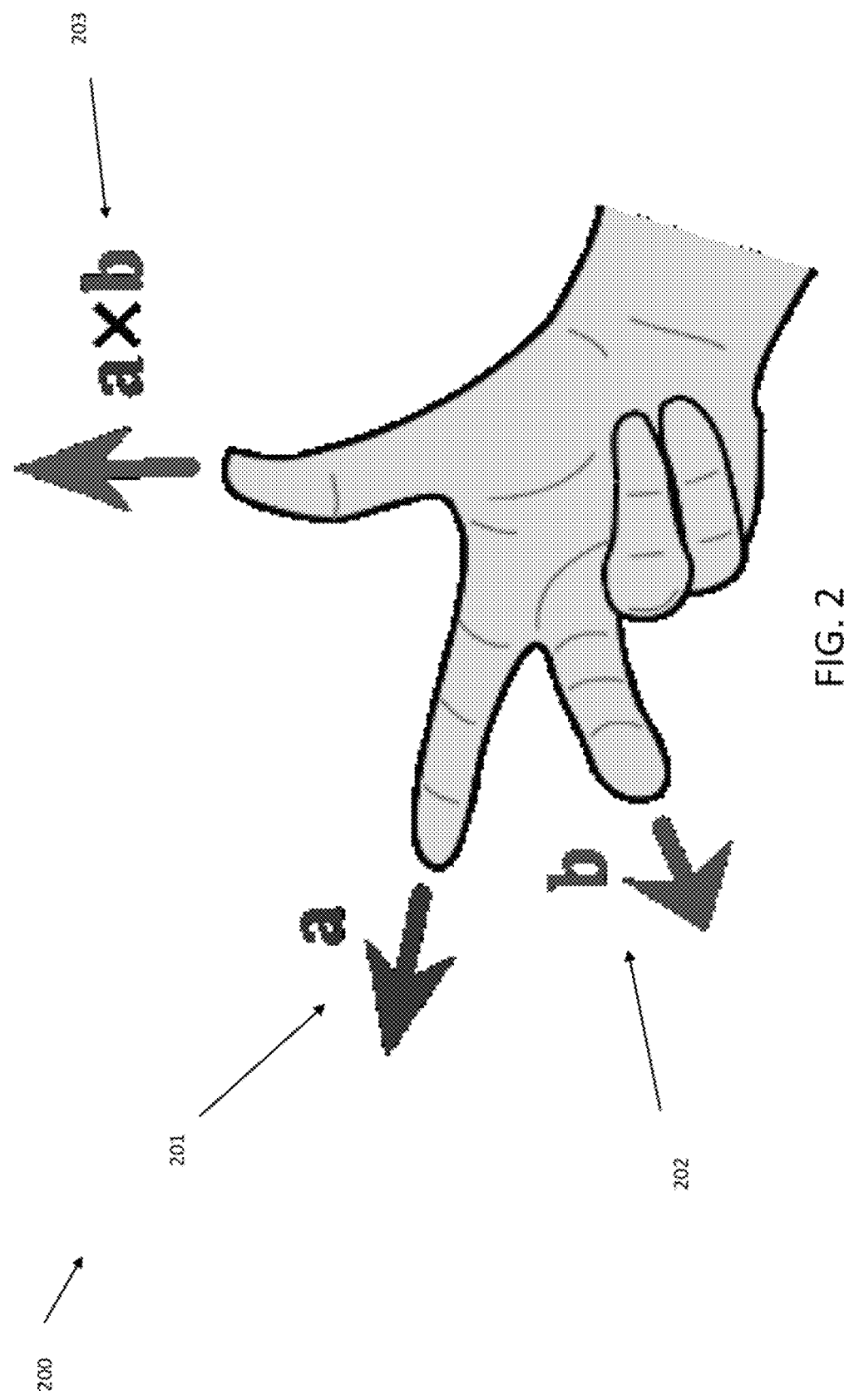
FIG. 2 depicts the right-hand rule for a mathematical operation called the cross product.

Using Lorentz Force equations, the magnetic force through a current-carrying wire can be calculated. One such equation is as follows: $F=qvB \sin \theta$. Where F is force in Newtons, q is the charge, v is the velocity and B is the magnetic field. The equation can be furthered to the following to incorporate the length of the wire: $F=ILB \sin \theta$. Where I is the current (A), L is the length (m), B is the magnetic field (T) and $\sin \theta$ is the angle between the wire and field. If the magnetic force on a current-carrying wire is perpendicular to both the wire and the magnetic field than the direction is given by the right-hand rule. The right-hand rule is by using your right hand to find where the force will be. FIGS. 1 and 2 depicts the right-hand rule for the electromagnetic force on a current carrying wire in a magnetic field. 101 depicts the charge carrying particles in a wire which makes up electrical current. 102 depicts the direction of the electrical current. 103 depicts the direction of an external magnetic field which a person's right-hand fingers would curl from the direction of electrical current towards the direction of the magnetic field. 104 depicts the direction of the electromagnetic force in the direction of a person's thumb. First, curl fingers as if rotating from vector I 102 in FIG. 1 into vector B 103. The thumb 104 will show where the direction of the force F is. Then the following equation can be used to find the force in relation to the vectors I and B using $\vec{F} = \vec{i}L \times \vec{B}$.

Laplace Operator: In mathematics, the Laplace operator or Laplacian is a differential operator given by the divergence of the gradient of a function on Euclidean space. It is usually denoted by the nabla symbol (nabla is a triangular symbol like an inverted Greek delta) $\nabla \cdot \nabla, \nabla^2$. The Laplacian $\nabla \cdot \nabla f(p)$ of a function f at a point p, is (up to a factor) the rate at which the average value off over spheres centered at p deviates from $f(p)$ as the radius of the sphere shrinks towards 0. In a Cartesian coordinate system, the Laplacian is given by the sum of second partial derivatives of the function with respect to each independent variable. In other coordinate systems such as cylindrical and spherical coordinates, the Laplacian also has a useful form.

The Laplace operator is named after the French mathematician Pierre-Simon de Laplace (1749-1827), who first applied the operator to the study of celestial mechanics, where the operator gives a constant multiple of the mass density when it is applied to the gravitational potential due to the mass distribution with that given density. Solutions of the equation $\nabla \cdot \nabla f = 0$, now called Laplace's equation, are the so-called harmonic functions, and represent the possible gravitational fields in regions of vacuum.

The Laplacian occurs in differential equations that describe many physical phenomena, such as electric and gravitational potentials, the diffusion equation for heat and fluid flow, wave propagation, and quantum mechanics. The Laplacian represents the flux density of the gradient flow of a function. For instance, the net rate at which a chemical dissolved in a fluid moves toward or away from some point is proportional to the Laplacian of the chemical concentration at that point; expressed symbolically, the resulting equation is the diffusion equation. For these reasons, it is extensively used in the sciences for modelling all kinds of physical phenomena.

Laplace Transform: The Laplace transform of a function $f(t)$, defined for all real numbers t≥0, is the function F(s), which is a unilateral transform defined by:

$$F(s) = \int_0^\infty f(t)e^{-st}dt \qquad [001]$$

$$\mathcal{L}^{-1}\{F(s)\} = f(t) \qquad [002]$$

$$\mathcal{L}\{f\} = F(s) \qquad [003]$$

$$s = \sigma + i\omega \qquad [004]$$

s is a complex number frequency parameter with σ and ω being real number.

In mathematics, the Laplace transform is an integral transform named after its inventor Pierre-Simon Laplace. It transforms a function of a real variable t (often time) to a function of a complex variable s (complex frequency). The transform has many applications in science and engineering.

The Laplace transform is similar to the Fourier transform. While the Fourier transform of a function is a complex function of a real variable (frequency), the Laplace transform of a function is a complex function of a complex variable. Laplace transforms are usually restricted to functions oft with t≥0. A consequence of this restriction is that the Laplace transform of a function is a holomorphic function of the variable s. Unlike the Fourier transform, the Laplace transform of a distribution is generally a well-behaved function. Techniques of complex variables can also be used to directly study Laplace transforms. As a holomorphic function, the Laplace transform has a power series representation. This power series expresses a function as a linear superposition of moments of the function. This perspective has applications in probability theory.

The Laplace transform is invertible on a large class of functions. The inverse Laplace transform takes a function of a complex variable s (often frequency) and yields a function of a real variable t (often time). Given a simple mathematical or functional description of an input or output to a system, the Laplace transform provides an alternative functional description that often simplifies the process of analyzing the behavior of the system, or in synthesizing a new system based on a set of specifications. For example, Laplace transformation from the time domain to the frequency domain transforms differential equations into algebraic equations.

Maxwell's equations are a set of four differential equations that are the theoretical basis for describing classical electromagnetism. They describe how electric fields and magnetic fields influence each other.

In equations [005-014], B is the magnetic field, $d\vec{a}$ is a segment of area in the integral, $Q_{enclosed}$ is the charge enclosed in the area of integration, $\nabla$ is the divergence operator, ρ is the total charge density per unit volume, E is the electric field, D is the field flux of electrical displacement from polarization, H is an axillary field, J is the current density, $\mu_0$ is the permeability of free space, and $\epsilon_0$ is the permittivity of free space.

Maxwell's second equation says that magnetic monopoles do not exist. While electric monopoles exist, there has never been the discover of magnetic monopoles. This equation states that the magnetic field curls around a current or from north to south from a permanent magnet. This is because the divergence of a magnetic field zero and the fields form closed loops.

Gauss' Law for electricity and Magnetism: Describes the force interaction of electric charges: like charged particles repel each other and opposite charged particles attract. Gauss' Law also describes that electric field lines diverge away from electric charges. This means that positive charged particles act as the source of electric fields and negatively charged particles act as a sink for electric fields.

$$\oint_S B \cdot d\vec{a} = \frac{Q_{enclosed}}{\epsilon_o} \qquad [005]$$

$$\nabla \cdot E = \frac{\rho}{\epsilon_o} \qquad [006]$$

$$\nabla \cdot D = \rho_{free} \qquad [007]$$

Gauss' Law for Magnetism:

$$\varphi_s B \cdot d\vec{a} = 0 \qquad [008]$$

$$\nabla \cdot B = 0 \qquad [009]$$

US 12,611,549 B2

15

Faraday's Law states that an induced magnetic field that is changing in time will give rise to a circulating electric field. This means electric fields are generated from the flow of electrical charges or a changing magnetic flux.

$$\oint_l E \cdot d\vec{l} = -\int_s \frac{\partial}{\partial t}(B \cdot d\vec{a})$$ [010]

$$\nabla \times E = -\frac{\partial B}{\partial t}$$ [011]

Ampere's Law with Maxwell's Addition: Ampere's Law states that a flowing electric current will rise to a magnetic field that circles the flow of current. In addition to this, an electric field that is changing in time will give rise to a magnetic field that curls around the electrical field. This is the electrical displacement term that Maxwell introduced.

$$\oint_l B \cdot d\vec{l} = \mu_o \left( I + \epsilon_o \int_s \frac{\partial}{\partial t}(E \cdot d\vec{a}) \right)$$ [012]

$$\nabla \times B = \mu_o \left( J + \epsilon_o \frac{\partial E}{\partial t} \right)$$ [013]

$$\nabla \times H = J + \frac{\partial D}{\partial t}$$ [014]

Right-Hand Rule: In mathematics and physics, the right-hand rule is a common mnemonic for understanding orientation of axes in three-dimensional space. The right-hand rule arises when dealing with coordinate axes, rotation, spirals, electromagnetic fields, mirror images, and enantiomers in mathematics and chemistry. The right-hand rule shows the direction of a cross product.

FIG. 2 depicts the cross product of two vectors is often taken in physics and engineering. You point your index finger in the direction of the first vector 201. Then you point your middle finger in the direction of the second vector 202. Your thumb points in the direction of the resultant vector 203. The cross product is applied to many physics and engineering calculations. For example, in statics and dynamics, torque is the cross product of lever length and force, while angular momentum is the cross product of linear momentum and distance. In electricity and magnetism, the force exerted on a moving charged particle when moving in a magnetic field B is given by:

$$\vec{F} = q(\vec{v} \times \vec{B})$$ [015]

The direction of the cross product may be found by application of the right-hand rule as follows:

The index finger points in the direction of the velocity vector v.

The middle finger points in the direction of the magnetic field vector B.

The thumb points in the direction of the cross-product F. For example, for a positively charged particle moving to the North, in a region where the magnetic field points West, the resultant force points up.

The right-hand rule is in widespread use in physics. A list of physical quantities whose directions are related by the right-hand rule is given below.

For a rotating object, if the right-hand fingers follow the curve of a point on the object, then the thumb points along the axis of rotation in the direction of the angular velocity vector.

A torque, the force that causes it, and the position of the point of application of the force.

A magnetic field, the position of the point where it is determined, and the electric current (or change in electric flux) that causes it.

A magnetic field in a coil of wire and the electric current in the wire.

The force of a magnetic field on a charged particle, the magnetic field itself, and the velocity of the object.

The vorticity at any point in the field of flow of a fluid.

The induced current from motion in a magnetic field (known as Fleming's right-hand rule).

The x, y and z unit vectors in a Cartesian coordinate system can be chosen to follow the right-hand rule. Right-handed coordinate systems are often used in rigid body and kinematics.

Voltage Generated in a Moving Wire: The voltage generated in a moving wire is called Motional EMF (Electromotive Force). The general equation for this is $$emf = vBL \sin \theta.$$ [016]

Where v is the velocity, B is the magnetic field, L is the length of the wire, and $\sin \theta$ is the angle between the magnetic field and wire. When a conductor moves through a magnetic field there will be a generated motional emf. This is one example of Faraday's Law and it arises from the magnetic force. The voltage generated in length of wire, presuming that the entire length moves through a uniform field, is given by the equation [016].

For example, you want to find the strength of the magnetic force a distance away from the magnet. The diameter of the magnet is 0.1 m and the strength at the edge is 1.4 T. First, solve for k with to find the distance.

$$1.4T = \frac{k}{.05^{-3}}$$ [017]

$$k = 0.000175$$ [018]

Next, use the equation for emf.

$$Emf = vBL \sin \theta$$ [019]

One variable to first solve is B, the magnetic field. To solve for B the inverse cube for a dipole.

$$B = \frac{k}{r^3}$$ [020]

To solve for r the Pythagoras theorem was used.

$$r = \sqrt{d^2 + L^2}$$ [021]

Next, substitute r into the equation to solve for B $$B = \frac{k}{\sqrt{d^2 L^{2^3}}}$$ [022]

Next, substitute B back into the emf equation and then integrate. An integration tool was used to make the calculations.

$$\int emfdL = \int vB\sin\theta dL = \int_{-0.5}^{0.5} \frac{0.000175}{\left(d^2 + L^2\right)^{3/2}} dL \qquad [023]$$

$$Emf = 1.71 \text{ mV} \qquad [024]$$

Figure 3:
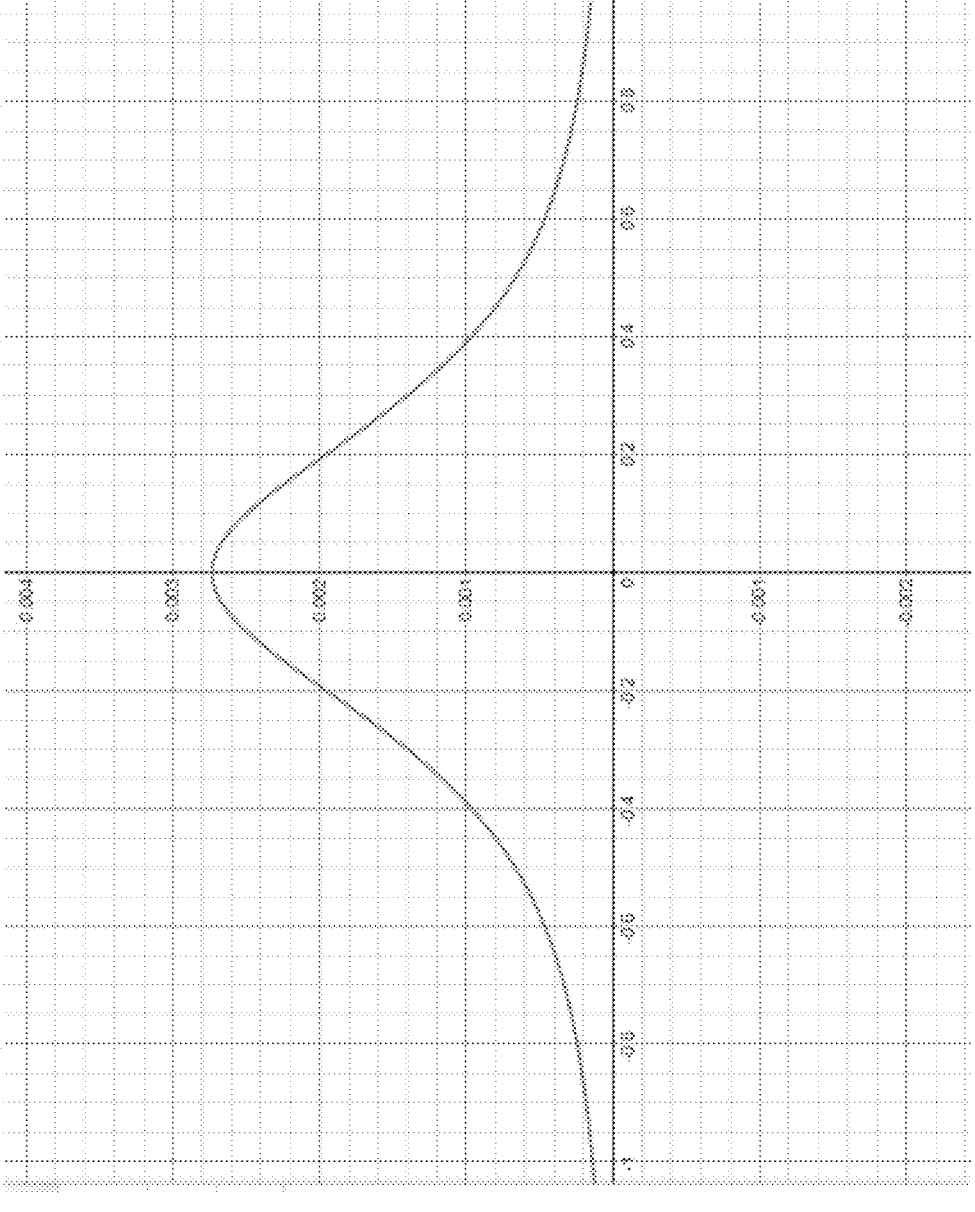
FIG. 3 depicts an emf graph with the device 40 cm away from a leg.
Figure 3:
Figure 3:
Figure 4:
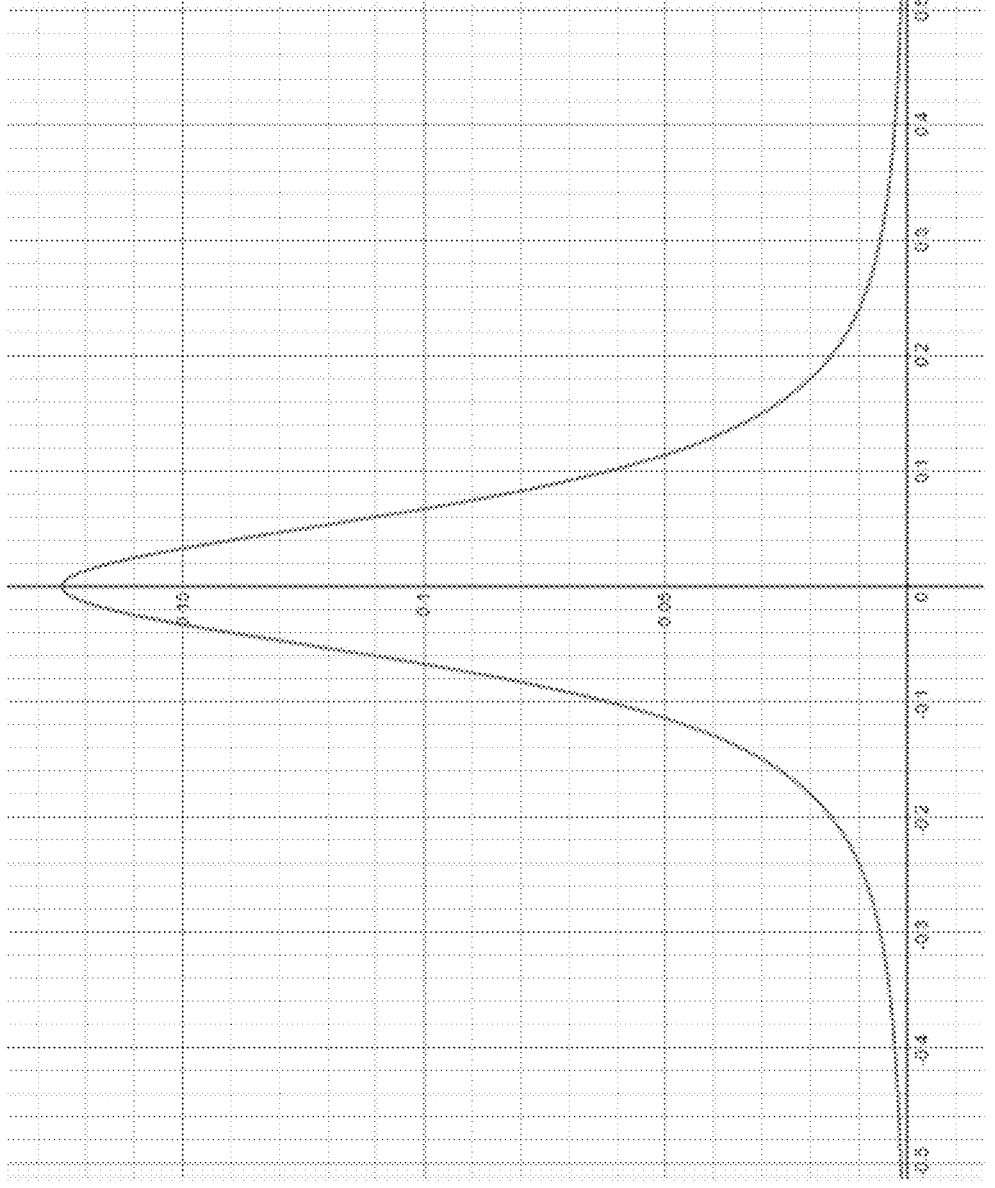
FIG. 4 depicts an emf graph with the device 10 cm away from a leg.
Figure 4:
Figure 5:
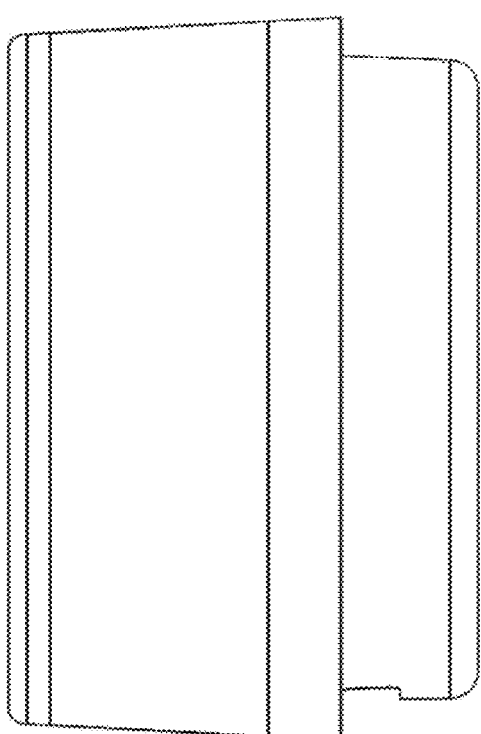
Figure 5:
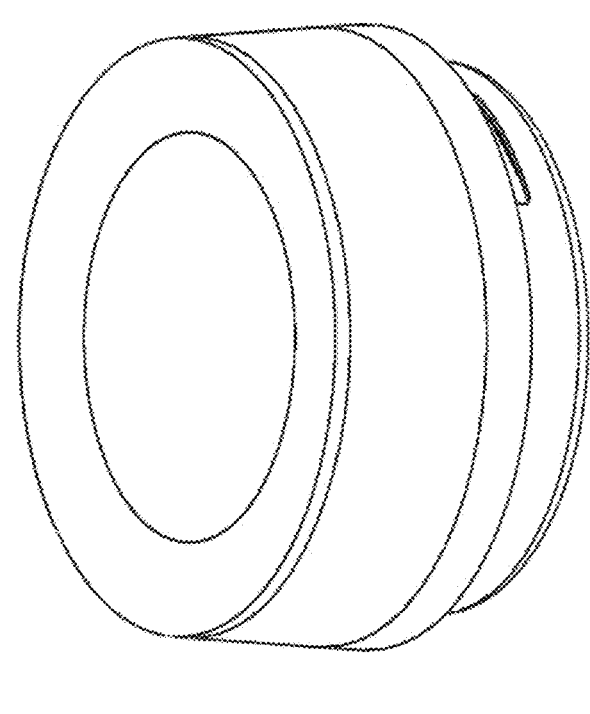
Figure 6:
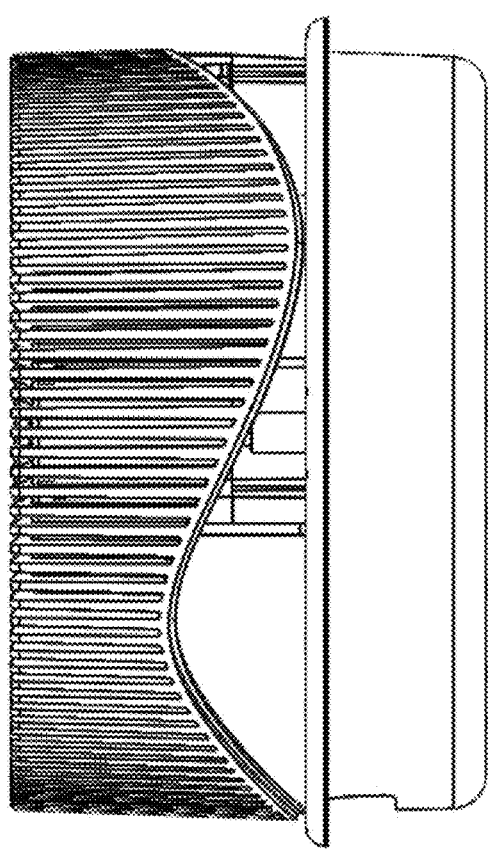
FIG. 6 depicts a diagram with two views of the embodiment of the present invention with the lid off.
Figure 6:
Figure 6:
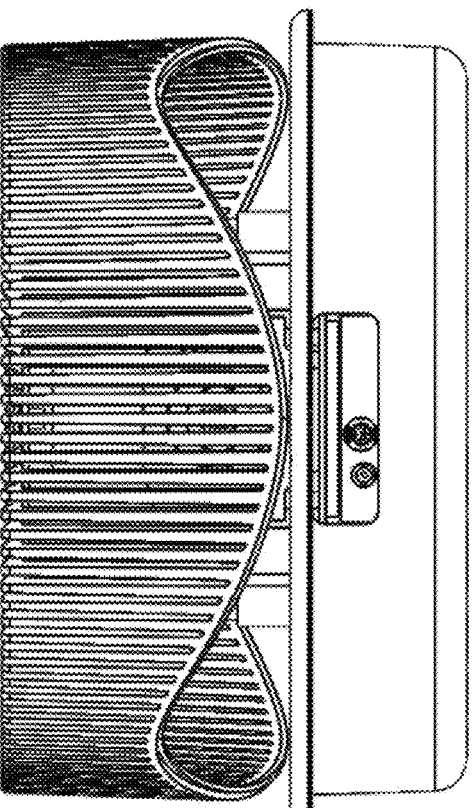
Figure 7:
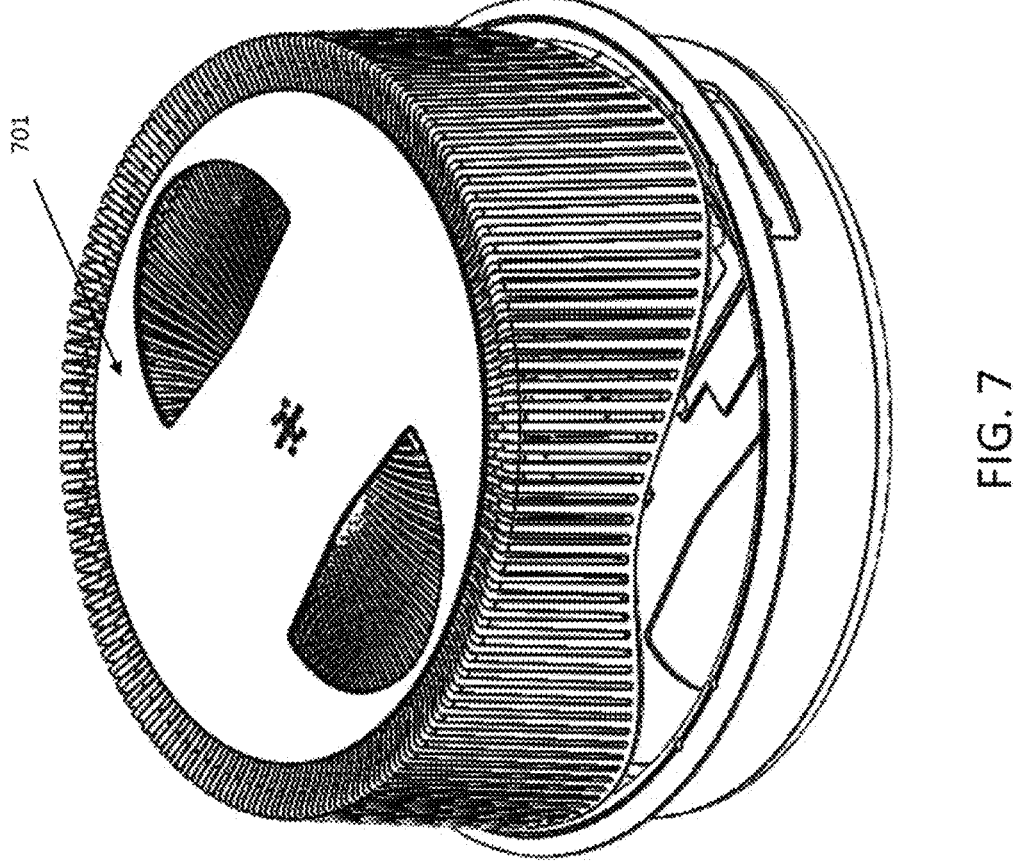
FIG. 7 depicts a diagram with an isometric view of the embodiment of the present invention with the lid off.
Figure 7:

As a result, with the set parameters the emf field calculated to be 1.71 mV. The equation can also be graphed to show the relationship between how close the device is to a body part, for example a leg. FIG. 3 depicts the device 40 cm away from the leg. FIG. 4 depicts the device 10 cm away from the leg. As one can see the further away your leg is from the device there is less amount of emf peak.

Ohms law: Ohm's law states that the current through a conductor between two points is directly proportional to the voltage across the two points. Introducing the constant of proportionality, the resistance.

$$I = \frac{V}{R_\Omega} \qquad [025]$$

Signal Processing Welch's Method: Welch's method, named after P. D. Welch, is an approach for spectral density estimation. It is used in physics, engineering, and applied mathematics for estimating the power of a signal at different frequencies. The method is based on the concept of using periodogram spectrum estimates, which are the result of converting a signal from the time domain to the frequency domain. Welch's method is an improvement on the standard periodogram spectrum estimating method and on Bartlett's method, in that it reduces noise in the estimated power spectra in exchange for reducing the frequency resolution. Due to the noise caused by imperfect and finite data, the noise reduction from Welch's method is often desired.

The Welch method is based on Bartlett's method and differs in two ways:

The signal is split up into overlapping segments: the original data segment is split up into L data segments of length M, overlapping by D points.

If $$D = \frac{M}{2},$$

the overlap is said to be 50%

If D=0, the overlap is said to be 0%. This is the same situation as in the Bartlett's method.

The overlapping segments are then windowed after the data is split up into overlapping segments, the individual L data segments have a window applied to them (in the time domain). Most window functions afford more influence to the data at the center of the set than to data at the edges, which represents a loss of information. To mitigate that loss, the individual data sets are commonly overlapped in time (as in the above step). The windowing of the segments is what makes the Welch method a "modified" periodogram. After doing the above, the periodogram is calculated by computing the discrete Fourier transform, and then computing the squared magnitude of the result. The individual periodograms are then averaged, which reduces the variance of the individual power measurements. The end result is an array of power measurements vs. frequency.

Matlab is used to process the signals being emitted by the device. Matlab's pwelch function is used with five input arguments. The first input is the data set, the second input is the window parameter, the alternate input is the sample overlap, the fourth input is the number of Fast Fourier Transform points, and the fifth input is the sampling frequency.

$$[Pxx,F]=\text{pwelch}(X,\text{WINDOW},\text{NOVERLAP},\text{NFFT},Fs) \qquad [026]$$

X: returns the Power Spectral Density (PSD) estimate, Pxx, of a discrete-time signal, X, using Welch's averaged, modified periodogram method. When X is a vector, it is converted to a column vector and treated as a single channel. When X is a matrix, the PSD is computed independently for each column and stored in the corresponding column of Pxx.

WINDOW: when WINDOW is a vector, divides each column of X into overlapping sections of the same length as WINDOW, and then uses the vector to window each section. If WINDOW is an integer, pwelch divides each column of X into sections of length WINDOW, and uses a Hamming window of the same length. If the length of X is such that it cannot be divided exactly into an integer number of sections with 50% overlap, X is truncated. A Hamming window is used if WINDOW is omitted or specified as empty.

NOVERLAP: uses NOVERLAP samples of overlap from section to section. NOVERLAP must be an integer smaller than WINDOW if WINDOW is an integer, or smaller than the length of WINDOW if WINDOW is a vector. If NOVERLAP is omitted or specified as empty, it is set to obtain a 50% overlap.

NFFT: specifies the number of FFT points used to calculate the PSD estimate. For real X, Pxx has length $$\frac{NFFT}{2} + 1$$

if NFFT is even, and $$\frac{NFFT + 1}{2}$$

if NFFT is odd. For complex X, Pxx always has length NFFT. If NFFT is specified as empty, NFFT is set to either 256 or the next power of two greater than the length of each section of X, whichever is larger. If NFFT is greater than the length of each section, the data is zero-padded. If NFFT is less than the section length, the segment is "wrapped" (using DATAWRAP) to make the length equal to NFFT. This produces the correct FFT when NFFT is smaller than the section length.

Fs: returns a PSD computed as a function of physical frequency. Fs is the sampling frequency specified in hertz. If Fs is empty, it defaults to 1 Hz.

Bartlett's Method: In time series analysis, Bartlett's method is used for estimating power spectra. It provides a way to reduce the variance of the periodogram in exchange for a reduction of resolution, compared to standard periodograms. A final estimate of the spectrum at a given frequency is obtained by averaging the estimates from the periodograms at the same frequency derived from a non-overlapping portion of the original series. The method is used in physics, engineering, and applied mathematics. Common applications of Bartlett's method are frequency response measurements and general spectrum analysis.

Periodogram: In signal processing, a periodogram is an estimate of the spectral density of a signal. It is the most common tool for examining the amplitude vs frequency characteristics of FIR filters and window functions. FFT analyzers are also implemented as a time-sequence of peri-odograms.

Window Function: In signal processing and statistics, a window function is a mathematical function that is zero-valued outside of some chosen interval, normally symmetric around the middle of the interval, usually near a maximum in the middle, and usually tapering away from the middle. Mathematically, when another function or waveform/data-sequence is "multiplied" by a window function, the product is also zero-valued outside the interval: all that is left is the part where they overlap, the "view through the window". Equivalently, and in actual practice, the segment of data within the window is first isolated, and then only that data is multiplied by the window function values. Thus, tapering, not segmentation, is the main purpose of window functions.

The reasons for examining segments of a longer function include detection of transient events and time-averaging of frequency spectra. The duration of the segments is deter-mined in each application by requirements like time and frequency resolution. But that method also changes the frequency content of the signal by an effect called spectral leakage. Window functions allow us to distribute the leakage spectrally in different ways, according to the needs of the particular application.

Medicine is rapidly evolving: new drugs, new devices and new techniques are constantly introduced to improve patient care. And yet, despite these many innovative advances, there are some mainstays of modern medicine that are thousands of years old and have withstood the test of time. We therefore find it noteworthy and reasonable to include a brief discussion regarding the metaphysical aspects and theories that may withstand the test of time as well; as practitioners of the art of magnetic stimulation, it is not our job to judge the validity of any aspects of the invention; our job is to present as best we can novel systems and methods, as embodied by the invention, that are based on fact evidence gathered and presented logically herein. It is also notewor-thy certain data collected and presented in view of the laws of physics and sciences may allow certain new theories maybe not yet fully understood to emerge for consideration, including the use of magnetic stimulation on one or more physiological mechanisms dealing with the functions and activities of living organisms and their parts, including all physical and chemical processes.

Today it is well understood that Metaphysics is the branch of philosophy that examines the fundamental nature of reality, including the relationship between mind and matter, between substance and attribute, and between potentiality and actuality. The word "metaphysics" comes from two Greek words that, together, literally mean "after or behind or among [the study of] the natural". It has been suggested that the term might have been coined by a first century editor who assembled various small selections of Aristotle's works into the treatise we now know by the name Metaphysics (ta meta ta phusika, 'after the Physics', another of Aristotle's works).

Metaphysics studies questions related to what it is for something to exist and what types of existence there are. Metaphysics seeks to answer, in an abstract and fully general manner, simple questions like what is there, and what is it like? Topics of metaphysical investigation include existence, objects and their properties, space and time, cause and effect, and possibility.

So, with the above in mind, it is well understood the nervous system uses electromagnetic energy so it is possible that interaction with an unknown form of energy and/or matter can happen assuming this unknown form of energy and/or matter can interact with electromagnetism. Since the nervous system, including the brain and this possible unknown aspect of self could be synergistic and present since birth, these different aspects of self would not likely be recognized by one's self as being different parts of one collective mind. However, for the sake of this discussion, mind derived solely from brain and potentially lower por-tions of the nervous system will be termed lower mind and the other potential form of mind will be termed higher mind.

Human experiences take place during different states of consciousness or quality of awareness, which conceivably could be determined to some extent by which of the minds are actively participating. For instance, withdrawing one's hand from a painful stimulus and becoming aware of the pain, the painful stimulus and one's reaction to it, can solely result from lower mind. Being mindful of one's emotions and mental thoughts and overriding an impulse to respond in a characteristic manner and instead respond in an unchar-acteristic manner, may evidence the intervention of higher mind. This latter example, however, could arguably also result only from lower mind in that a different part of the brain could be endowed with the ability to be mindful, as the brain does have a functional hierarchy, as evidenced by secondary and tertiary neuronal circuits, that could allow for this supervisory capability.

It is noted that some humans can perceive an intricate, multi-dimensional energy-particle system, which courses throughout and around the physical body. Some people claim this energy-particle matrix to be dark matter and dark energy. In this document this human energy-particle system will be referred to as HEPS, Human Energy-Particle System.

Deeper stages of sleep (delta sleep or Stages 3 and 4 of sleep) are accompanied by brainwaves of less than 3.5 Hz. These deep sleep stages lessen in quality and duration as humans age, which is unfortunate as these sleep stages are particularly restorative. The EEG can record other patterns, such as alpha brainwaves (7.5-12.5 Hz) during periods of peaceful relaxation and beta brainwaves (12.5-35 Hz) during active mental processing.

For many years, biofeedback and neurofeedback practi-tioners have been working with clients with EEG monitoring devices to help clients recognize when they are in different states of consciousness so that they can self-replicate these states. The clinical reasons for this practice include the treatment of insomnia, anxiety, depression, PTSD, pain control, addictions, and many other unwanted symptoms and conditions, including stress related illnesses and condi-tions not mentioned. Training clients to recognize alpha-theta brainwave states to help ameliorate these conditions and to aid the client in later self-inducing these states has reported efficacy rates of 50%-80%, however it is a time-consuming process, requiring dedication and practice, which limits its utility and widespread adoption.

Recognizing that artificial induction of these brainwave states could potentially be much faster and more reliably achieved, certain methodologies have been developed to directly stimulate the brain. These methods include transcra-nial magnetic stimulation using electromagnetic and mag-netic stimulation to induce electrical currents in the brain and low frequency transcranial electrical stimulation. These various forms of stimuli have all been directed at the physical body, specifically at the brain directly or its sensory apparatus. These various methods often either lack adequate efficacy or have technical, cost or governmental regulatory issues that limit widespread adoption to effectively treat numerous medical illnesses and human or animal conditions.

To achieve more natural entrainment of brainwaves a more holistic approach may be required. Even though the first brainwave recordings were made nearly a century ago, medical science still does not know the exact genesis of brainwaves. It is presumed that brainwaves are the summation of action potentials from the firing of nerves nearest the recording electrode. However, DC potentials have also been reliably measured, but located along the perineural coverings of neurons, not the nerve tissue inside those coverings, revealing that the nervous system is endowed with an additional level of electrical activity. The summation of varying DC potentials can also produce patterns resembling what is seen using EEG recording techniques. Furthermore, these DC potentials along the perineural system exist not only at the level of brain, but everywhere there are nerves that convey this DC (or very slow frequency) potential; in the brainstem, spinal cord and peripherally. This DC perineural system exists throughout the entire body, as nerves penetrate every tissue of the body as they make their way to influence every cell of the body.

It's not uncommon that many individuals who strive to develop insight into themselves, report having an inner dialogue. In such a dialogue a thought or question can be posed from one's egoic mind followed by the egoic mind entering a receptive state of being. This receptive state can be generated by various techniques, such as meditation, biofeedback to elicit deep relaxation, and hypnosis, induced by self or another. During this receptive period, a thought or answer can be received, which generally offers another perspective. Presumably this new thought or answer issues from one's higher mind or HEPS.

The organic brain operates electro-chemically. As such, it can be interacted with either chemically, as is often done with pharmaceuticals, or electromagnetically, as is done with electro-shock therapy and electrical, electromagnetic or magnetic stimulation. Assuming the HEPS does interact directly with the brain, then the brain could be impacted by direct stimulation of the HEPS, independent of direct brain stimulation. Since the HEPS is clearly not of a definable physical nature, it is not chemically-based, as we understand chemistry. Therefore, if it exists and interacts with the brain, it must do so through electrical and/or magnetic means. Since the HEPS cannot be measured electrically, it is assumed to be related to magnetism (not electromagnetism) or can, in some manner, interact with magnetic phenomena. In this context, magnetism is to be differentiated from electromagnetism. Science does recognize that the force carrier associated with electromagnetism is the photon and it also acknowledges that no measurable photons are measurable in association with a magnetic field. Clearly, electromagnetism differs from magnetism in this manner and also by the fact that electromagnetism is associated with a positive and negative pole and magnetism is not.

It has been demonstrated that this receptive state of being is achieved in meditative states when one's brain is functioning at lower EEG frequencies consistent with less egoic-based mental activity or functioning.

The brain typically operates at low frequencies, typically 1 Hz to 30 Hz, but as high as 40 Hz or more. The key frequency range for significantly influencing many brain functions, including sleep, ranges from 0.5 Hz to about 20 Hz. At these lower frequencies only, particularly at frequencies below 8 Hz, continuous magnetic stimulation cannot be accomplished using electromagnetism produced from running current through wire coils, as the resistance at these frequencies is so low that the current which develops is far too high and the coil exceeds safe temperature limits. Therefore, the magnetic stimulation at these low frequencies is best accomplished using magnetic frequencies generated directly by magnetic materials.

In a first embodiment of the present invention, motion can be applied to magnetic materials directly by creating a system of magnetic materials with a mechanism applying a time varying force. That system in total can then be affected by another mechanism applying separate and different time varying forces to it, thereby creating a more complex magnetic waveform of various frequencies, because of the varying magnetic motion and so on. In the first embodiment, the magnetic material may be stationary. The magnetic material may be surrounded by materials that condition the magnetic field, such as steel or iron, and/or directionally orient the magnetic field, such as aluminum. The magnetic field can then be influenced by moving materials in proximity to the magnetic field that provide variable impedance or blockage of the field to intermittently reduce or completely block the outward transmission of the magnetic field.

Figure 8:
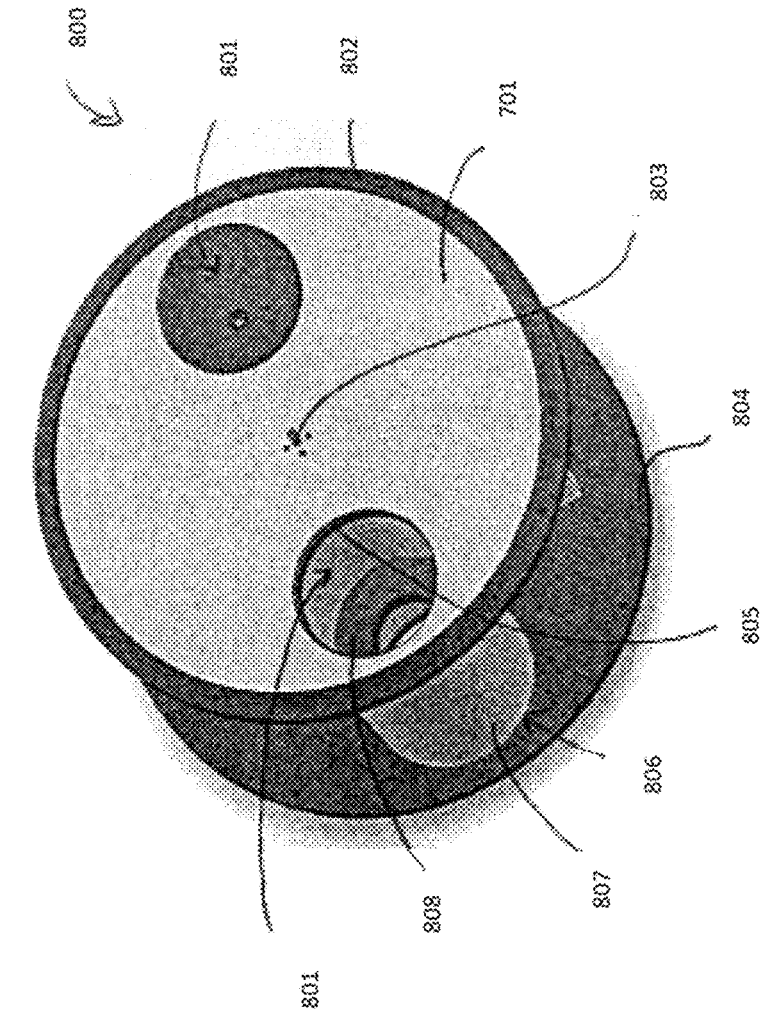
FIG. 8 depicts a diagram with a top view and an alternate view of the embodiment of the present invention with the lid off.
Figure 8:
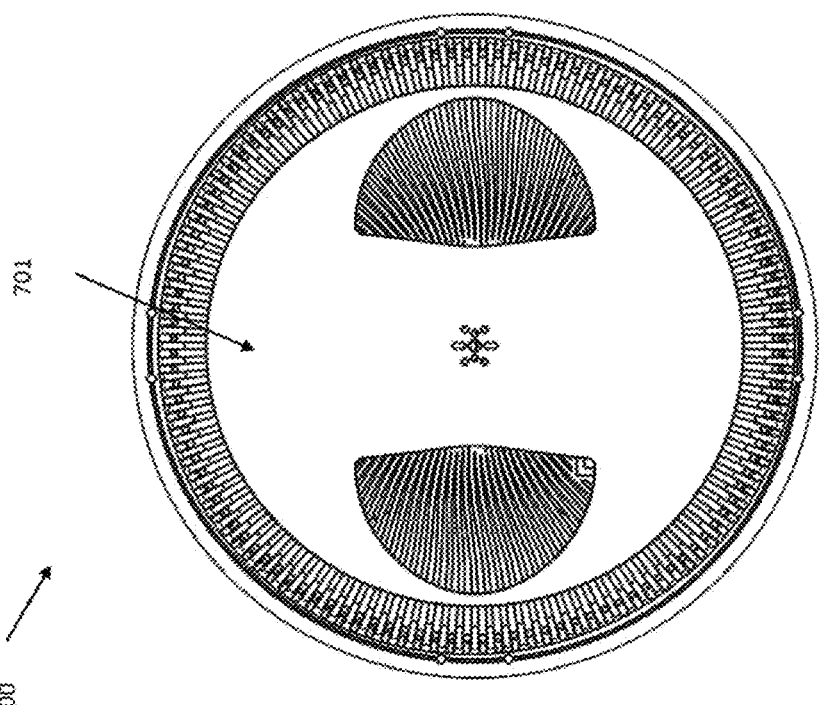
Figure 9:
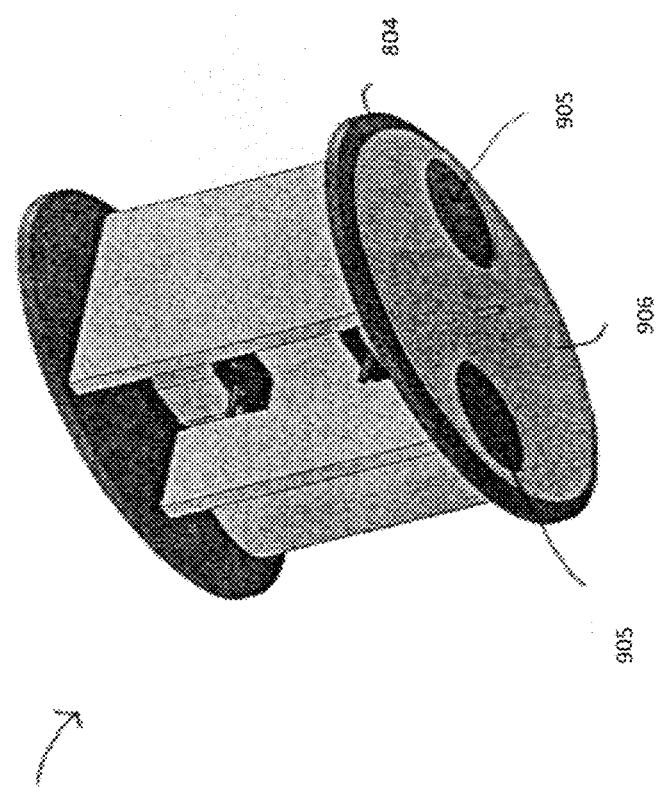
FIG. 9 depicts a diagram with two alternate views of the embodiment of the present invention with the lid off.
Figure 9:
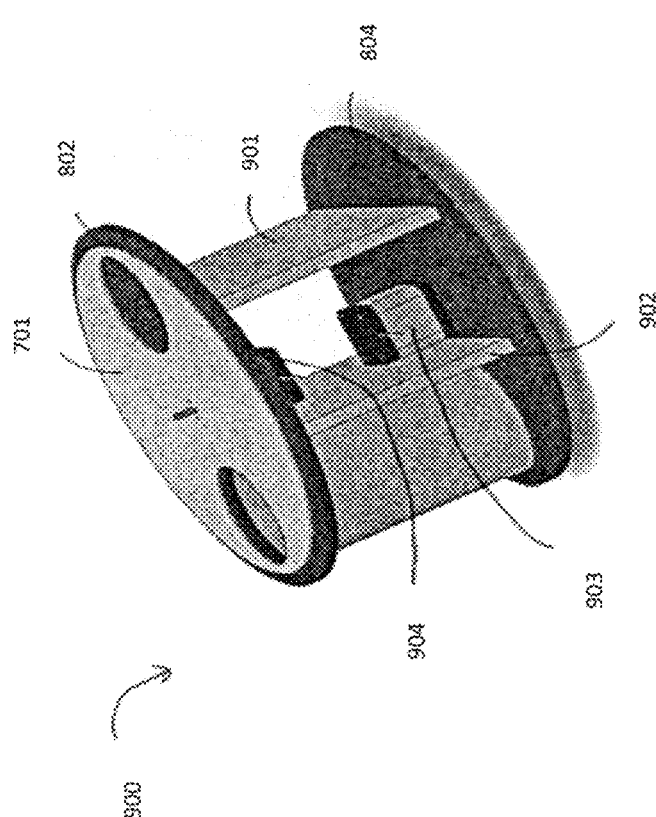

An example of the first embodiment is shown as device 500 of FIGS. 5-9. As shown in FIG. 8, the magnet 808 may be a magnetic disc. Magnet 808 is located within a tube 807, such as an aluminum tube, such that the magnetic field strength is maximal at the open ends of the tube. In the embodiment shown in FIG. 8, the magnet 808 is located approximately at the midpoint of tube 807. Revolving discs 701, 906 constructed of materials that reduce or block magnetic transmission, such as a metal such as steel or iron, can be positioned at either or both ends of the tube 807. Revolving disc 701 is located proximate to plate 802, and revolving disc 906 is located proximate to plate 804. In some embodiments, the revolving discs 701, 906 may contact plates 802, 804, while in other embodiments, there is no contact between the revolving discs and the plates. Supports 902, 901 extend between the plates 802, 804. If the tube 807 is oriented vertically, the revolving discs 701, 906 are oriented horizontally, above and below the open ends of the tube containing the magnet 808.

The revolving discs 701, 906 have a portion or portions absent thereby creating one or multiple holes or apertures 801, 905, allowing for less or no blockage of magnetic transmission. Specifically, plates 802, 804 includes plate apertures 805, 806 at the ends of tube 807. When an aperture 801 of revolving disc 701 overlaps with plate aperture 805 of plate 802, or when an aperture 905 of revolving disc 906 overlaps with plate aperture 806 of plate 804, the overlap of apertures 801, 905 and plate apertures 805, 806 allow for less or no blockage of magnetic transmission. The revolving discs 701, 906 can be spun about axis 803 at variable rates and the same or different directions, to produce intermittent magnetic pulsations of lesser and greater frequencies. The spinning of the revolving discs 701, 906 can also be synchronized to spin at the same rate, with the apertures 801, 905 in the discs aligned or unaligned. Revolving disc 701 is driven by motor 904, and revolving disc 906 is driven by motor 903. The motors 903, 904 may, for example, be stepper motors. Preferably, motors 903, 904 rotate revolving discs 701, 906 at the rates at which the stimulation of portions of the HEPS is desired, such as rates in the range of less than 1 Hz to about 40 Hz. Other portions of the HEPS can be stimulated at higher frequencies.

When the device 500 of the first embodiment (as shown in FIGS. 5-9) is used without moving magnet 808 (i.e. when magnet 808 is stationary), the device 500 does not create an electromagnetic or magnetic field. Instead, when magnet 808 is stationary, device 500 creates a stationary magnetic field that has a pulsed characteristic. The pulsed characteristic is created because the magnetic field appears and is blocked based upon the position of apertures 801, 905 of revolving discs 701, 906. As such, when the device 500 is used in proximity to a subject and magnet 808 is stationary, the magnetic field produced by the device does not generate a current in any tissue of the subject that it may overlap, unless the tissue is moving. Also, magnet 808 may have a low strength, such as 383 gauss at 1 inch due north and south of the magnet, or 3 gauss at 12 inches due north and south of the magnet, at either the top or bottom of the tube 807. When a low strength magnet is used, the level of magnetic overlap with a subject is quite small or non-existent, especially if the subject is located to the side of the tube 807, instead of in front of the top or bottom of the tube 807. Even if the magnetic field does overlap the physical body of the subject, the physical body would need to be in motion in order to generate an electric current when magnet 808 is stationary. Accordingly, while not intending to be bound by theory, when a stationary low strength magnet is used in device 500, the primary or sole cause of an effect on the subject may be conduction using the HEPS.

In a alternate embodiment of the present invention, the magnet may be rotated within the tube. The magnetic material may be surrounded by materials that condition the magnetic field, such as steel or iron, and/or directionally orient the magnetic field, such as aluminum. The magnetic field can then be influenced by moving materials in proximity to the magnetic field that provide variable impedance or blockage of the field to intermittently reduce or completely block the outward transmission of the magnetic field.

Figure 10:
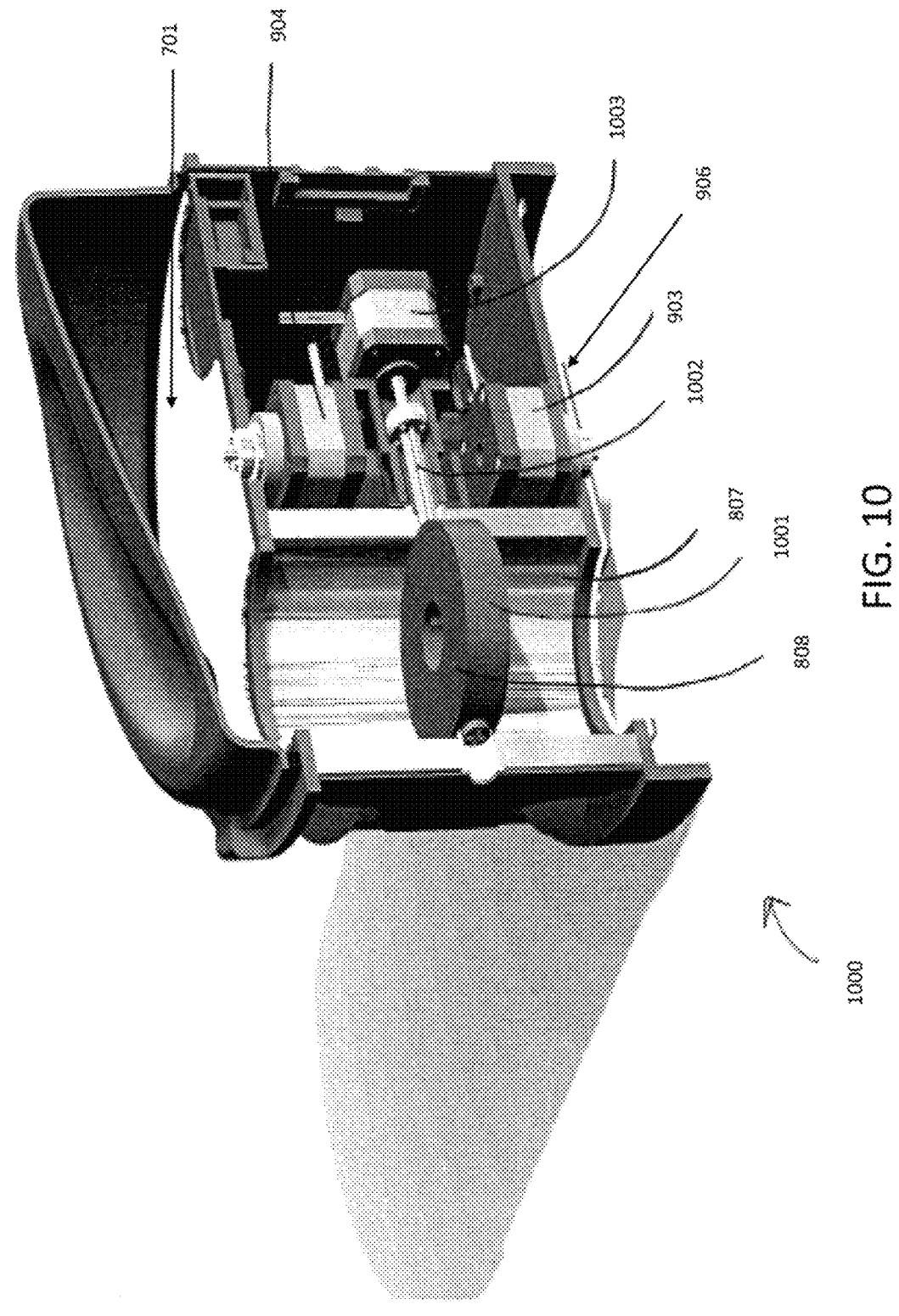
FIG. 10 depicts a diagram with a cutaway view of an alternate embodiment of the present invention.

FIG. 10 shows a cutaway view of device 1000, which is an example of the alternate embodiment. As is the case with device 500, magnet 808 of device 1000 is located within tube 807, such as an aluminum tube, such that the magnetic field strength is maximal at the open ends of the tube. In the alternate embodiment shown in FIG. 10, the magnet 808 is located approximately at the midpoint of tube 807. Revolving discs 701, 906 (as shown in FIGS. 5-9), constructed of materials that reduce or block magnetic transmission such as steel, iron, or other metals, can be positioned at either or both ends of the tube 807. As shown in FIGS. 5-9 revolving disc 701 is located proximate to plate 802, and revolving disc 906 is located proximate to plate 804. In some embodiments, the revolving discs 701, 906 may contact plates 802, 804, while in other embodiments, there is no contact between the revolving discs and the plates. If the tube 807 is oriented vertically, the revolving discs 701, 906 are oriented horizontally, above and below the open ends of the tube containing the magnet 808.

As discussed above in connection with device 500, the revolving discs 701, 906 of device 1000 include one or multiple holes or apertures 801, 905, allowing for less or no blockage of magnetic transmission. Plates 802, 804 includes plate apertures 805, 806 at the ends of tube 807. When an aperture 801 of revolving disc 701 overlaps with plate aperture 805 of plate 802, or when an aperture 905 of revolving disc 906 overlaps with plate aperture 806 of plate 804, the overlap of apertures 801, 905 and plate apertures 805, 806 allow for less or no blockage of magnetic transmission. The revolving discs 701, 906 can be spun about axis 803 at variable rates and the same or different directions, to produce intermittent magnetic pulsations of lesser and greater frequencies. The spinning of the revolving discs

701, 906 can also be synchronized to spin at the same rate, with the apertures 801, 905 in the discs aligned or unaligned. Revolving disc 701 is driven by motor 904, and revolving disc 801 is driven by motor 903. The motors 903, 904 may, for example, be stepper motors. Preferably, motors 903, 904 rotate revolving discs 701, 906 at the rates at which the stimulation of portions of the HEPS is desired, such as rates in the range of less than 1 Hz to about 40 Hz. Other portions of the HEPS can be stimulated at higher frequencies.

Device 1000 also includes a motor 1003 for moving magnet 808. Motor 1003 is connected to shaft 1002, which is connected to an assembly 1001 that surrounds, and is attached to, magnet 808. Motor 1003 drives shaft 1002, which acts on assembly 1001 to swivel or rotate the assembly and, therefore, to swivel or rotate magnet 808. Therefore, magnet 808 can be rotated within the tube 807 to produce either greater or lesser magnetic field strength at the openings of the tube. This embodiment may be used to maximize or minimize field strength coincident with the peak frequency stimulation of the high frequency (HF) band, the low frequency (LF) band, either or both or other bands, alone or in combination, such as the very low frequency (VLF) band. It is also possible to have the magnetic field strength oscillate to match different sleep stages within the ultradian rhythm. The HF band, LF band, VLF band and ultradian rhythm are discussed below. In this embodiment, device 1000 has the capability of changing or oscillating magnetic field strength, independently or in concert with masking and unmasking the magnetic field at different frequencies. The change of magnetic field strength is programmable.

In another embodiment of the method of the present invention, a low strength static magnetic field, emanating from an earth magnet (not an electromagnet), masked and unmasked alternately at frequencies at or below approximately 20 Hz, and positioned approximately 1 foot beneath or below the user's feet, facilitates the induction and maintenance of light, deep (delta or slow wave) and REM (dream) sleep, depending upon the frequency of masking and unmasking the magnetic field. This method may be accomplished using device 500 of FIGS. 5-9 or device 1000 of FIG. 10. The strength of the magnetic field is fixed by the strength of the earth magnet, which does not exceed approximately 3 Gauss or 0.0003 Tesla, at 1 foot from the magnet.

The end user can select a protocol using the associated computer or mobile application, which dictates the duration and sequences of frequencies of masking and unmasking the magnetic field, as well as the overall duration of an intended sleep period. With focus on the connection for the computer or mobile application to the device, a wireless link is used configured to deliver data as an IoT (Internet of Things) server.

The IoT is defined as a network of physical devices and other items embedded with electronics, software, sensors, actuators, and network connectivity which enable these objects to collect and exchange data. Communication with surrounding IoT devices is, therefore, important for increased functionality (e.g. the ability to cause action of IoT actuators) and situational awareness (e.g. the ability to access data from remote sensors). A single communication standard for IoT has not yet coalesced. The most popular wireless communication/transport layers currently in use by IoT devices include Bluetooth; IEEE 802.11 based Wi-Fi communication. multiple low-rate wireless personal area networks (LR-WPANS) based on IEEE 802.15.4 including ZigBee, MiWi, and Wireless HART. Near field communications (NFC) protocol based on ISO/IEC 18092, cellular. IEEE 802.16 based WiMAX communication. These common standards are herein incorporated by reference in their entirety. IoT devices may use IPv6 internet layer protocol for packet-switched networks to deliver messages over one of the communication/transport layers listed previously in a variety of formats. Message Queuing Telemetry Transport (MQTT) protocol is a publish/subscribe messaging model that may be used to deliver data within this framework. MQTT is a popular IoT option because of its a small code footprint and limited network bandwidth needs. Other alternatives are available and may be used based on the data rate, communication range, and power consumption requirements of a particular IoT device.

The National Institute of Health reports that more individuals are moving to home healthcare. It is anticipated that this is especially true of users and will necessitate the transmission and/or storage of healthcare data on user devices. In some embodiments, wireless devices may be integrated with an and a user's health data may be sent over wireless networks. Health data may include one or more of user medical data and/or data items, such as raw sensor data, conclusions data, patient measurements, weight, temperature, heart rate, pulse, respiratory rate, blood pressure, wetness, sight, hearing, reaction time, pain status, emotional state, orientation, location, event, state, and action. Wireless devices used on or in connection with the herein may communicate using one or more of cellular, 802.11, Wi-Fi, 802.15, Bluetooth, Bluetooth Low Energy (BLE), 802.20, WiMAX, or other wireless communication standards or methods. For this type of service or application, certain standards will need to be upheld to protect user identity, security, and data. One such standard is the Health Insurance Portability and Accountability Act (HIPPA). HIPAA sets the standard for protecting sensitive user data. Any product or service that deals with protected health information (PHI) must ensure that all the required physical, network, and process security measures are in place and followed. This includes covered entities, anyone who provides treatment, payment, and operations in healthcare, and anyone with access to patient information and provides support in treatment. Subcontractors and business associates must also be in compliance with HIPAA.

The HIPAA Privacy Rule addresses the saving, accessing, and sharing of medical and personal information of any individual, while the HIPAA Security Rule more specifically outlines security standards to protect health data created, received, maintained, or transmitted electronically, also known as electronic PHI (ePHI). Anyone hosting ePHI data with a HIPAA compliant hosting provider must have certain administrative, physical, and technical safeguards in place, according to the U.S. Department of Health and Human Services. The physical and technical safeguards are most relevant to services provided by the HIPAA compliant host as listed below, with detail on what constitutes a HIPAA compliant data center.

Physical safeguards include limited facility access and control. All HIPAA compliant entities must have policies about use and access to workstations and electronic media. This includes transferring, removing, disposing, and re-using electronic media and ePHI. Technical safeguards require access control to allow only authorized personnel to access ePHI. Access control may include the use of unique user IDs, biometric login, authentication, emergency access procedures, automatic log off, and encryption and decryption, among others.

Audit reports and tracking logs should be implemented to track activity on hardware and software. These reports are useful in pinpointing the source(s) of any security violations or failures. Technical policies may also cover integrity measures put in place to confirm that ePHI has not been damaged. It is important to have Information technology (IT) disaster recovery and offsite backup measures in place to ensure that any electronic media errors or failures can be repaired and ePHI can be recovered accurately and intact.

Network security is another technical safeguard required of HIPAA compliant hosts to protect against unauthorized access of ePHI from methods of transmitting data, including Internet and private networks. Use of secure connections is required to support the secure storage and secure transmission of personal health data. A supplemental act was passed in 2009 called The Health Information Technology for Economic and Clinical Health (HITECH) Act which supports the enforcement of HIPAA requirements by raising the penalties of health organizations that violate HIPAA Privacy and Security Rules. The HITECH Act was formed in response to health technology development and increased use, storage, and transmittal of ePHI.

Countries, companies, and individuals around the world are looking for better ways to monitor health data as a growing percentage of the population is requiring medical care, both because of the changing demographics and the incidence of long-term chronic disease. This is reflected in a growing demand for connected health devices where user data can be collected by medical institutions and/or by individuals. As the use of these devices increases, along with the volume of data produced, it becomes increasingly important to ensure interoperability between devices so that similar devices connect and transfer data in a standard way.

Health device manufacturers may use Bluetooth wireless technology for a secure and reliable connection. Until recently, Bluetooth technology, as defined in the Bluetooth Core Specification, provided a wireless link, but underlying data protocols and formats were proprietary. Agreement was lacking over the best profile on which to base these underlying layers. Most devices used serial port profile (SPP) to emulate a standard RS-232 (EIA-232) serial cable, but DUN, FAX, PAN, and HID have also been put to use. In order for a consumer mass market in health and fitness devices to evolve, an interoperable wireless standard was needed.

The Bluetooth Special Interest Group (SIG) established a Medical Devices Working Group (MED WG). This group developed a profile to provide for interoperability between health devices and data sources (such as blood pressure meters, weighing scales, and thermometers) and health device sinks (such as personal computers (PCs), personal data assistants (PDAs), mobile phones, tablets, wearable computing devices, and displays) from different manufacturers. The Health Device Profile (HDP) and the Multi-Channel Adaptation Protocol (MCAP) together fulfill this need. The Bluetooth HDP defines the underlying wireless connection and protocol. It operates in conjunction with the ISO/IEEE 11073-20601 Personal Health Data Exchange Protocol (PHDEP) and associated device specialization specifications to provide application level interoperability for a wide variety of personal health devices. The Bluetooth Core Specification and ISO/IEEE 17073-20601 are herein incorporated by reference in their entirety.

Bluetooth Low Energy (BLE) was introduced in the Bluetooth 4.0 core specification by the Bluetooth SIG. It provides low energy demand, low bandwidth communication and is widely adopted by internet of things sensors and devices. Bluetooth Low Energy is an extremely flexible framework that can enable open broadcasting of data (beacon functionality) and developer configuration. It is less mature than classical Bluetooth. The Generic Attributes (GATT) define a common data structure that is exposed to connected BLE devices. While the HDP and MCAP are not incorporated in BLE, methods and services have been incorporated into GATT which support the transmission of ePHI, such as heart rate and temperature. When configured as a point-to-point device (i.e. not broadcasting), encrypted, and using GATT, a BLE connection provides application level interoperability for a wide variety of person health devices. For the purpose of this disclosure, unless explicitly stated, the term Bluetooth is meant to generically encompass classical or low energy Bluetooth embodiments.

Back now to the configuration, the duration and sequences of frequencies of masking and unmasking the magnetic field may be modified algorithmically, in real time, by the apparatus of the present invention. This is accomplished using real time data transmitted from an activity and pulse rate variability monitor worn on the end user's arm or leg, based upon a comparison of the user's real time data to any existing user-stored physiologic data, considering preset adjustment parameters.

For example, a sequence of frequencies of masking and unmasking the magnetic field may be programmed for induction of sleep. The frequencies may be oscillated between alpha, theta and delta and then back to theta frequencies in a pattern that does occur normally, such as the following pattern: alpha 10 Hz-theta 5 Hz-delta 2 Hz-theta 6 Hz.

In a another embodiment of the present invention, motion can be applied to magnetic materials directly by creating a system of magnetic materials with a mechanism applying a time varying force. That system in total can then be affected by another mechanism applying separate and different time varying forces to it, thereby creating a more complex magnetic waveform of various frequencies, because of the varying magnetic motion and so on.

Figure 11:
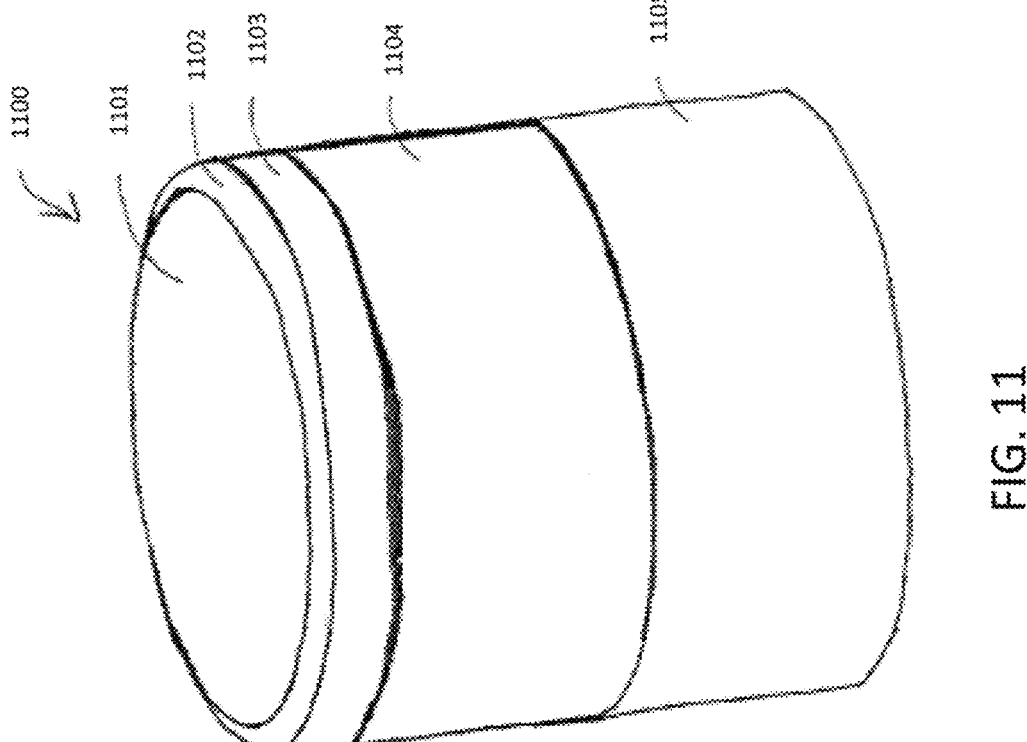
FIG. 11 depicts a diagram of the alternate embodiment of the present invention.

An example of this embodiment of the present invention is shown as device 1100 in FIG. 11. In this embodiment, a movable magnet 1101, such as a magnet in the form of a magnetic disc, can be affixed to a flexible sheet 1102, such as a flexible silicon sheet or something similar, with a partial air-filled bladder or bellows 1103 affixed below the magnet 1101. The air-filled bladder or bellows 1103 can be dynamically pressurized causing it to be less or more compliant. A force impacting the bladder or bellows 1103 at a fixed or variable frequency with a force pattern resembling a sine, sawtooth or square wave will thereby create an amplitude of magnetic movement that is either greater or less, depending upon the compliance of the bladder or bellows.

In this embodiment, a second air-filled bladder or bellows 1104 rests underneath the system described above. This second air-filled bladder or bellows 1104 can also be dynamically pressurized causing it to be less or more compliant. A force impacting the second bladder or bellows 1104 at a fixed or variable frequency with a force pattern resembling a sine, sawtooth or square wave will thereby create an amplitude of magnetic movement that is either greater or less. This resultant motion will move both the movable magnet 1101 and the upper bladder or bellows 1103. Alternatively, the mere pressurizing and depressurizing of the second bladder or bellows 1104 can act to move the movable magnet 1101. This second motion mechanism is intended to provide motion that is higher in amplitude than the first air filled bladder or bellows 1103.

In this embodiment, an alternate air-filled bladder or bellows 1105 acting upon the second bladder or bellows 1104 can further influence the magnetic motion and resultant waveform and so on. Alternatively, an additional force impacting the second bladder or bellows 1104 at a fixed or variable frequency with a force pattern resembling a sine, sawtooth or square wave will thereby create a further variant of the magnetic movement.

When the device 1100 of the embodiment (as shown in FIG. 11) is used, the movable magnet 1101 is put into motion. Therefore device 1100 can generate an electromagnetic field or magnetic field emanating one frequency or many. Although not intending to be bound by theory, the device of this embodiment may affect subjects in proximity to the device because the electromagnetic or magnetic field may generate current in the cells that surround the nerves of the subject. This current can be conducted into the spinal cord and farther up into the brain, assuming that the magnetic field is large enough to overlap the physical body of the subject. Although not intending to be bound by theory, the device of this embodiment may also affect subjects due to the stimulation of the subjects' HEPS.

The 0.25 Hz stimulus was originally selected due to a clinical study published in 2016 demonstrating a decreasing respiratory rate variability with increasingly deeper stages of sleep, but in all stages of sleep and during wakefulness, the respiratory rate was approximately 15 breaths per minute or approximately 0.25 Hz. Respirations produce a weak fluctuating electromagnetic field due to the body's electromagnetic field, which can interact with the Earth's magnetic field and thus the motion caused by respirations can create magnetic micro-pulsations of 0.25 Hz. One of our sensitive observers noted stimulation of the energetic structure identified as the 10th chakra, below the feet, when we subjected it to magnetic pulsations of approximately 0.25 Hz. Of interest, in certain traditions, this structure is termed the spiritual lung and is believed to be the pathway or connection for the incoming spiritual energy of the individuated spiritual self. It is postulated by some that this spiritual energy is also the source of healing. In our experience, physical and emotional healing has been facilitated by greater spiritual integration with the physical body.

To create the greater likelihood of brainwave entrainment or at least a partial entrainment effect, it is necessary to use extremely low frequency (ELF) stimulation, as brainwaves range from about 0.1 Hz to 35 Hz. Using permanent magnets as part of a system to generate these low frequencies avoids the excessive heat that develops with electromagnetic coils resulting from the low resistance and high current within coils at these low frequencies. Therefore, creating magnetic ELF frequencies, without low frequency modulation of higher frequencies to avoid over-heating, is accomplished by either motion of a permanent magnet (using a device such as device 1100 discussed above) or intermittent masking and unmasking of its magnetic field (using a device such as device 500 discussed above). In this manner, the ELF frequencies produced, add to the local ELF micro-pulsations that are normally present in the Earth's magnetic fields, present local to the site of stimulation. Of note, the most prevalent magnetic micro-pulsation frequency in the Earth's magnetic fields, in the ELF range, is measured to be approximately 10 Hz, which also happens to be the dominant EEG frequency found in man, revealing the likelihood that mankind, which evolved in the Earth's magnetic field, is sensitive to and has adapted accordingly to these natural influences.

Following some time during which a person is stimulated at approximately 0.25 Hz to enhance their level of energetic presence throughout their physical body and thus their degree of conductivity throughout the physical body, their Hara line below their feet, or presumably, their energetic self at any location, can be stimulated with a magnetic frequency that matches the desired brainwave state to be achieved or approximated. Stimulation of their energetic self in this manner would cause entrainment of the frequency through-out their energetic self. The energetic entrainment would then entrain the DC current in the perineural system, to the extent possible, throughout the body. That entrained current would be conducted towards the brain via the perineural system as well as directly to the brain via the energetic self and ultimately produce brainwave frequencies matching or approaching the original stimulus, depending upon any resistances encountered to propagate the original signal. In addition, the perineural system of the brain itself can be similarly stimulated and entrained to the extent possible.

The ability to magnetically stimulate the energetic self without stimulating the physical body requires that the magnetic stimulus is confined to the stimulating device by a shielding mechanism or structure that blocks the spread of the magnetic field yet remains permeable to the energetic self. Without such a shielding mechanism, the magnetic field will overlap the physical body, but at a level of reduced field strength.

If a large enough stimulating magnetic field overlaps aspects of the physical body with its respective perineural system, then that part of the perineural system will also be entrained directly, thus producing similar or additive results. In either instance of the stimulating magnetic field not overlapping or overlapping the physical body, some level of entrainment of the nervous system can also be accomplished at ELF frequencies without prior stimulation at approximately 0.25 Hz.

These methods allow for brainwave entrainment, to the extent possible, which produces various states of conscious-ness and different stages of sleep. Entrainment to deeper stages of sleep, such as delta or slow wave sleep will be dependent upon the subject's age and condition. With repeat exposure to the entraining stimulus, it is anticipated that greater degrees of entrainment will result.

Users of such an invention can experience the non-sleep, altered consciousness states, to the extent that they remain consciously aware and then could learn how to self-induce these states, after some level of training or conditioning. Or, if incapable of self-inducing them, could more readily re-experience these, as well as the sleep states, using such a system, whenever needed or desired.

In an invention that is designed to modify brainwaves, brain states, or states of consciousness, including sleep, relaxation, meditation, hypnosis and healing, it is conceiv-able that having data related to those measurements or states could be helpful in tailoring or modifying the stimulus to achieve a desired result. If for instance, EEG or other physiologic monitoring was performed in conjunction with the stimulus, a feedback control could be instituted allowing for changes to be made to the stimulus based upon the monitored or measured results and the desired result. This feedback control mechanism could assist in more directly achieving the desired goal, whether it be a particular stage of sleep, state of consciousness or related situation or assist in determining the duration of any particular stimulus, based upon the results achieved. The feedback control may be used in connection with any device of the present invention, including devices 500, 1000, or 1100 discussed above. The physiologic monitoring may be performed using wearable devices (such as watches from such companies as Garmin Ltd., Polar Electro Oy, Fitbit, Inc., Apple Inc., etc.), or other devices that measure heart or pulse rate and variability with or without respiratory data for a number of applications—sleep, meditation, relaxation, and many related medical or psychological conditions.

It is anticipated that the magnetic stimulation pattern that can be used in conjunction with such EEG or other physi-ologic feedback that predicts the dominant EEG frequency, could be matched to that dominant EEG frequency and then gradually modified to more effectively cause a change to the dominant EEG frequency, since the change that is being induced would be minor. In such a situation, it is also anticipated that other complementary stimuli, in conjunction with the magnetic stimulation, would also be supportive in causing the desired changes. These complementary stimuli would include, heat, light, sound and vibration. The inven-tion can include a light source, sound emitter, and a means of creating physical vibration that the user can experience to facilitate a faster transition to a different brain state or state of consciousness. The light source, sound emitter, and/or means of creating physical vibration may be used in con-nection with any of the embodiments discussed above, such as devices 500, 1000, or 1100.

As discussed above, in accordance with the present inven-tion, magnetic stimulation in the range of brainwave fre-quencies may be used to create entrainment of brainwaves. However, although those frequencies are helpful in creating entrainment using the appropriate stimuli that travel via the actual sensory nerves that convey light, sound and touch (vibration), they may not be the best frequencies to use for magnetic stimulation, particularly if that magnetic stimula-tion is expected to be conveyed via traditional nerve impulses derived from action potentials—firing of the nerves (as opposed to travelling on the surface of nerves, the myelin sheath comprising the DC perineural system). Also, of note, even though the frequencies of those stimuli (visible light, audible sound and vibrations higher than 40 Hz or so) are higher in frequency than brainwaves, those stimuli can be amplitude modulated to simulate lower frequencies in the range of brainwaves to effect changes in brainwaves when those stimuli are conducted via traditional sensory nerves.

It certainly is conceivable that the DC perineural system can convey magnetically-induced frequencies in the range of brainwave frequencies (especially the lower frequencies in the delta frequency range), which we presume it can do. However, it is suggested that lower frequencies, below 0.5 Hz, may play an even more significant role in triggering changes in brainwave patterns (frequencies) and that this mechanism may be a more natural means of causing shifts in brainwave frequencies, particularly during sleep. The system, underlying this mechanism, has evolved over mil-lennia and is already in place to serve this function.

Phylogenetically, from an evolutionary standpoint, the DC perineural system and somatic nerves defining the peripheral nervous system evolved first followed by the rudimentary autonomic nervous system (ANS) and ulti-mately the spinal cord, brainstem with cranial nerves and finally the cerebrum. Therefore, the ANS was an outgrowth of the DC perineural and peripheral nervous system, and as such, was/is greatly influenced by it. Furthermore, the ANS regulates our organ's functions and basic bio-rhythms, including sleep, so it should be no surprise to see tremen-dous interaction between activity conducted via the DC perineural system and sleep.

Figure 12:
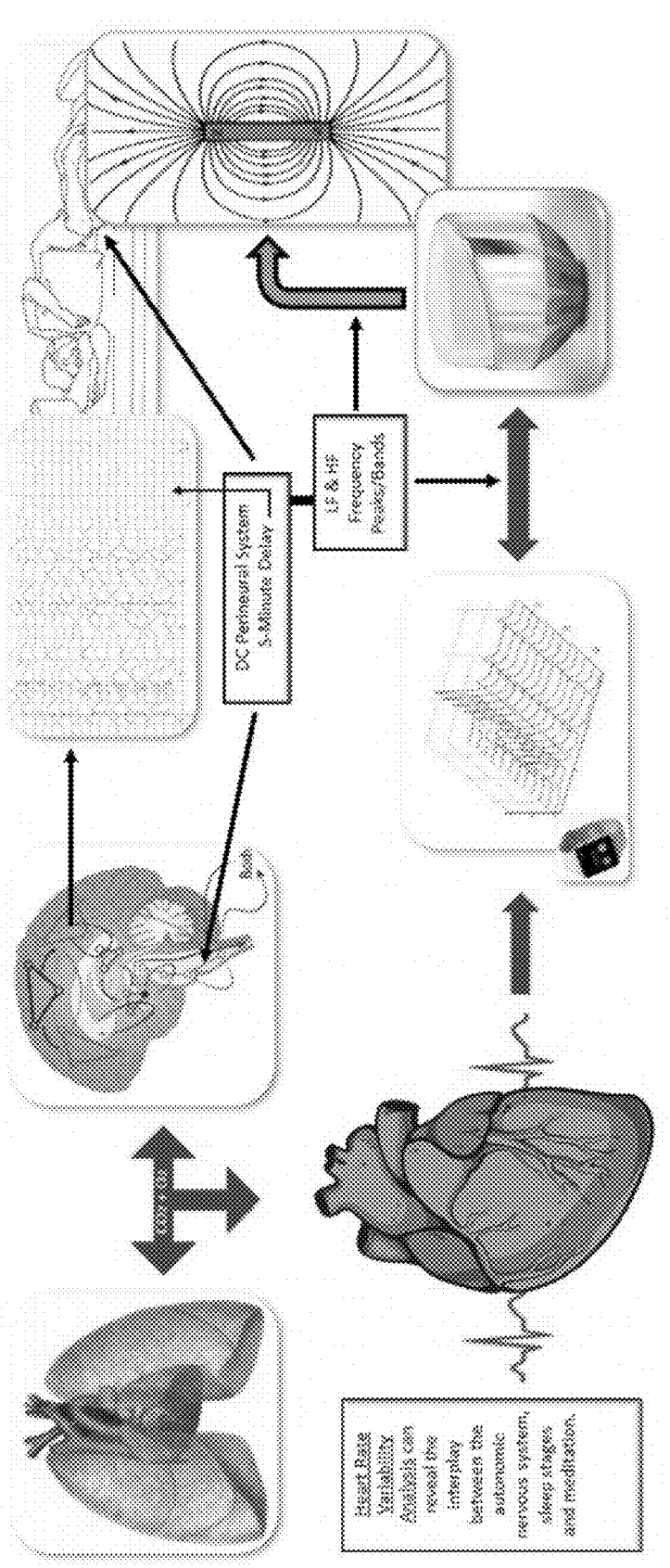
FIG. 12 depicts a diagram of a low frequency stimulation system in accordance with alternate embodiment of the present invention.

The diagram shown in FIG. 12 illustrates this low fre-quency stimulation system. This system is a normal feed-back loop between certain aspects of the autonomic nervous system (ANS) receiving feedback from sensors in bodily tissues and organs, which then influence more rostral (frontal) regions of the brainstem (hypothalamus and thalamus), which then affect the cerebral hemispheres, reflected in the ensuing brainwave changes. We believe this system can be influenced by the DC perineural system throughout the body, as the frequencies used in both the ANS and DC perineural system are so similar.

Mechanical and neural stimulation related to respiration (the act of breathing) affects heart rate and rhythm via mechanical changes directly as well as chemoreceptors (measuring pH and oxygen levels) in the brainstem and elsewhere in the body. This rhythmic activity is considered normal and is called respiratory sinus arrythmia or normal sinus rhythm. Normally, during inspiration, the heart rate increases and during exhalation, the heart rate decreases. These rhythmic changes parallel the respiratory rate and are primarily controlled by the parasympathetic division of the ANS.

Another reflex, the baroreceptor reflex, originates from pressure sensors in the aortic arch and carotid arteries, which measure blood pressure changes. Baroreceptor inputs also cause changes in the heart rate in an effort to provide adequate blood pressure and flow to circulate oxygen, carbon dioxide and nutrients. These changes are controlled by both the sympathetic and parasympathetic divisions of the ANS.

These two functions—respiration and circulation—are two of the most basic functions of life and require automatic, subconscious regulation, relegated to the ANS.

Baroreceptor influences create neurologic impulses carried in autonomic nerves and some cranial nerves that have been measured at frequencies approximating 0.1 Hz. This very low frequency waveform is named Mayer's waves in honor of one of the scientists making this discovery. The respiratory influences also create neurologic impulses carried in similar nervous pathways at frequencies that are a bit faster, typically between 0.2 Hz and 0.3 Hz, consistent with the respiratory rate. These frequencies are clearly below traditional EEG frequencies, but are certainly in the range of, and can be conveyed by, the DC perineural system.

When heart rate is measured and analyzed for its variability (heart rate variability or HRV) in the frequency domain, two or more peaks may emerge: one around 0.1 Hz and another around 0.26 Hz, with individual variability. Scientific committees, in an attempt to create standards around HRV analysis and reporting, have defined two major frequency bands, low frequency (LF band=0.04 Hz to 0.15 Hz) and high frequency (HF band=0.15 Hz to 0.4 Hz) and a minor band, very low frequency (VLF band=0.003 Hz to 0.04 Hz). Researchers have tended to analyze HRV data accordingly and often report trends in these bands and their ratios coincident with other physiologic states.

Research in HRV in the frequency domain exploded in the 1970's due to the creation of Fourier analysis and the Fast Fourier Transform. Due to the development of lower cost integrated circuits, the time-based, and to a lesser extent, the frequency-based analysis and reporting of HRV, has more recently been incorporated into many consumer product offerings, intended to assist individuals with their exercise routines and other wellness practices. For example, HRV is reported on many different wearable watches for these purposes. In addition, HRV metrics have been shown to provide a reasonable estimate of sleep stages, at present, mainly for consumer applications.

In the scheme depicted in FIG. 12, results from HRV analysis can be obtained in real time, particularly the power spectral density of the HF and LF bands and their peak frequencies when analyzed in the frequency domain. This information can then be used to guide the stimulus parameters associated with a device of the present invention (such as device 500, 1000, or 1100), which is depicted by 1201 in the diagram of FIG. 12.

As discussed above, a wearable device (such as a watch from such companies as Garmin Ltd., Polar Electro Oy, Fitbit, Inc., Apple Inc., etc.), or any device that measures heart or pulse rate variability (HRV or PRV), may be used as a feedback device in connection with the magnetic stimulation devices of the present invention, such as devices 500, 1000, or 1100. The present invention also encompasses the use of a wearable device as a feedback device for Pulsed Electromagnetic Therapy (PEMF therapy) devices, for the purpose of indicating, guiding or causing the frequency or amplitude stimulus to be modified. HRV or PRV measures frequencies in the range of 0 to 0.5 Hz. PEMF devices cannot create pure signals at those low frequencies due to Ohm's Law, because running a current through wires at these low frequencies creates extremely low resistance such that they overheat and melt or burn. However, PEMF devices can amplitude modulate (at extremely low frequencies) a higher frequency signal that avoids that limitation.

Figure 13:
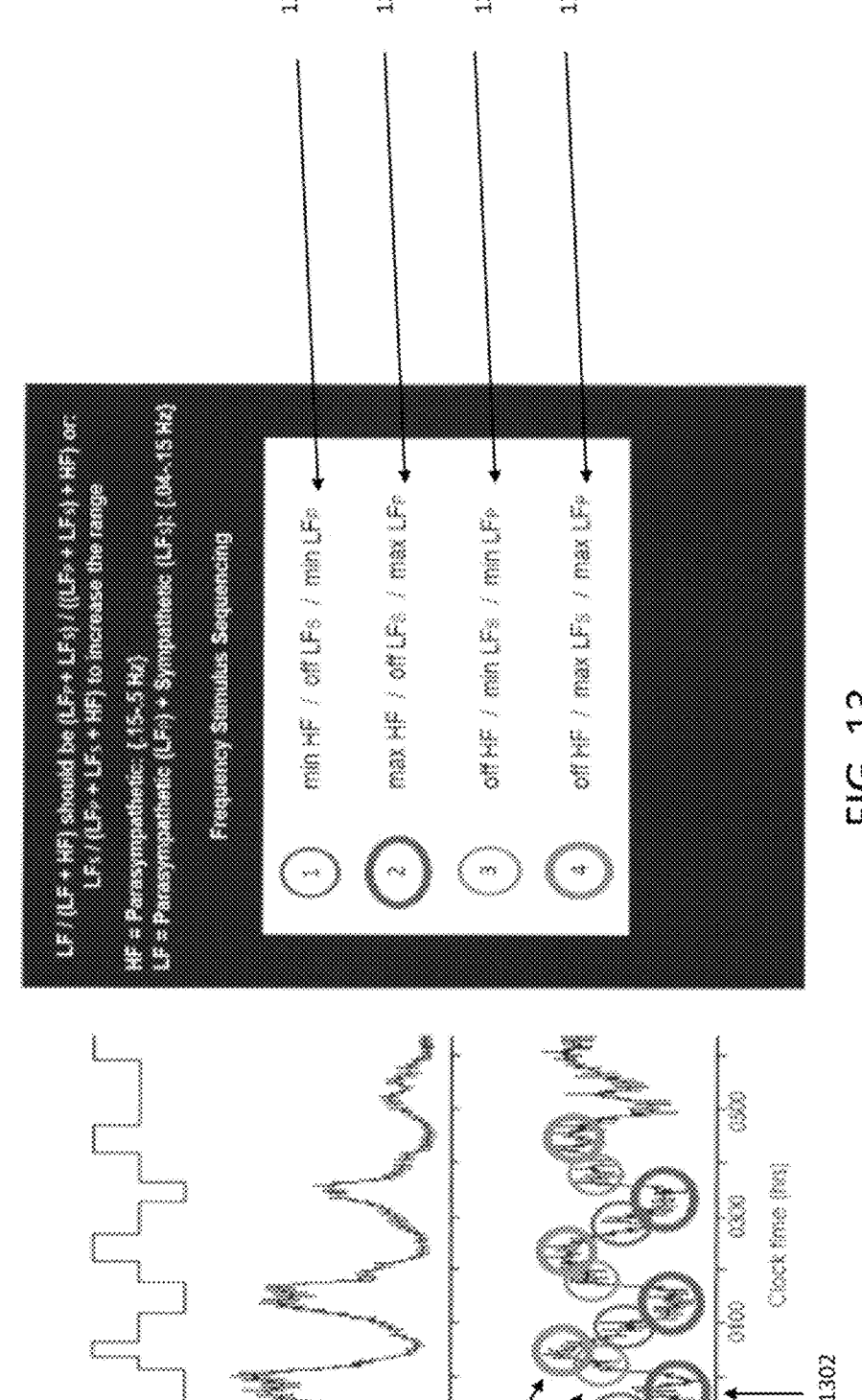
FIG. 13 depicts graphs that show a sleep histogram, delta activity and the LF/(LF+HF) ratio, wherein LF is the low frequency band and HF is the high frequency band.

The chart in FIG. 13 (depicting the sleep histogram, delta activity and the $$\frac{LF}{LF + HF}$$

ratio, without the superimposed circles) is from a study performed in 2001—"Inverse coupling between ultradian oscillations in delta wave activity and heart rate variability during sleep," authored by Gabrielle Brandenberger, Jean Ehrhart, Francois Piquard, and Chantal Simon and published in Clinical Neurophysiology 112 (2001) 992-996 ("Brandenberger et al.").

The chart of FIG. 13 illustrates the inverse relationship between the brain's delta activity and the $$\frac{LF}{LF + HF}$$

ratio during sleep. Furthermore, cited in the results of Brandenberger et al. was the finding that cardiac changes preceded EEG changes by about 5 minutes. Although not commented on by the investigators, the importance of this 5-minute delay should not be understated. It reinforces the knowledge that sleep stages are regulated by primitive autonomic brainstem mechanisms, which are conditioned by autonomic feedback loops, accounting for the 5-minute delay. Therapeutically, these feedback mechanisms, presumably can be enhanced or modified by magnetic stimulation utilizing the DC perineural system, which can then reinforce, entrain and/or normalize and/or enhance sleep stage patterns and depth, as well as potentially normalize sleep cycles and ultradian rhythms.

Based upon the information (HRV band power, frequency peaks and ratios) provided by measuring and analyzing in real time the HRV data from the user, magnetic stimulation using these or similar frequencies (magnetic stimuli from a device of the present invention, such as device 500, 1000, or 1100, travelling up the DC perineural system), can modify the feedback mechanisms, thereby changing the inputs to the hypothalamus and thalamus, ultimately affecting sleep stages and cycles, the cerebral hemispheres and resulting brainwave patterns reflective of different stages of sleep. Similarly, this mechanism can be used to induce different states of consciousness and alertness, enhancing stress reduction, relaxation, meditation, hypnosis, the treatment of insomnia and other psychological conditions and symptoms and healing.

The circles and ovals (1301-1304) in the diagram of FIG. 13 illustrate a stimulation pattern intended to reinforce or enhance the normal sleep stages depicted in the chart. This presumes three frequency peaks are identified in the frequency analysis, including two in the LF band, one of which is believed to be associated with sympathetic and the other parasympathetic, activity. Normally, only two peaks are identified, simplifying the formula and the therapeutic intervention.

The chart of FIG. 13 shows the normal ultradian rhythm that occurs during sleep (and waking)—the normal sleep cycle oscillations. The first cycle (onset of sleep until the end of the first REM period) in humans typically ranges from 70 to 100 minutes and subsequent cycles (end of preceding REM period to the end of current REM period) range from 80 to 110 minutes. The major drive for sleep occurs due to our need to rest and physically restore ourselves, which occurs mainly during slow wave sleep (high delta activity). As can be seen in the chart, the drive for delta sleep diminishes with subsequent cycles, demonstrated by lesser amounts and duration of delta activity. REM sleep (dream sleep) emerges more significantly as the night progresses.

As discussed above in connection with the embodiment shown in FIG. 10, magnet 808 can be rotated within the tube 807 to produce either greater or lesser magnetic field strength at the openings of the tube. This embodiment may be used to maximize or minimize field strength coincident with the peak frequency stimulation of the high frequency (HF) band, the low frequency (LF) band, either or both. It is also possible to have the magnetic field strength oscillate to match the ultradian rhythm of sleep or selected aspects of the sleep cycle or stages of sleep. In this embodiment, device 1000 has the capability of changing or oscillating magnetic field strength, independently or in concert with masking and unmasking the magnetic field at different frequencies. The change of magnetic field strength is programmable.

It is anticipated that there may be a difference in effect of magnetic stimulation depending upon the subject's geographic location, northern or southern hemisphere or thereabouts, and the north-south orientation of the permanent magnet used in the stimulation. Therefore, the ability to switch the polarity of the magnet (such as the magnet of devices 500, 1000, or 1100) is provided. In addition, it is anticipated that the frequency of the magnetic stimulation not be fixed at exactly the same frequency for a duration that produces sustained resonance of molecules, cells or organs, but particularly ions within the stimulus field. To avoid such a circumstance, it is necessary to regularly vary the magnetic frequency, either around the target frequency or simply make frequent or regular frequency adjustments. This is particularly important when the oscillating magnetic field is parallel to the Earth's magnetic field.

It is also anticipated, that an embodiment of the magnetic masking and unmasking invention (such as device 500 or 1000 discussed above) will utilize various metallic structures, composed of various substances, to achieve the desired results. As such, different metals have different properties, some of which are capable of propagating a magnetic field, and can be combined to create different alloys, all of which are very likely to modify the magnetic field characteristics differently, accounting for different effects. Therefore, this invention anticipates the use of different metallic substances, with other potential additives as well, to achieve different results and to be able to use or swap multiple structures containing different metals and substances in the invention. Such a structure would be one or more revolving discs, such as revolving discs 701, 906, with alternating solid and porous portions that masks and unmasks the magnetic field, respectively.

Another additive, of a non-structural or material basis, is the addition of symbolic representations, imprinted or adorning the metallic structures. It is further anticipated that the magnetic field unmasking aspect of the metallic structure, which can simply be a circular hole, such as apertures 801, 905, may also be formed using different shapes or be the shape of various symbols, that may be more meaningful to the user. In order for the user to be able to see such representations, it is anticipated that the enclosing structure of the invention be made of a clear material, allowing the user to visualize the operating mechanism of the invention, including any symbolic representations, which may be present.

The present invention is also believed to confer healing capabilities for a broad range of illnesses and conditions, stress-related and non-stress-related. As such, it can be combined with many other healing modalities and practices to deliver amplified results. The present invention, in combination with a device which provides synchronized sound, vibration, magnetic and electromagnetic frequencies, such as the device described in U.S. Pat. No. 9,949,004, confers additional healing effects. An example of a device which provides synchronized sound, vibration, magnetic and electromagnetic frequencies is the SolTec® Lounge, which is available from Round River Research Corporation of Eden Prairie, Minnesota, United States. When using a device of the present invention (including devices 500, 1000, and 1100) in combination with the SolTec® Lounge, the music played in connection with the SolTec® Lounge may be amplitude modulated in order to generate frequency stimulation of the music, vibration and magnetic frequencies below 20 Hz.

The phenomenon of sleep or at least a state resembling sleep, first appears in certain species of fish and has progressively become a more complex phenomenon in higher animal species. In mammals, particularly human beings, sleep has been studied extensively in laboratory settings, resulting in an appreciation that mammalian sleep is comprised of cyclical state changes that can be documented through standard scientific measurement techniques.

The first widely accepted classification of different stages of sleep was first published in 1968 (Rechtschaffen A, Kales A, eds. A manual of standardized terminology, techniques and scoring system of sleep stages in human subjects. Los Angeles: Brain Information Service/Brain Research Institute, University of California, 1968). On the basis of these scoring rules (R&K), sleep recordings are divided into 7 discrete stages (wake, stage 1, stage 2, stage 3, stage 4, stage REM, and movement time). This scoring system is based upon measurements taken during polysomnography, which typically measures the electroencephalogram (EEG), electro-oculogram (EOG), electromyogram (EMG) of the chin and legs, electrocardiogram (EKG), blood oxygen saturation, respiratory activity (respiratory flow and effort), and sometimes other measurements as well.

Almost 40 years later, the American Academy of Sleep Medicine (AASM) modified the standard guidelines for sleep classification by Rechtschaffen and Kales and developed a new guideline for terminology, recording method, and scoring rules for sleep-related phenomena. (Iber C, Ancoli-Israel S, Chesson A, Quan SF, eds. The AASM manual for the scoring of sleep and associated events: rules, terminology, and technical specification, 1st ed. Westchester, IL: American Academy of Sleep Medicine, 2007.). In summary, the major changes of the new manual comprise EEG derivations, the merging of Stages 3 and 4 into N3 (N1=Stage 1, N2=Stage 2), the abolition of the stage "movement time," and the simplification of many context rules.

It should be noted that the primary measurements used in determining sleep and its' stages are generally limited to the analysis of EEG, EOG and chin EMG measurements. The structures of the nervous system that directly manifest EEG, EOG and chin EMG signals are the cerebral hemispheres and cranial nerves 3, 4, 6 and 12. This represents a limited subset of the entire nervous system. However, as a result of the focused attention on these signals, the initiation, maintenance and quality of sleep is often perceived as derived from these aspects of the nervous system, particularly the cerebral hemispheres. The focus on the cerebrum has occurred, because that is what directly generates the EEG and the various brainwave states generally define 4 of the 5 stages of sleep, according to the existing guidelines. As such, adherence to these guidelines in clinical practice and research, creates a high degree of focus on the cerebral hemispheres and EEG.

Other areas of the nervous system have been overlooked as a result. In particular, the autonomic nervous system[1] (ANS), which does not directly create brainwaves (EEG), eye movements (EOG) or chin muscle activity (EMG), has been largely ignored as potentially playing a significant role in sleep.

Figure 14:
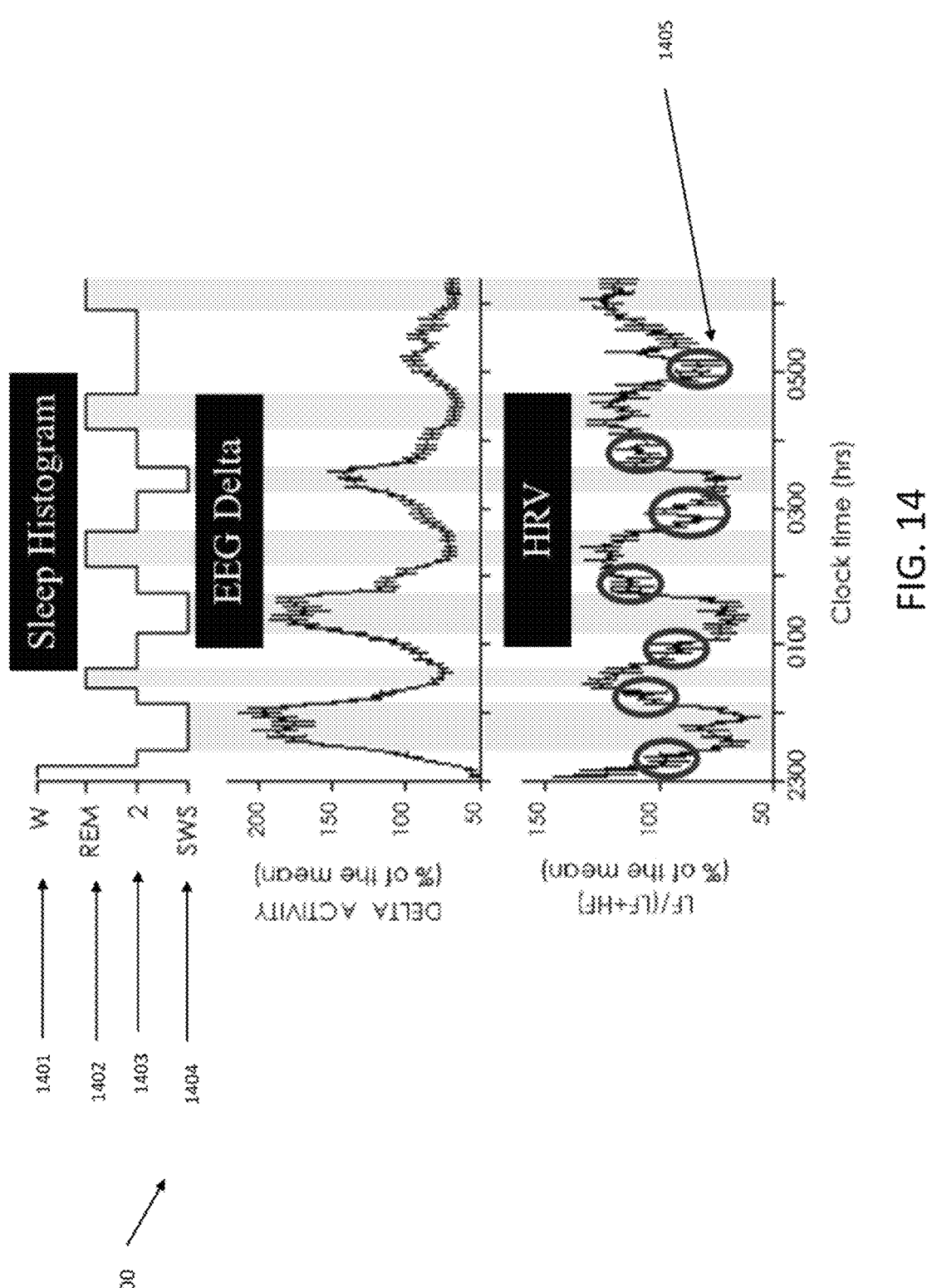
FIG. 14 depicts graphs showing the results of a digital frequency analysis of heart rate data.

[1]The autonomic nervous system is a control system that acts largely unconsciously and regulates bodily functions The FIG. 14 shows the correlation between the sleep histogram, delta EEG activity, and the normalized ratio of $$\frac{LF}{LF + HF}$$

power determined by frequency-based heart rate variability analysis. Of note, a number of scientific studies have demonstrated that the amount of power in the HF band is highly correlated with the level of parasympathetic activity of the ANS. Therefore, high HF activity is associated with a low $$\frac{LF}{LF + HF}$$

ratio, high LEG Delta activity and slow wave or delta sleep (Stages 3 and 4 by the old R&K criteria or N3 by the newer AASM guidelines). Also, of interest, the tracing shown of $$\frac{LF}{LF + HF}$$

ratio data, circled, associated with Stage 2 or N2 sleep is lower preceding slow wave or delta sleep as compared to that which precedes REM sleep. This suggests that S2 or N2 sleep, as presently categorized, may represent either 2 different stages of sleep or possibly may simply represent a transitional phase between the oscillations of delta (N3) and REM sleep and not be, in and of itself, a primary stage of sleep. In either situation the phase before delta sleep would seem to have higher relative parasympathetic activity or lower sympathetic activity versus the phase preceding Stage REM with relatively higher sympathetic activity (or less parasympathetic activity).

This study also, very importantly demonstrated that the changes in the $$\frac{LF}{LF + HF}$$

ratio, precede the EEG changes by 5 minutes. This represents strong evidence that changes in the ANS precede brainwave changes, potentially signifying some role in causation and regulation of sleep and EEG changes.

Therefore, although the phenomenology of sleep, as presently measured polysomnographically, suggest discrete stages (wake, N1, N2, N3 and REM), these phenomena, may simply be the resultant manifestations of more causative, regulatory, driving impulses emanating from the ANS, likely, in addition to other factors.

In further support of this notion, is data cited in the study entitled, "Spectral Analysis of Heart Rate Variability in Sleep", authored by P. BUŠEK, J. VAŇKOVÁ, J. OPAVSKÝ1, J. SALINGER1, S. NEVŠÍMALOVÁ from the Department of Neurology, First Faculty of Medicine, Charles University, Prague and 1Department of Physiotherapy and Pain Management, Faculty of Physical Culture, Palacky University, Olomouc, Czech Republic.

This study was more focused on the analysis of HRV data as it relates to Stage REM sleep. Using their analytic methodology, they found the highest $$\frac{LF}{HF}$$

ratio, highest LF band normalized power and highest VLF band normalized power in Stage REM. These researchers also confirmed the findings of the Brandenberger, et al. researchers.

Collectively, these findings, in addition to the findings in other related studies, strongly suggest the possibility that there may be two main oscillating pacemakers or causative drivers of potentially, only two major states of sleep, N3 or delta sleep and stage REM. In such a categorization, S2 or N2 sleep would simply be the transition into both delta and REM sleep, while N1 sleep would be the initial transition from wake towards delta sleep.

Given the fact that sleep first appears as a phenomenon in lower animal species with a less developed cerebrum and a well-developed ANS, it is logical to assume that the ANS is, at least in part, a driver, regulator or causative trigger for sleep and its various stages and a regulator of endocrine functioning during sleep, as documented by other scientific studies.

Figure 15:
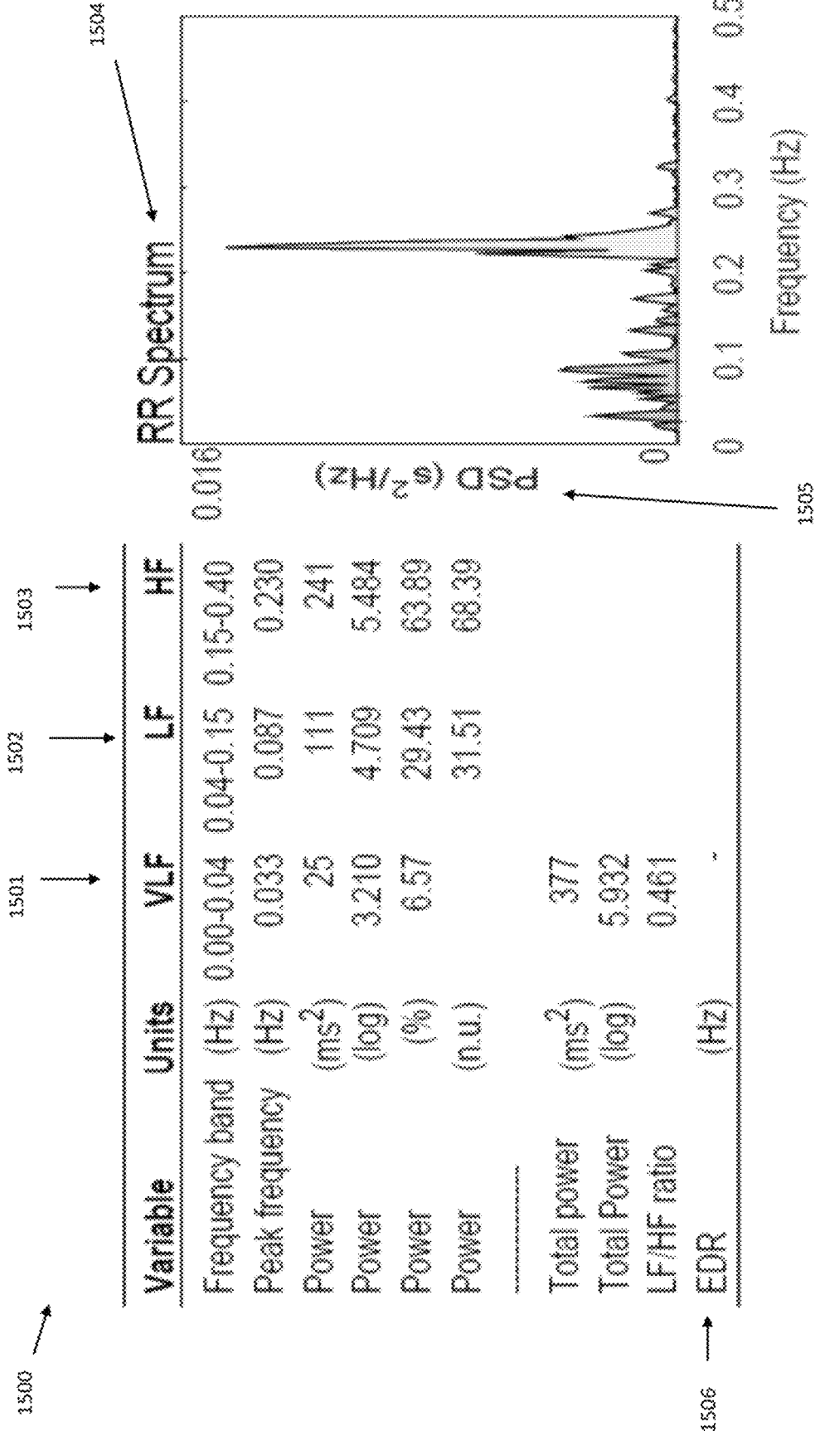
FIG. 15 depicts a chart and graph showing the results of a digital frequency analysis of heart rate data.

The table and chart below show the results of digital frequency analysis of 5 minutes of heart rate data revealing the peak frequencies and power associated with the three frequency bands of the ANS, during a segment of recording while the subject was in slow wave or delta sleep (N3). This stage of sleep tends to be dominated by increased power in the HF band. The frequency range noted below (0 Hz to 0.4 Hz) is generally unfamiliar territory to those focused on EEG phenomena (0.5 Hz to 40 Hz). The spectrum of frequency activity shown below are derived exclusively from an analysis of heart rate variability, which can also be obtained using pulse rate. This is shown in FIG. 15.

In addition to HRV changes ascribed to the ANS, there is another physiologic process that occurs within a small range of frequencies centered approximately around 0.26 Hz, which falls in the middle of the HF band and is unrelated to the ANS. That physiologic process is the act of breathing. During sleep, adult humans typically breathe on average, at a rate of approximately 15 to 16 breaths per minute or roughly 0.26 Hz. Respiration is managed by the nerve centers in the medulla and executed through somatic nerves that innervate the diaphragm and intercostal muscles. During the normal respiratory cycle, it is common to have normal respiratory sinus arrythmia. This results from a fluctuation in heart rate, which occurs as the heart rate quickens during inhalation and slows during exhalation. This occurs during what is typically a 4 second cycle or approximately 0.26 Hz. This effect is more consistent in non-REM sleep, particularly delta sleep, as respiratory rate variability decreases (Respiratory rate variability in sleeping adults without obstructive sleep apnea, authored by Guillermo Gutierrez, Jeffrey Williams, Ghadah A. Alrehaili, Anna McLean, Ramin Pirouz, Richard Amdur, Vivek Jain, Jalil Ahari, Amandeep Bawa & Shawn Kimbro).

Therefore, both the autonomic nervous system, the medulla oblongata[2] and the somatic nerves[3] responsible for the act of respiration, contribute nerve activity below 0.5 Hz and are strongly associated with various sleep stage phenomena.

[2]is a long stem-like structure located in the brainstem.
[3]part of the peripheral nervous system associated with the voluntary control of body movements via skeletal muscles Furthermore, on a metaphysical or spiritual front, some of our subjects have perceived a change in an aspect of their and other's Human Energy Particle System (HEPS) related to magnetic stimulation at approximately 0.25 Hz or 0.26 Hz. This aspect of the HEPS is located beneath the feet, which appears disc-like in shape. The central column of the HEPS passes through this disc-shaped aspect and passes through the physical body in front of the spine. Many other aspects of the HEPS emanate from this column, which appears to be more primary.

With the magnetic stimulation of approximately 0.25 Hz or 0.26 Hz, the disc-like aspect begins to pulsate, like a bellows, enhancing flow through the central column from below, upwards. Subjects exposed to this magnetic stimulation below the feet, experience a tingling sensation in the feet, which then travels up the legs and can also then be experienced in the hands and throughout the body and head. This may or may not be an effect of stimulating the HEPS, although it is our belief that this does account for this effect, at least in part.

Unfortunately, at the present time, we are unaware of any scientific apparatus which can measure, display and analyze the HEPS. It is, however, our theory that the HEPS also plays a causative or regulatory role in sleep and other bodily functions, primarily due to the fact that the magnetic stimulation appears to be most effective at influencing bodily functions when positioned around or below the feet, which appears to influence one of the more primary interfaces between the HEPS and the physical body. It is also our assumption that the HEPS interacts with the peripheral and central nervous system and both HEPS and the nervous system react to magnetic stimulation.

Placing a magnetic field, that fluctuates with a frequency or multiple frequencies, below the feet, can directly affect the physical body too, provided the magnetic field is of sufficient strength. There are many nerve fibers located in the feet and legs. Nerves contain neurons, the cells that transmit and receive nervous impulses and most neurons are encased by glial cells.

Glial cells far outnumber neurons throughout the nervous system. The progenitor glial cell, the primitive astrocyte, differentiates into all the other types of glial cells (astrocytes, oligodendrocytes, microglia and ependymal cells, in the central nervous system and Schwann cells in the peripheral nervous system). Primitive astrocytes even differentiate into neurons themselves. Glial cells provide nutritive support for neurons.

Glial cells are also important regulators of the potassium ion in the extracellular fluid surrounding neurons and therefore, play a significant role in neuronal firing. In addition, glial cells can uptake neurotransmitters, further impacting neuronal firing and therefore neuronal firing rates. It is particularly noteworthy that oligodendrocytes centrally and Schwann cells peripherally, communicate with similar adjacent cells through gap junctions in their cell membranes. This allows ionic transfer from the cytoplasm of one glial cell to the cytoplasm of adjacent glial cells. Oligodendrocytes can also communicate with astrocytes in a similar manner.

These glial cells, therefore, form an analog network or circuitry, independent of the digital neuronal circuitry. This glial cell network was termed "the DC perineural system" by Robert O. Becker, M.D. Becker's research on the perineural system found that the Schwann cells carry the electrical signals that cause bone fractures to heal. This provided the foundation for the development of bone growth stimulators to heal recalcitrant bone fractures.

Although the current in this DC perineural system is direct current (DC), there are scientific reasons to believe that, if influenced by electrical, electromagnetic or magnetic energy, it could also convey frequency content and vary in amplitude. Therefore, given the existence of an analog perineural conduction network that can potentially modify neuronal firing, it is theorized that the DC perineural system could be used to influence and entrain neuronal firing rates. This could have profound applications for affecting sleep, in addition to potentially treating or healing a multitude of other medical, psychological and emotional conditions.

Regarding sleep, it is of great interest that the frequency of respiration is almost identical to that which is observed to be the frequency of stimulation of that aspect of the HEPS, that appears to be the main gateway between the HEPS and physical body. It is similarly noteworthy that approximately the same frequency resides in the middle of the HF band that is associated with the parasympathetic division of the ANS, also linked to restoration and healing, particularly during delta sleep, and that the highest relative power in that frequency band is associated with slow wave or delta sleep, which is also associated with growth hormone secretion (Sleep. 1996 December; 19(10):817-24).

Regardless of cause and effect between cerebral influences on sleep, medullary respiratory control of respiratory rate, ANS activity, or potential HEPS influence on sleep, it seems apparent that entrainment of the ANS, the aspects of the nervous system related to respiratory rate and possibly even the HEPS, at a rate of approximately 0.25 Hz or 0.26 Hz should produce or predispose a person to experiencing delta sleep. We theorized that by magnetically stimulating the nerves of the feet and legs and the aspects of the HEPS at and below the feet, at approximately those frequencies, delta sleep would be induced.

In a polysomnographic study of 4 subjects, not long after waking from a normal night's sleep, when sleep, let alone delta sleep should not occur, delta sleep was induced using magnetic stimulation ranging from 0.22 Hz to 0.26 Hz in 3 of the 4 subjects, during the last 30 minutes of a 55-minute stimulation session. During the first 25 minutes of the stimulation, additional perturbations in the magnetic field ranging from 7.5 Hz to 3.5 Hz were added to assist in inducing light sleep, which occurred in all 4 subjects. The perturbations during the next 30 minutes of the session ranged from 3.5 Hz to 1.5 Hz. It had been our experience that using the perturbations without the lower frequencies (0.22 Hz to 0.26 Hz) did not produce sleep, although it is possible that the additional effects of the perturbations influenced the cerebrum and resulting EEG findings. Normally however, a subject would progress from light sleep to delta sleep in about the timeframe that it took place in this study, so the impact of the perturbations are not fully known. Further research is indicated.

Figure 16:
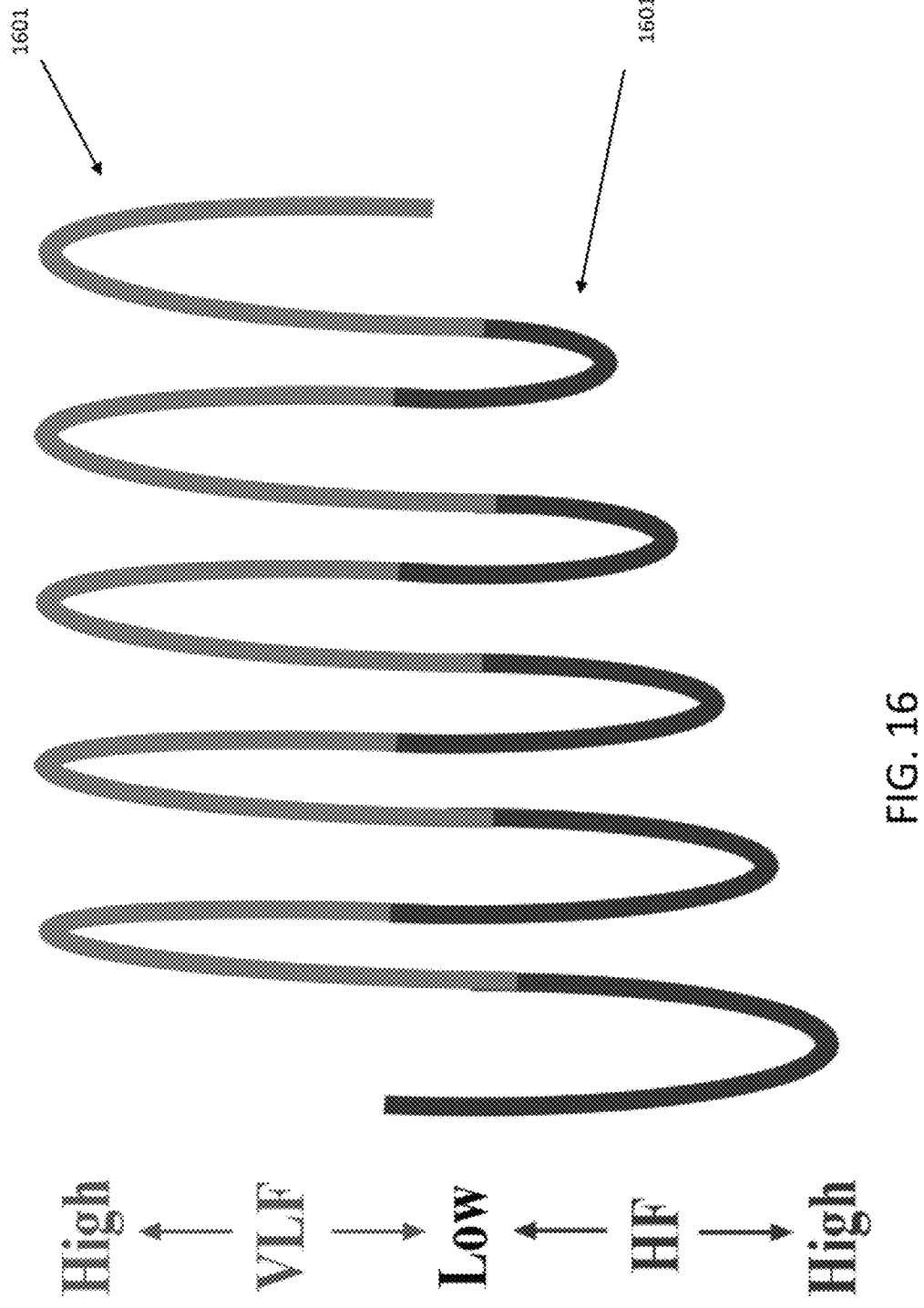
FIG. 16 depicts a model of a biphasic ultradian rhythm between delta sleep inducing signal and REM sleep inducing signal.

The illustration in FIG. 16 depicts the model of a biphasic[4] ultradian rhythm[5] (Delta sleep inducing signal 1602, REM sleep inducing signal 1601), during 5 sleep cycles. Delta sleep could be induced or supported by magnetic stimulation of approximately 0.26 Hz (within the HF band), while REM sleep could be induced or supported by magnetic stimulation of frequencies in the range of approximately 0.003 Hz to approximately 0.4 Hz (the VLF, LF and HF bands). Additional magnetic frequencies, in the EEG spectrum, could be added to each phase (delta frequencies for delta sleep or theta frequencies for REM sleep) to affect the user's cerebral functions and brainwaves. In addition, the amplitude of the magnetic frequency stimulation could be adjusted, particularly for delta sleep, to reduce the effective HF band stimulation within each subsequent sleep cycle. In a similar fashion, amplitude adjustments of both bands, could potentially create the differences seen in Stage N2 (light sleep) preceding N3 and preceding REM. Alternatively, both stimuli (HF and VLF+LF+HF) could be administered at those times in varying proportions, using more than one magnet.

[4]Practice of sleeping during two periods over 24 hours.
[5]In chronobiology, an ultradian rhythm is a recurrent period or cycle repeated throughout a 24-hour day The frequencies used to provide greater HRV, HF band activity, also can be used to more directly stimulate the phrenic nerve to entrain respiratory rate. Similarly, magnetic frequency stimulation can entrain heart rate. Both methods can be used singly or in combination.

For the purpose of providing the correct magnetic stimulation at the appropriate time, to provide the best results for the user, it is helpful to monitor the person's sleep pattern in real time, or at least have a reasonable understanding of the person's sleep cycle durations and when they fell asleep. To this end, real-time monitoring of the person's frequency-based HRV data (and other data if available, including EEG, respiratory and other data recorded during polysomnography) in conjunction with historical data documenting the duration of each of the sleep cycles, as they vary across individuals, provides the best solution. Real-time data supplied directly to the magnetic stimulus device, also with access to the person's historical data, typically stored in a database, can accomplish this end. If the user is not wearing the monitor which provides real-time HRV data, improved results can still be achieved with a monitor that simply senses movement, to gain a reasonable estimate of sleep onset in conjunction with the person's historical data.

As mentioned, an increase in HRV HF band activity is directly correlated with activity of the parasympathetic division of the ANS. Greater activity of the parasympathetic division of the ANS during waking, is accompanied by greater relaxation and relief from stress. Therefore, inducing higher HF band activity can directly impact stress, stress related illnesses and conditions such as; hypertension, heart disease, anxiety, depression, asthma, diabetes, irritable bowel syndrome, gastro-esophageal reflux disorder, headaches, Alzheimer's disease, accelerated aging and premature death. Related conditions include ADHD, PTSD, drug and alcohol withdrawal and addiction recovery. In addition, greater parasympathetic activation also reduces pain, by reducing neuronal firing of neurons conveying pain.

One disease state that has a predominant symptom of pain, as well as sleep disturbance is Fibromyalgia. One study of 329 patients with fibromyalgia demonstrated a statistically significant reduction of parasympathetic nervous system activation at night along with decreased total power of the autonomic nervous system (Reduction in Parasympathetic Autonomic Nervous System Function in Fibromyalgia Patients. Study performed by David S. Silver, Sarah R. Markoff, Leah Naghi, Michael Silver, and Lawrence May).

Another painful state that can benefit from this form of magnetic stimulation is peripheral neuropathy, and specifically diabetic peripheral neuropathy (DPN). Our initial investigation of DPN reveals the ability to reduce or eliminate pain and reduce numbness. Reducing numbness indicates improved peripheral nerve function or regrowth of nerve tissue. Further study is necessary to distinguish between the two possibilities. In addition, it is suspected that regular use of magnetic stimulation would improve hemoglobin A1c levels, demonstrating improved regulation of blood glucose levels and may cause weight loss due to greater release of thyroid stimulating hormone, which could lower insulin resistance and vastly improve Type 2 Diabetes.

Greater activation of the parasympathetic division of the ANS is an excellent way to induce or improve upon a person's state of relaxation or meditation. There are presently approximately 250 forms of addiction and 75% of them utilize the 12-step program, initially devised for relief from addiction to alcohol. The 11th step in that program calls for meditation and prayer.

In a number of clinical studies, meditation has also been shown to regenerate nerve tissue in the brain. Parkinson's Disease, Multiple Sclerosis and other neurodegenerative diseases represent illnesses with little hope of significant symptom reversal or amelioration. They generally lead to relentless disability, incapacity and ultimately, death. These disease states are of particular interest because meditation has been proven to enhance nerve growth in terms of gray matter (nerve cells) and white matter (neurons).

The following studies provide substantiation: Long-term meditation is associated with increased gray matter density in the brain stem. Neuroreport, 20(2), 170-174:

This study compared long-term meditators with age-matched controls with Magnetic Resonance Imaging and found structural differences in regions of the brainstem that are known to be concerned with mechanisms of cardiorespiratory control.

The underlying anatomical correlates of long-term meditation: larger hippocampal and frontal volumes of gray matter. Neuroimage, 45(3), 672-678:

Another study that compared long-term meditators with matched control participants. The main findings were that meditators had larger gray matter volumes than non-meditators in brain areas that are associated with emotional regulation and response control (the right orbito-frontal cortex and the right hippocampus).

Mechanisms of white matter changes induced by meditation. Proceedings of the National Academy of Sciences, 109(26), 10570-10574:

This study shows the impact of meditation practice on the connections between brain areas using Diffusion Tensor Imaging (DTI). After only four weeks of meditation changes in white matter—which is strongly involved in interconnecting brain areas were present in those participants who meditated but not in the control participants who engaged in relaxation exercises. Interestingly, these changes involved the anterior cingulate cortex, a part of the brain that contributes to self-regulation, an important aspect when people start engaging with meditation practice.

FIG. 14 shows the correlation between the sleep histogram, delta EEG activity, and the normalized ratio of $$\frac{LF}{LF+HF}$$

power determined by frequency-based heart rate variability analysis. Of note, a number of scientific studies have demonstrated that the amount of power in the HF band is highly correlated with the level of parasympathetic activity of the ANS. Therefore, high HF activity is associated with a low $$\frac{LF}{LF+HF}$$

ratio, high EEG Delta activity and slow wave or delta sleep (Stages 3 and 4 by the old R&K criteria or N3 by the newer AASM guidelines).

Also, of interest, the tracing shown in FIG. 14 of $$\frac{LF}{LF+HF}$$

ratio data depicted as 1405, associated with Stage 2 or N2 sleep 1403 is lower preceding slow wave or delta sleep 1404 as compared to that which precedes REM sleep 1402. 1401 depicts being awake. This suggests that N2 sleep, as presently categorized, may represent either 2 different stages of sleep or possibly may simply represent a transitional phase between the oscillations of delta (N3) and REM sleep and not be, in and of itself, a primary stage of sleep. In either situation the phase before delta sleep would seem to have higher relative parasympathetic activity or lower relative sympathetic activity versus the phase preceding Stage REM with relatively higher sympathetic activity (or less parasympathetic activity).

This study also, very importantly demonstrated that the changes in the $$\frac{LF}{LF+HF}$$

ratio, precede the EEG changes by 5 minutes. This represents strong evidence that changes in the ANS precede brainwave changes, potentially signifying some role in causation and regulation, as opposed to only association.

Given the fact that sleep first appears as a phenomenon in lower animal species with a less developed cerebrum and a well-developed ANS, it is logical to assume that the ANS is, at least in part, a driver, regulator or causative trigger for sleep and its various stages and a regulator of endocrine functioning during sleep, as documented by a number of scientific studies.

The table and chart in FIG. 15 show the results of digital frequency analysis of 5 minutes of heart rate data revealing the peak frequencies and power associated with the three frequency bands of the ANS, during a segment of recording while a subject was in slow wave or delta sleep (N3). The chart labels 1501, 1502, and 1503 depict very low frequency, low frequency, and high frequency bands respectively. The graph heading 1504 is the respiratory rate spectrum. The graph variable 1505 is power spectral density and the variable 1506 is electro dermal response. This stage of sleep tends to be dominated by increased power in the HF band. The frequency range noted below (0 Hz to 0.4 Hz) is generally unfamiliar territory to those focused on EEG phenomena (0.5 Hz to 40 Hz). The spectrum of frequency activity shown below are derived exclusively from an analysis of heart rate variability, which can also be obtained using pulse rate.

In addition to HRV changes ascribed to the ANS, there is another physiologic process that occurs within a small range of frequencies centered approximately around 0.26 Hz, which falls in the middle of the HF band and is unrelated to the ANS. That physiologic process is the act of breathing. During sleep, adult humans typically breathe on average, at a rate of approximately 15 to 16 breaths per minute or approximately 0.26 Hz. Respiration is managed by the nerve centers in the medulla oblongata of the brainstem and executed through somatic nerves that innervate the diaphragm and intercostal muscles. During the normal respiratory cycle, it is common to have normal respiratory sinus arrythmia, also termed normal sinus rhythm. This results from a fluctuation in heart rate, which occurs as the heart rate quickens during inhalation and slows during exhalation. This occurs during what is typically, approximately, a 4 second cycle or approximately 0.26 Hz. This effect is more consistent in non-REM sleep, particularly delta sleep, as respiratory rate variability decreases (Respiratory rate variability in sleeping adults without obstructive sleep apnea, authored by Guillermo Gutierrez, Jeffrey Williams, Ghadah A. Alrehaili, Anna McLean, Ramin Pirouz, Richard Amdur, Vivek Jain, Jalil Ahari, Amandeep Bawa & Shawn Kimbro).

Therefore, both the autonomic nervous system, the medulla oblongata and the somatic nerves responsible for the act of respiration, contribute nerve activity below 0.5 Hz, particularly around 0.25 Hz or 0.26 Hz and are strongly associated with various sleep stage phenomena.

Collectively, the findings cited above, suggest the possibility that there may be two main oscillating pacemakers or causative drivers of potentially, only two major states of sleep, N3 or delta sleep (also considered non-REM sleep) and stage REM. In such a categorization, S2 or N2 sleep would simply be the transition into both delta and REM sleep, while N1 sleep would be the initial transition from wake towards delta sleep.

The FIG. 16 depicts the model of a biphasic ultradian rhythm (Delta sleep inducing signal 1602, REM sleep inducing signal 1601), which conceivably could be supplemented by the effects of one oscillating or rotating magnet moving at various frequencies.

Figure 17:
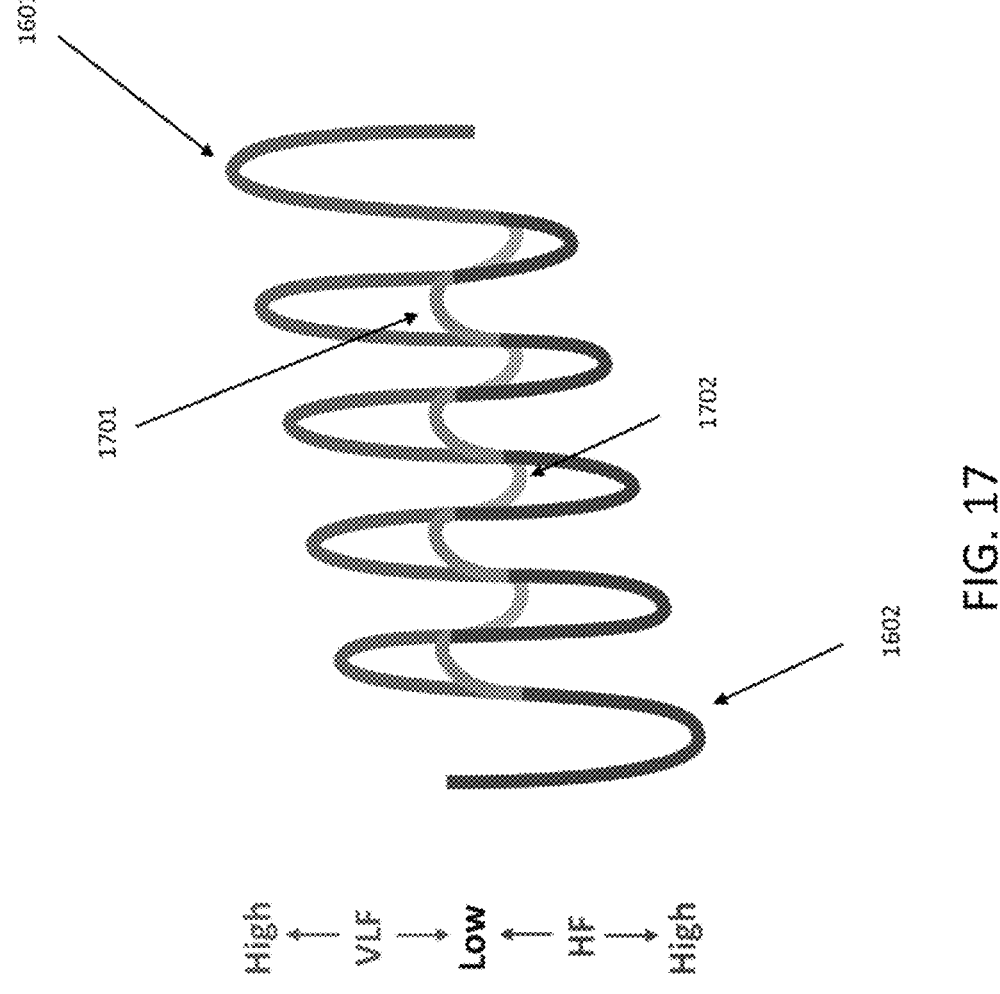
FIG. 17 depicts a model of a biphasic ultradian rhythm between delta sleep inducing signal and REM sleep inducing signal with independent stimulation patterns for Delta and REM sleep occurring simultaneously.

The FIG. 17 depicts independent stimulations patterns for Delta and REM sleep occurring simultaneously. In this figure, greater intensity (amplitude) of the signals are shown by darker color (versus the pale and light segments 1701 and 1702, which represents lessor amplitude). These rhythms conceivably could be supplemented by the effects of two oscillating or rotating magnets moving at various frequencies.

Experimentation has demonstrated that Delta sleep can be induced or supported by magnetic stimulation of approximately 0.26 Hz (within the HF band). It is believed that REM sleep can be induced or supported by magnetic stimulation of frequencies in the range of approximately 0.003 Hz to approximately 0.04 Hz (within the VLF band) and in the range of approximately 0.04 Hz to approximately 0.15 Hz (within the LF band). Additional magnetic frequencies could be added to each phase (delta EEG frequencies for delta sleep, theta EEG frequencies for light sleep and for REM sleep) to affect the subject's cerebral functions and brainwaves. In addition, the amplitude of the magnetic frequency stimulation could be adjusted, for delta and REM sleep, to reduce or augment the effective VLF, LF or HF band stimulation within each subsequent sleep cycle. In a similar fashion, amplitude adjustments of these bands, could potentially create the differences seen in Stage N2 (light sleep) preceding N3 and preceding REM. Alternatively, ANS frequency stimuli (HF, LF and VLF) could be administered at those times in varying proportions, using more than one magnet.

The frequencies used to provide greater HRV, HF band activity, also can directly or indirectly stimulate the phrenic nerve to entrain respiratory rate. Similarly, magnetic frequency stimulation can entrain heart rate, presumably be affecting the vagus nerve. Both methods can be used singly or in combination.

Real-time feedback of relevant data is often employed in engineering and medical systems, allowing for real-time adjustments to be made for relevant interventions. For the purpose of providing the correct magnetic stimulation at the appropriate time, in order to provide the best sleep outcome for the subject, it is helpful to monitor the subject's sleep pattern in real-time, or at least have a reasonable understanding of the subject's sleep cycle durations and when they fell asleep. To this end, real-time monitoring of the subject's frequency-based HRV data (and other data if available, including EEG, respiratory blood oxygen saturation, limb or body motion and other data recorded during polysomnography) in conjunction with historical data documenting the duration of each of the sleep cycles, as they vary across individuals, provides the best solution. Such real-time data supplied directly to the magnetic stimulus device, also with access to the subject's historical data, typically stored in a database, can accomplish this end, by allowing for real-time adjustments to the magnetic stimulus parameters. If the subject is not wearing a monitoring device or devices which provides real-time HRV or other data, improved results can still be achieved with a monitor that simply senses movement of the subject in bed, to gain a reasonable estimate of sleep onset in conjunction with the subject's historical data.

To assess the required physiologic metrics wearable devices can be used in conjunction with the magnetic stimulating device. One such wearable device can be worn on the arm or leg of the subject. This wearable device measures, analyzes, records and transmits the following data: the subject's movement of the arm or leg, pulse activity and blood oxygen saturation, from which is derived movement data, pulse rate data, pulse rate variability data, frequency-based heart rate variability data, including total power within the frequency spectrum of approximately 0.003 Hz to approximately 0.04 Hz, total power and peak frequency within the VLF, LF and HF bands, and blood oxygen saturation data, as well as the standard deviation of blood oxygen saturation data. Data is analyzed within discrete time periods during the measurement and recording session.

Another wearable device that can be used in conjunction with the aforementioned wearable device worn on the subject's arm or leg, can be placed on the subject's torso on the lower chest or upper abdominal area. This wearable device measures, records, analyzes and transmits the following data: the subject's body position (upright or lying on their back, left side, right side or stomach), and chest or abdominal wall motion from which is derived minute ventilation data, respiratory rate data, respiratory rate variability data, snoring data and respiratory event data (cessations or reductions in respiration termed respectively, apneas or hypopneas).

Both sets of data from the aforementioned wearable devices on the arm or leg and torso, provide somewhat equivalent data to that measured, recorded and analyzed during polysomnography, performed in either a sleep diagnostic laboratory or a home setting. This data can be analyzed in real-time and the results transmitted to the magnetic stimulating device.

Both sets of data from the aforementioned wearable devices on the arm or leg and torso, can be used to diagnose or screen subjects for the presence or absence of sleep apnea (SA) or obstructive sleep apnea (OSA), thereby allowing the subject to realize that they may suffer from such conditions. Subjects with SA or OSA may or may not benefit from use of the magnetic stimulating device.

Another device affixed to the subject's bed can also provide measurements of the subject's movements. This can be helpful in identifying the likelihood of sleep onset, which in the absence of data from the aforementioned wearable devices, can provide some useful information to the magnetic stimulation device in terms of adjusting its stimulation parameters.

Real-time and historical data, which can be used to assess the subject's sleep pattern and provide feedback to a device providing interventional stimuli can include: EEG, EOG, chin EMG, leg EMG, EKG, pulse rate, historical normalized pulse rate values correlated to non-normalized pulse rate data per sleep stage during prior sessions, time or frequency-based HRV or pulse rate variability data (including total power in VLF, LF and HF bands, power in each of those bands and related historical normalized and correlated non-normalized values per sleep stage during prior recording session and peak frequencies in each of those bands), respiratory rate, historical normalized respiratory rate values correlated to non-normalized respiratory rate data per sleep stage during prior sessions, respiratory rate variability, historical normalized respiratory rate variability values correlated to non-normalized respiratory rate variability data per sleep stage during prior sessions, minute ventilation, historical normalized minute ventilation values correlated to non-normalized minute ventilation data per sleep stage during prior sessions, standard deviation of blood oxygen saturation values, historical normalized standard deviation of blood oxygen saturation values correlated to non-normalized standard deviation of blood oxygen saturation data per sleep stage during prior sessions, subject movement data, respiratory events such as apneas and hypopneas, drops in blood oxygen saturation values and snoring events. In addition, many of these values can be correlated with body position for later reference and use.

As previously mentioned, initiation of changes in brain-wave states has been shown to be preceded by changes associated with the autonomic nervous system (ANS) as shown by Brandenberger, et al, during sleep. Specifically, delta sleep is preceded by changes primarily in the HF and LF bands associated with increased parasympathetic ANS activity or decreased sympathetic activity by 5 minutes. It is reasonable to assume that either neuronal pathways or neuro-humoral or neuro-chemical mechanisms or combinations thereof, exist between the ANS and cerebral hemispheres to induce such changes in brainwaves during sleep, as well as during waking.

As previously mentioned, an increase in HRV HF band activity is directly correlated with activity of the parasympathetic division of the ANS. Greater activity of the parasympathetic division of the ANS during waking, is accompanied by greater relaxation and relief from stress. Therefore, inducing higher HF band activity can directly impact stress, stress related illnesses and conditions such as; hypertension, heart disease, anxiety, depression, insomnia, asthma, diabetes, irritable bowel syndrome, gastro-esophageal reflux disorder, headaches, fibromyalgia, Alzheimer's disease and other neurodegenerative conditions, accelerated aging and premature death. Related conditions include ADHD, autism, PTSD, drug and alcohol withdrawal, addiction recovery and others. In addition, greater parasympathetic activation also reduces pain, by reducing neuronal firing of neurons conveying pain.

Regarding pain and the peripheral nervous system, Dr. Becker has also described the current of injury and subsidence of this current with healing, and its associated changes regarding glial and nerve cells. His research suggests that another painful state that can benefit from this form of magnetic stimulation is peripheral neuropathy, which includes diabetic peripheral neuropathy (DPN). Our initial investigation of DPN reveals the ability to reduce or eliminate pain and reduce numbness. Reducing numbness indicates improved peripheral nerve function or regrowth of nerve tissue.

It is hypothesized that regular use of magnetic stimulation would improve hemoglobin A1c levels, demonstrating improved regulation of blood glucose levels and weight loss, which could lower insulin resistance and vastly improve Type 2 Diabetes.

Another disease state that has a predominant symptom of pain, as well as sleep disturbance is fibromyalgia. One study of 329 patients with fibromyalgia demonstrated a statistically significant reduction of parasympathetic nervous system activation at night along with decreased total power of the autonomic nervous system (Reduction in Parasympathetic Autonomic Nervous System Function in Fibromyalgia Patients, David S. Silver, Sarah R. Markoff, Leah Naghi, Michael Silver and Lawrence May, Cedars Sinai Medical Center, USA, University of California, Los Angeles School of Medicine, USA, Targeted Medical Pharma, USA, University of Southern California School of Medicine, USA, University of Southern California Marshall School of Business, USA). It is anticipated that magnetic enhancement of ANS activity, specifically HF band activity associated with the parasympathetic division of the ANS, may ameliorate or improve this condition.

Greater activation of the parasympathetic division of the ANS is an excellent way to induce or improve upon a person's state of relaxation or meditation. There are presently approximately 250 forms of addiction and 75% of them utilize the 12-step program, initially devised for relief from addiction to alcohol. The 11th step in 12-step programs call for meditation and prayer.

Glycation, sometimes called non-enzymatic glycosylation, is typically the result of covalent bonding of a protein or lipid molecule with a sugar molecule, such as fructose or glucose, without the controlling action of an enzyme. All blood sugars are reducing molecules.

In all its forms, glycation reduces +1 charges on proteins or lipids down to either neutral charge (0) or even down to anionic −1. This increased electronegativity means that each glycated protein or lipid is more likely to bind metal ions (all having positive charges) than would be the tendency for corresponding healthy proteins/lipids.

Glycation is the nonenzymatic reaction of glucose, α-oxo-aldehydes, and other saccharide derivatives with proteins, nucleotides, and lipids. Early glycation adducts (fructosamines) and advanced glycation adducts (AGEs) are formed. "Glycoxidation" is a term used for glycation process involving oxidation. Sural, peroneal, and saphenous nerves of human diabetic subjects contained AGEs in the perineurium, endothelial cells, and pericytes of endoneurial microvessels and in myelinated and unmyelinated fibres localized to irregular aggregates in the cytoplasm and interstitial collagen and basement membranes. (Glycation in diabetic neuropathy: Characteristics, consequences, causes, and therapeutic options.

Low-amplitude magnetic stimulation, such as occurs with our technology, may mitigate an effect of systemic glycation, which is the anomalous low-barrier trapping of metal ions (hindering metal ion transport) and potentially, glycation or its effects, as seen in diabetic peripheral neuropathy, for example. The EM flux may nudge ions out of low-barrier traps formed by glycated units such as carboxymethyl-lysine (a hard ion chelator) and methylglyoxal-arginine, cross-linked imidazole and pentosidine (soft ion chelators).

This fits with observations that glycation-based iron dysregulation is a marker for sleep disorders (https://www-.sciencedirect.com/science/article/pii/S0014579308003967) and fibromyalgia (https://www.frontiersin.org/articles/10.3389/fmed.2017.00198/full). On the flip side, recent studies identify glycation as a key factor in tumor growth (https://www.ncbi.nlm.nih.gov/pubmed/29373651).

Therefore, by remediating glycation/metal dysregulation, the benefits may extend beyond sleep disorders, fibromyalgia and (anecdotally) cancer, to other diseases for which glycation pathology is best established, including diabetes, psoriasis, eczema and Crohn's Disease. This mechanism may also extend to neuro-pathologies.

Habituation of primary sensory cortical regions of the cerebrum occur when a repetitive stimulus is provided, the response to the stimulus decreases after repeated or prolonged presentations of that stimulus. It is well understood that relaxation, meditation, and other states of consciousness can be produced by habituating the brain to a repetitive, non-threatening stimulus, such as sound or vibration or a combination of the two. Techniques that habituate the brain can be used in conjunction with magnetic stimulation that entrain the brain and other aspects of the nervous system, such as the ANS. This combination of habituation and entrainment can be particularly beneficial in subjects with recalcitrant conditions such as severe chronic insomnia, anxiety, PTSD and for healing and treating a variety of illnesses and conditions.

In a number of clinical studies, meditation has also been shown to regenerate nerve tissue in the brain. Alzheimer's Disease, Parkinson's Disease, Multiple Sclerosis and other neurodegenerative diseases represent illnesses with little hope of significant symptom reversal or amelioration. They generally lead to relentless disability, incapacity and ultimately, death. These disease states are of particular interest because meditation has been proven to enhance nerve growth in terms of gray and white matter (neurons). One study compared long-term meditators with age-matched controls with Magnetic Resonance Imaging and found structural differences in regions of the brainstem that are known to be concerned with mechanisms of cardiorespiratory control. (Long-term meditation is associated with increased gray matter density in the brain stem. Neuroreport, 20(2), 170-174). Another study that compared long-term meditators with matched control participants. The main findings were that meditators had larger gray matter volumes than non-meditators in brain areas that are associated with emotional regulation and response control (the right orbitofrontal cortex and the right hippocampus). (The underlying anatomical correlates of long-term meditation: larger hippocampal and frontal volumes of gray matter. Neuroimage, 45(3), 672-678). An alternate study shows the impact of meditation practice on the connections between brain areas using Diffusion Tensor Imaging (DTI). After only four weeks of meditation changes in white matter—which is strongly involved in interconnecting brain areas were present in those participants who meditated but not in the control participants who engaged in relaxation exercises. Interestingly, these changes involved the anterior cingulate cortex, a part of the brain that contributes to self-regulation, an important aspect when people start engaging with meditation practice. (Mechanisms of white matter changes induced by meditation. Proceedings of the National Academy of Sciences, 109(26), 10570-10574). Therefore, it is anticipated that magnetic enhancement of parasympathetic activity of the ANS using magnetic stimulation to induce a meditative state can promote similar healing.

Dr. Becker's research on the DC perineural system suggests that magnetic or electromagnetic stimulation peripherally, at a distal location, such as the hands or feet of a subject, could influence the DC perineural system in a manner to conduct a low frequency current or create a low frequency waveform. This waveform or current could be conducted more proximally, potentially influencing those structures that were functioning in a similar frequency range. Such influence could include entrainment of those structures, so that they would resonate or fire at similar or the same frequency. More proximal structures could include more centrally located aspects of the nervous system, which would include other peripheral nerves, the ANS, cranial nerves including the vagus nerve, the spinal cord, brainstem, cerebellum and cerebrum. In this manner low frequency magnetic or electromagnetic stimulation at the periphery, hands and feet, could entrain glial and nerve cells to function or fire at the same or similar rates. It is believed that the effects of such stimulation can improve the aforementioned illnesses and conditions.

It is not intuitive, even to those reasonably skilled in the art, that a rotating disk comprising non-magnetic alloys, such as brass and certain stainless-steel alloys would be affected by a magnet, e.g. Austenitic series such as 304 when in fact it plays a significant role. As the disk spins, a magnetic field is built up in the disk and adds to the field of the spinning magnet, the magnetic fields add using vector addition. As an example, if at some point (r) you have a field $B_1(r)$ and you introduce another magnetic field $B_2(r)$ then the total field is just the vector sum of the two where $B_r=B_1+B_2$. This essentially allows a method of "amplifying"

the magnitude of the magnet regardless of rotational frequency of the magnet by changing the angular velocity of the spinning disk. Cutting the disk, or windowing the disk modifies the strength of the field generated, this a variable attenuation that can be implemented at design time of the product to achieve a specific effect of the magnetic fields.

This magnetic effect is termed an Eddy Current; these are generated when a conductor moves through a changing magnetic field, an eddy current is induced within the conductor according to Faraday's law of induction. Eddy currents are electrical currents that flow in closed loops within the conductor perpendicular to the magnetic field. "The magnitude of the current in a given loop is proportional to the strength of the magnetic field, the area of the loop, and the rate of change of flux, and inversely proportional to the resistivity of the material." I is the magnitude of the eddy current, B is the strength of the magnetic field, A is the area of the loop, ρ is the electrical resistivity of the material.

$$|I_{eddy}| = \frac{BA}{\rho}\frac{\partial \Phi}{\partial t} \qquad [028]$$

The eddy current generates a magnetic field that opposes the external magnetic field acting on the conductor in accordance to the right-hand rule as depicted earlier in FIG. 1, it shows the direction of the eddy current given by Lenz Law.

When an electron flows through a uniform magnetic field, it experiences the Lorentz force acting on the electron. This gives the electron a centripetal acceleration through the conducting disk as it spins. If the charged particle is constantly deflected, the radius at which this electron flows in a loop is given by equating the Lorentz force to the centripetal force. q is the charge of the electron, v is the velocity of the electron, m is the mass of the charged particle, and B is the strength of the magnetic field.

$$F = qvB = m\frac{v^2}{r} \qquad [029]$$

$$r = \frac{mv}{qB} \qquad [030]$$

Figure 18:
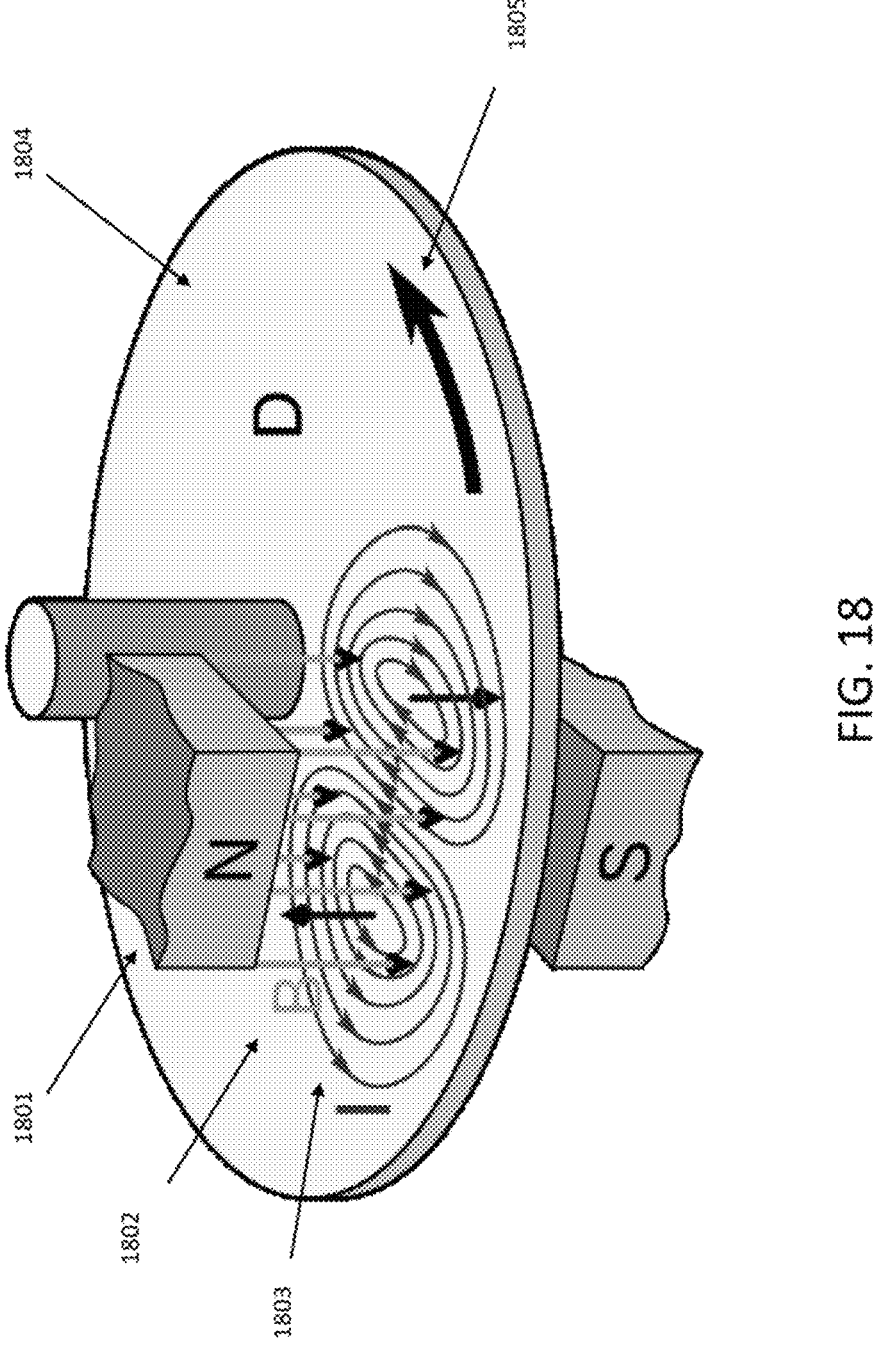
FIG. 18 depicts an illustration of how eddy-currents form in a spinning conductive disk moving through a magnetic field.

An illustration of eddy currents is depicted in FIG. 18. FIG. 18 depicts a spinning conductive disk moving through a magnetic field. 1801 is a permanent magnet producing an external magnetic field on the rotating conductive disk. 1802 is the induced magnetic field that is being formed by the induced eddy currents in the conductive disk. 1803 is the induced eddy current. The direction of the eddy current is known by Lenz law. 1804 illustrates the conductive disk within a magnetic field and 1805 illustrates the direction of rotation for the conductive disk. Eddy currents produce a force that resists the motion of the conducting disk. This force is also called the magnetic dampening or the magnetic braking force; this comes from Faraday's law. Faraday's law says the braking force is equal to the current I multiplied by the cross product of the current path l and the magnetic field B. The magnitude of this force is the product of the current, the path, the magnetic field, and the sine of the angle. Since the angle is perpendicular, the sine of the angle is equal to 1.

$$F=I(l \times B) \qquad [031]$$

$$|F|=IlB \sin \theta \qquad [032]$$

$$|F|=IlB \qquad [033]$$

Eddy currents in conductors will generate heat which is the power dissipated in the system. This power dissipated is proportional to the motional electromagnetic force (emf) multiplied by the current induced. This is also proportional to the current induced squared multiplied by the total resistance of the conducting disk.

$$P_{dissipated}=emf_{induced}*I_{induced}=I_{induced}^2 R \qquad [034]$$

The power dissipated is related to the total work of the system, including the power input into the stepper motor of the device.

Lenz's law states that with the motion or change in a magnetic field a current will induce within a material or circuit. That current will induce its own magnetic field since a magnetic field is formed from the movement of electrons. The magnetic force will oppose the initial changing magnetic field. The direction of this induced current is visually demonstrated from Fleming's right-hand rule.

Since the disk is a dynamical system rotating at predetermined speeds, we need to consider the angular velocity and Centripetal Acceleration to better understand the calculation for the induced eddy current. It is known from Newton's second law of motion. Force is equal to a mass multiplied by its acceleration. Newton's second law:

$$F=ma \qquad [035]$$

Figure 19:
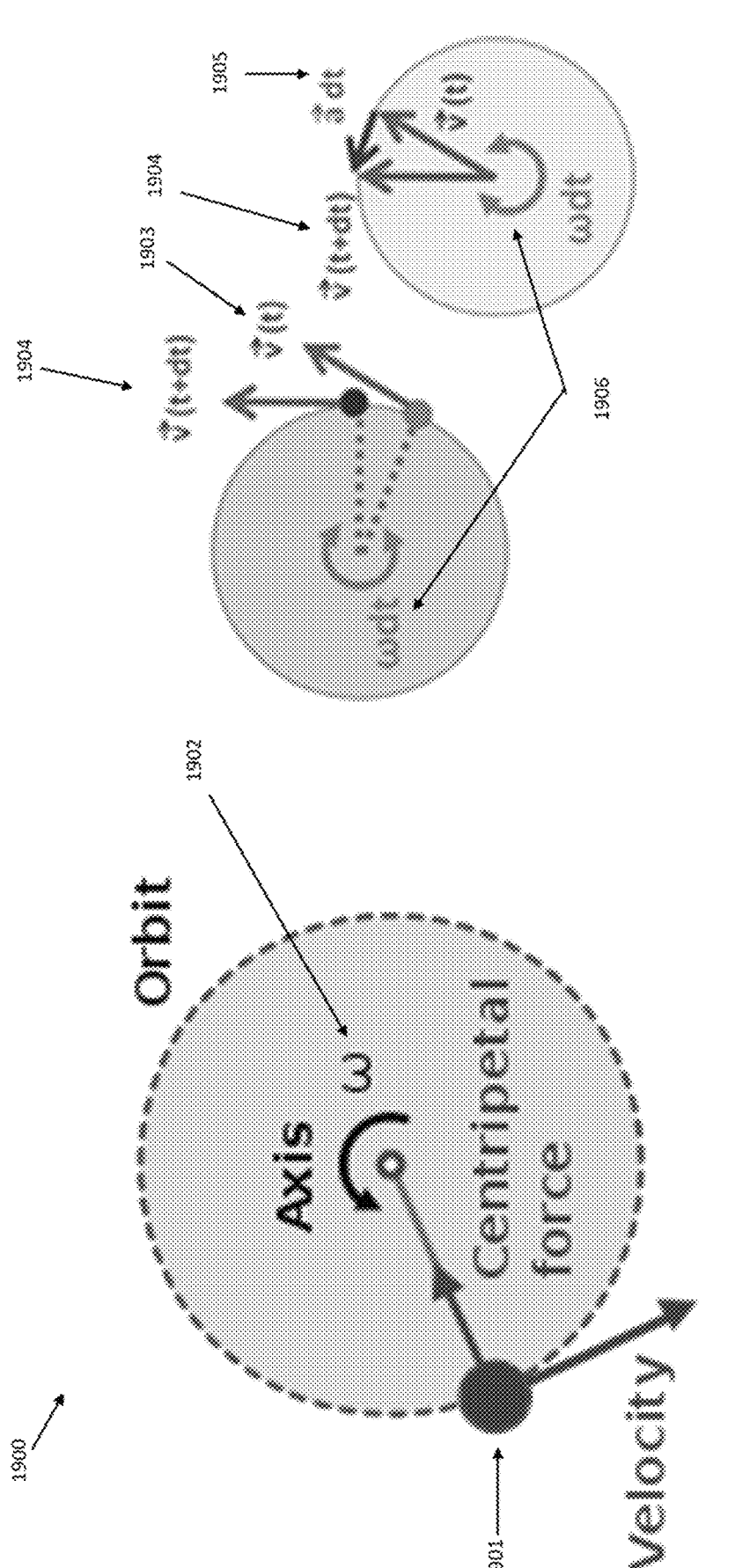
FIG. 19 depicts an illustration of a mathematical free body diagram for a rotating disk.

With a rotational motion, Newton's second law is adapted into terms of rotational acceleration. Where the centripetal acceleration is equal angular velocity squared times the radial path. Angular velocity can be expressed in terms of linear velocity divided by the radial path. FIG. 19 depicts a free body diagram of a rotating disk for the following calculations. 1901 depicts a point on the disk with tangential and radial velocity. 1902 depicts the angular velocity of the rotating disk. 1903 depicts the tangential velocity at a point with respect to time. 1904 shows the tangential velocity at a point one-time step away. 1905 depicts the relationship of velocity to acceleration per time step. 1906 shows angular velocity in relationship to a time step.

$$a = \omega^2 R \qquad [036]$$

$$\omega = \frac{v}{r} \qquad [037]$$

$$F = m\frac{v^2}{r} \qquad [038]$$

Angular velocity can be related to the period and frequency of rotation. Angular velocity is equal to $2\pi$, which is a full rotation in terms of radians, divided by the period. The period is inversely proportional to the frequency, $$\omega = \frac{2\pi}{T} \qquad [039]$$

$$f = \frac{1}{T} \qquad [040]$$

In physics (specifically in electromagnetism) the Lorentz force (or electromagnetic force) is the combination of electric and magnetic force on a point charge due to electromagnetic fields.

$$F=q(E+v\times B) \qquad [041]$$

Since the device doesn't have an electric field, the equation is reduced down to the charge times its velocity crossed with the magnetic field.

$$F=q(v\times B) \qquad [042]$$

The magnitude of the magnetic force is shown in equation [043] as a function of $\theta$.

$$|F|=qvB \sin \theta \qquad [043]$$

Since the velocity of the charge is perpendicular to the magnetic field $\theta=90$ and sin $90=1$.

$$|F|=qvB \qquad [044]$$

These equations allow for the predetermination of specifically generated magnetic disc frequencies, power, phase and waveform shape based upon one of more of the following parameters: disc spin frequency, mass, diameter, composition, cutout configuration and degree of upper versus lower disc(s) offset. They also allow for the generation of specific magnetic frequencies, power, phase and waveform shape based upon one or more of the following parameters: magnet strength and oscillatory or rotational frequency, in addition to tube composition, thickness, segmentation and whether electrically coupled or uncoupled.

Tube Coupling Apparatus: Consists of 4 tube segments of equal length, separated by gaskets between, electrically independent of one another. Attached to each tube segment are electrical leads, which subsequently are connected to a microprocessor.

This coupling results in a method for creating a period of stimulus, the microcontroller is programmed to electrically couple and uncouple tube sections at specific rates. For example, stages of one period could be but are not limited to the following series of operations: 1) All sections electrically uncoupled 2) Top 2 sections electrically coupled 3) Top 3 tube sections coupled 4) All 4 tube sections electrically coupled 5) Top 3 tube sections coupled 6) Top 2 tube sections coupled.

In addition, short pauses or "hitches" in the rotation of either the discs or magnet, when rotating, can also generate specific tertiary frequencies and prescribed intervals. Any or all of these generated waveforms and frequencies can be incorporated into a real time feedback loop, based upon the acquisition and transmission of the subject's physiologic data.

In a general discussion of some of the laws of physics, it is known from Biot-Savart's Law, magnetic fields can induce electrical currents and electrical currents can induce magnetic fields. With the Biot-Savart Law, the magnetic field induced by the electrical current can be calculated. The magnetic field depends on the magnitude of the current, geometry of the current, and the distance from the current.

The magnetic field segment $d\vec{B}$ is equal to the permeability of free space $\mu_0$, multiplied by the current I, divided by $4\pi$, and multiplied by the cross product of the length segment d $\vec{l}$ and the directional unit vector to the point of measure divided by the distance from the current to the point of measure r. The magnitude of this equation is equal to the same equation multiplied by the sine of the angle between d $\vec{l}$ and $\hat{r}$.

$$d\vec{B} = \frac{\mu_0 I}{4\pi}\frac{d\vec{l}\times\hat{r}}{r^2} \qquad [045]$$

-continued $$|d\vec{B}| = \frac{\mu_o I \ dl \ \sin \theta}{4\pi r^2} \qquad [046]$$

Figure 20:
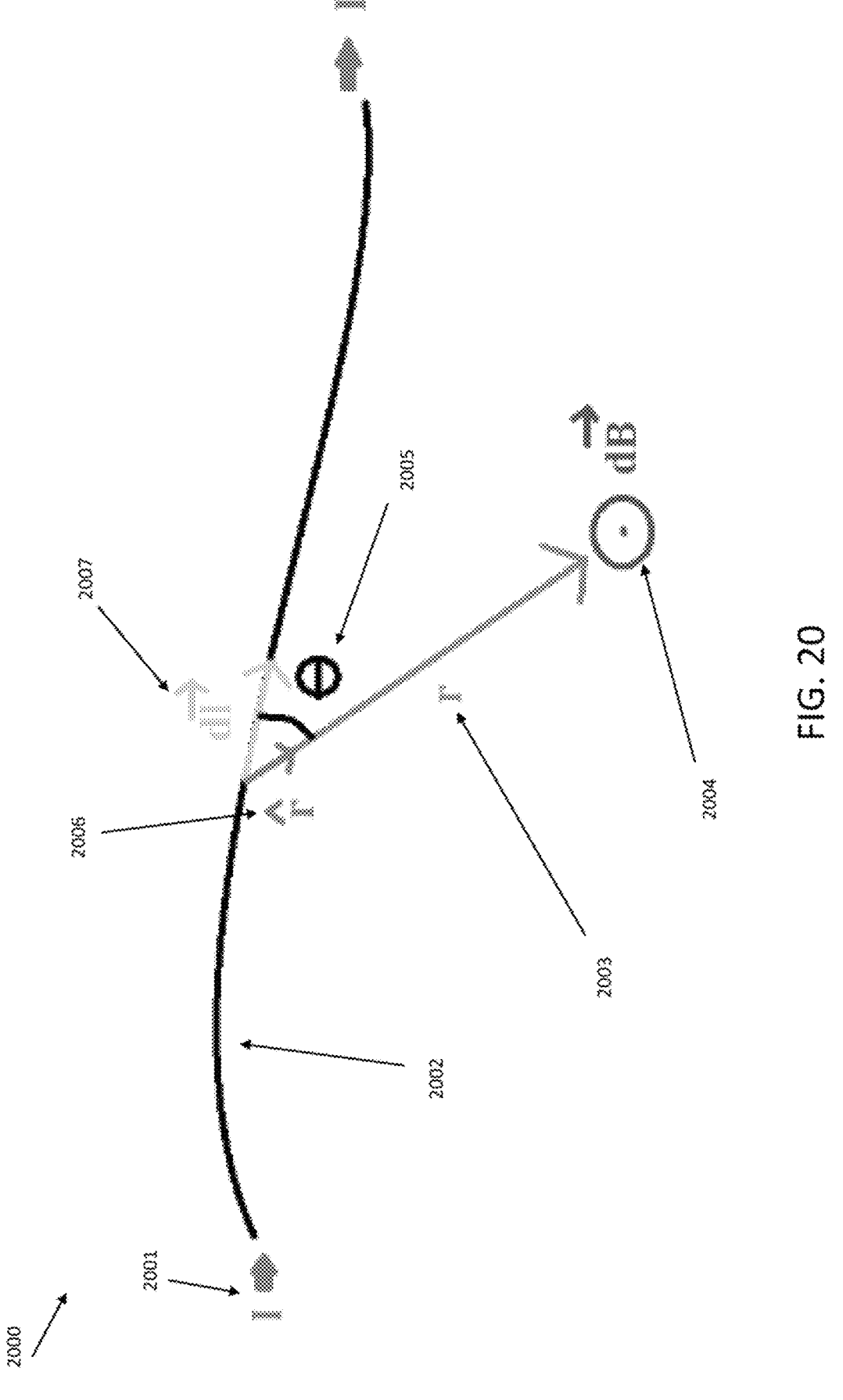
FIG. 20 depicts a mathematical illustration of a current carrying wire inducing a magnetic field.

FIG. 20 depicts a mathematical diagram of a current carrying wire inducing a magnetic field. The magnetic field strength is calculated at the point of measure 2004. 2001 is the direction of the current flowing through the wire 2002. 2003 is the distance from the wire 2002 to the point of measure 2004. 2005 is the angle between the point of measure 2004 and a segment of current carrying wire 2007. 2006 is the directional unit vector from the segment of current 2007 to the point of measure 2004.

To solve for the total magnetic field, the integration of d $\vec{B}$ must take place. The total magnetic field $B_{induced}$ is equal to the permeability of free space $\mu_0$, multiplied by the current I, divided by $4\pi$, and multiplied by the integral that describes geometry and distance. In the integral, d$\vec{s}$ is the length segment, $\hat{r}$ is the radial direction unit vector from the point of measure, and r is the distance between the length segment to the point of measure.

$$B_{induced} = \frac{\mu_o I}{4\pi} \int \frac{d\vec{s} \times \hat{r}}{r^2} \qquad [047]$$

Figure 21:
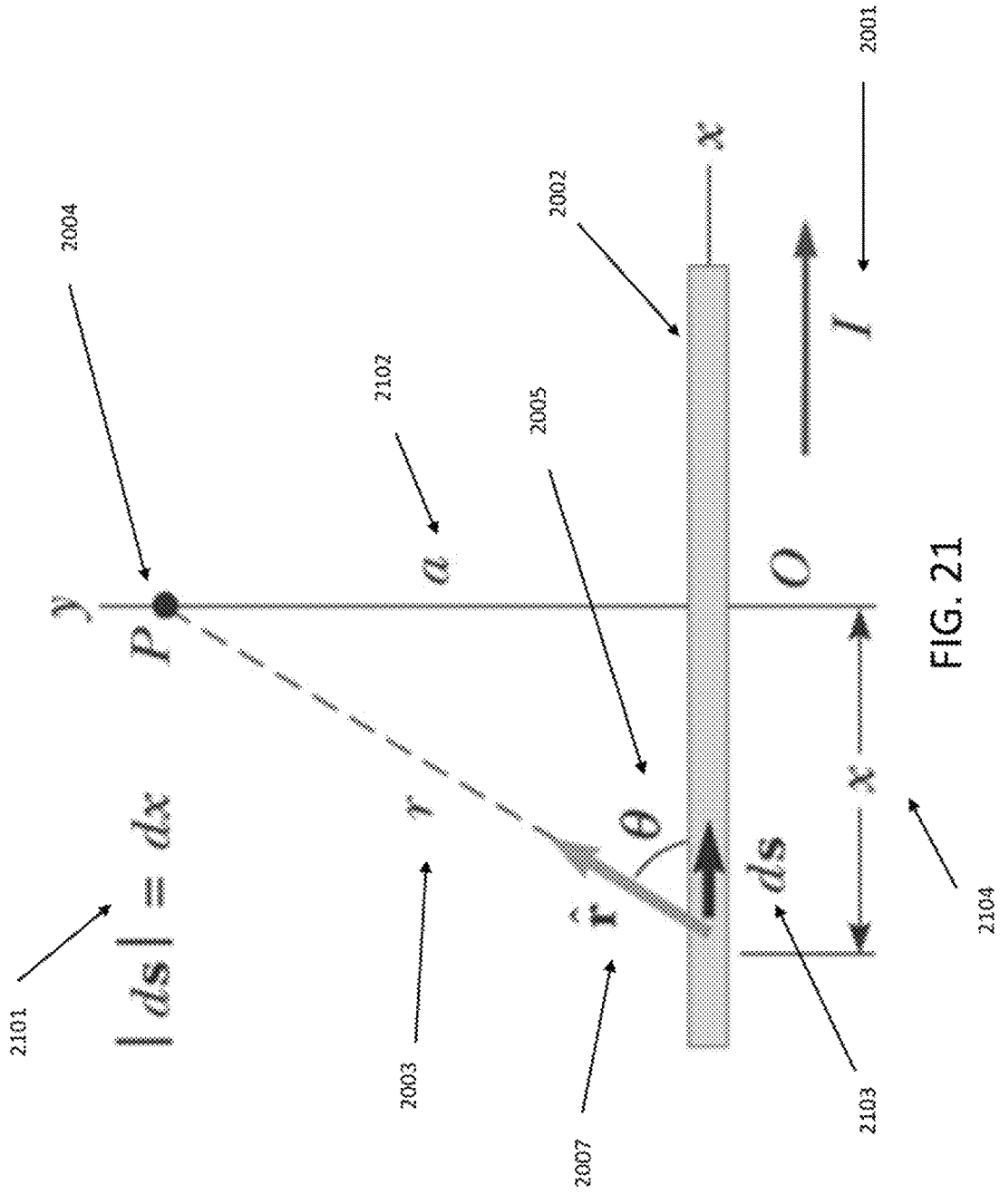
FIG. 21 depicts a mathematical illustration of a magnetic field being measured from an infinite wire.

Applying this to an infinite wire using the FIG. 21. FIG. 21 Depicts mathematical diagram of a magnetic field being measured from an infinite wire. 2101 depicts the relationship from a segment of curvature to a segment along the x axis. 2102 depicts the distance from origin to the point of measure 2004. 2103 depicts the segment of curvature on the current carrying wire 2002. 2001 depicts the current flow. 2104 is the distance from the origin to the segment of curvature 2103. 2007 is the directional unit vector to the point of measure 2004. 2003 is the distance from the segment of curvature 2103 to the point of measure 2004. 2005 is the angle between the segment of curvature 2103 to the point of measure 2004. P is the point of measure, $\alpha$ is the distance from the point of measure to the origin, and x is the distance from ds to the origin.

In the case of an infinitely long wire, the following terms can be defined using the principles of geometry and trigonometry.

$$d\vec{s} \times \hat{r} = dx \ \sin \theta \qquad [048]$$

$$x = \frac{a}{\tan \theta} \qquad [049]$$

$$dx = -\frac{a \sec^2 \theta}{\tan^2 \theta} d\theta \qquad [050]$$

$$dx = -\frac{a}{\sin^2 \theta} d\theta \qquad [051]$$

$$d\vec{s} \times \hat{r} = -\frac{a}{\sin \theta} d\theta \qquad [052]$$

$$\sin \theta = \frac{a}{r} \qquad [053]$$

$$\frac{1}{r^2} = \frac{\sin^2 \theta}{a^2} \qquad [054]$$

$$\frac{d\vec{s} \times \hat{r}}{r^2} = \frac{-\frac{a}{\sin \theta}}{\frac{\sin^2 \theta}{a^2}} d\theta \qquad [055]$$

-continued $$\frac{d\vec{s} \times \hat{r}}{r^2} = -\frac{\sin \theta}{a} \qquad [056]$$

$$d\vec{B} = -\frac{\mu_o \ I}{4\pi a} \sin \theta \ d\theta \qquad [057]$$

$$B_{induced} = -\frac{\mu_o I}{4\pi a} \int_{\theta_1}^{\theta_2} \sin \theta \ d\theta \qquad [058]$$

$$B_{induced} = \frac{\mu_o I}{4\pi a} [\cos \theta_1 - \cos \theta_2] \qquad [059]$$

Since we are integrating on an infinitely long straight wire, $\theta_1 = 0$ and $\theta_2 = \pi$. Therefore, the magnetic field induced is shown in equation [060].

$$\therefore B_{induced} = \frac{\mu_o I}{2\pi a} \qquad [060]$$

Figure 22:
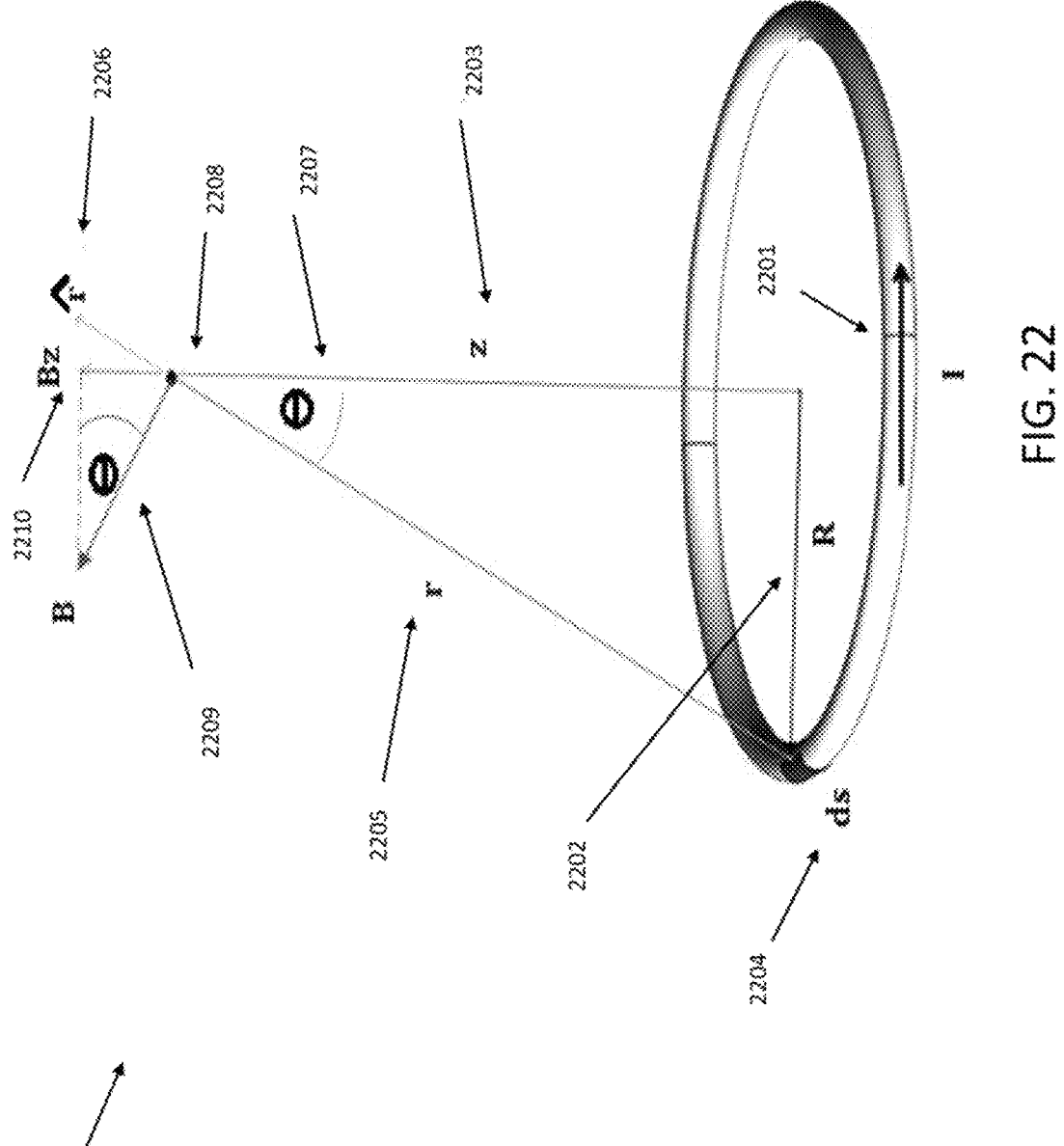
FIG. 22 depicts a mathematical illustration of a loop carrying wire producing a magnetic field.

The Biot-Savart Law can also be applied to a loop of current. It is assumed that the magnet in the device is inducing an eddy-current that loops around the radius of the magnet. The eddy-current is inducing a magnetic field coming out of the conducting disk. Applying the Biot-Savart Law to the loop around the radius of the magnet, we can calculate the induced magnetic field from a distance away from the current carrying loop along its axis. Applying the Biot-Savart Law to a ring of current, FIG. 22 depicts a mathematical diagram of a loop carrying wire producing a magnetic field. In this figure, there is a loop of wire carrying electrical current depicted by 2201. 2202 depicts the radius of the loop and 2203 depicts the axial distance from the center of the loop to the point of measure 2208. 2204 depicts a segment of curvature in the current carrying loop. 2205 depicts the distance from the point of measure 2208 to the segment of curvature 2204. The directional unit vector is depicted by 2206 from the segment of curvature 2204. 2207 depicts the angle from the axis to the current carrying loop 2201. 2209 depicts the magnetic field at a given segment of curvature whereas the total magnetic field is depicted by 2210.

Using geometry and trigonometry, $dB_z$ can be rewritten in terms of r and $\theta$.

$$B_{induced} = \int dB_z = \frac{\mu_o I}{4\pi} \int \frac{ds}{r^2} \sin \theta \qquad [061]$$

$$r^2 = R^2 + z^2 \qquad [062]$$

$$\sin \theta = \frac{R}{r} = \frac{R}{\sqrt{R^2 + z^2}} \qquad [063]$$

The equation reduces down to the integral of ds which is the circumference of the loop.

$$\int_0^R dS = 2\pi R \qquad [064]$$

$$\therefore B_{induced} = \frac{\mu_o I}{2} \frac{R^2}{(R^2 + z^2)^{\frac{3}{2}}} \qquad [065]$$

In the case of the spinning conducting disk. The frequency of the disk is directly related to the total current induced. The faster the disk spins, the stronger the current induced will become. The strength of the current induced is proportional to the strength of the magnetic field.

Figure 23:
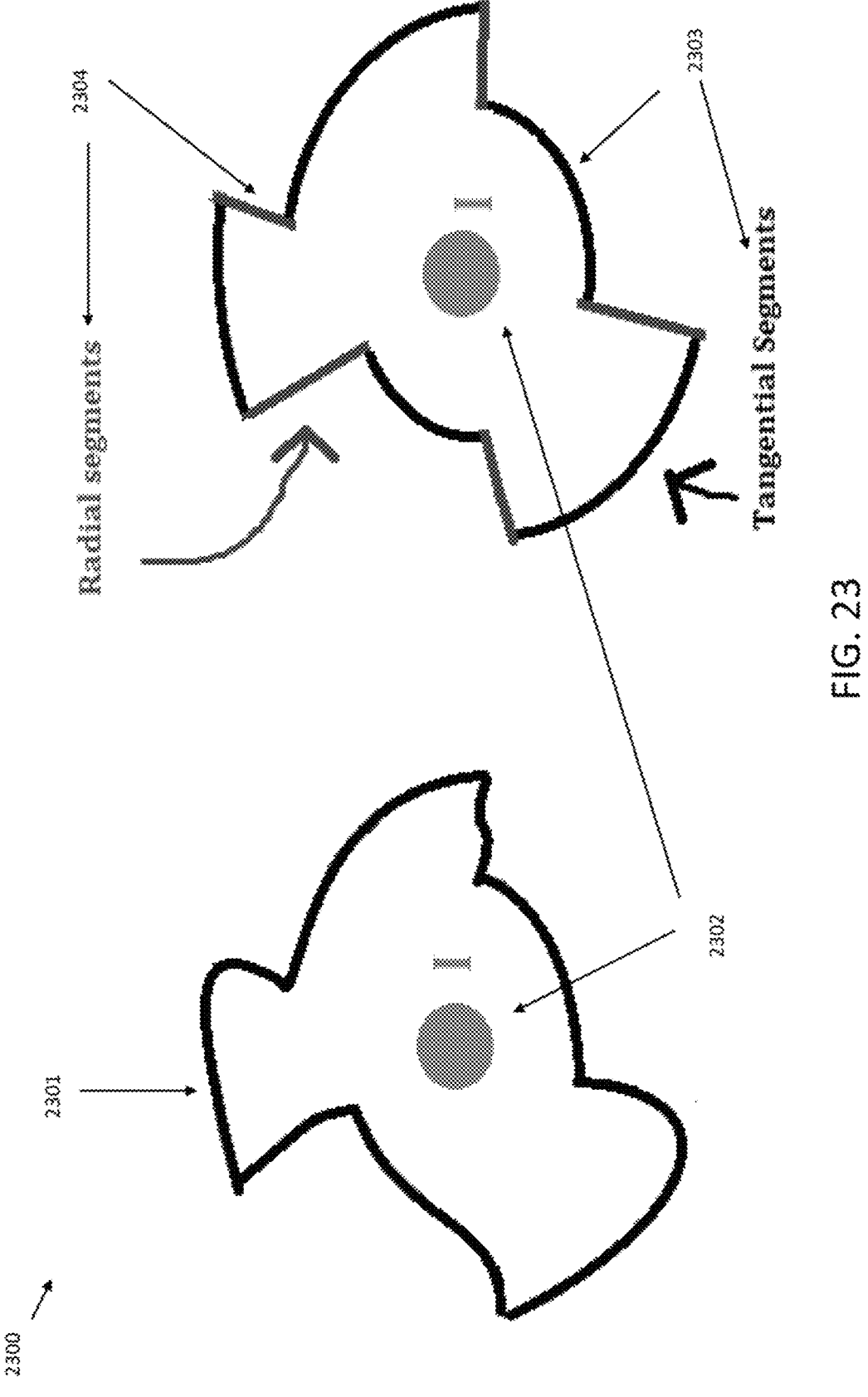
FIG. 23 depicts an area around a current carrying wire used to explain ampere's law.

In a discussion of Amperes Law, in classical electromagnetism, Ampere's circuital law relates the integrated magnetic field around a closed loop to the electric current passing through the loop. When defining the integral around the current carrying wire, the only components that matter are the tangential segments of the integral. FIG. 23 depicts an area around a current carrying wire. The area is used to explain ampere's law. 2301 depicts the closed loop around the current carrying wire 2302. The tangential segments of the area depicted by 2303 and the radial segments are depicted by 2304.

$$\oint \vec{B} \cdot d\vec{l} = \qquad [066]$$

$$\sum_{segments}\left(\int \vec{B} \cdot d\vec{l}\right) = \sum_{\substack{radial \\ segments}}\left(\int \vec{B} \cdot d\vec{l}\right) + \sum_{\substack{tangential \\ segments}}\left(\int \vec{B} \cdot d\vec{l}\right)$$

$$\sum_{\substack{radial \\ segments}}\left(\int \vec{B} \cdot d\vec{l}\right) = 0 \qquad [067]$$

$$\therefore \oint_{Loop} \vec{B} \cdot d\vec{l} = \mu_o I_{enclosed} \qquad [068]$$

With the magnetic field being induced within the conducting disk and the magnetic field being produced by the permanent magnet. The total magnetic is the resultant of the summation of all the magnetic fields involved. $B_i$ is the magnetic field of a component in the device and n is the number of magnetic fields. This is shown in FIG. 24.

$$B_{total} = \sum_{i=1}^{n} B_i \qquad [069]$$

Figure 24:
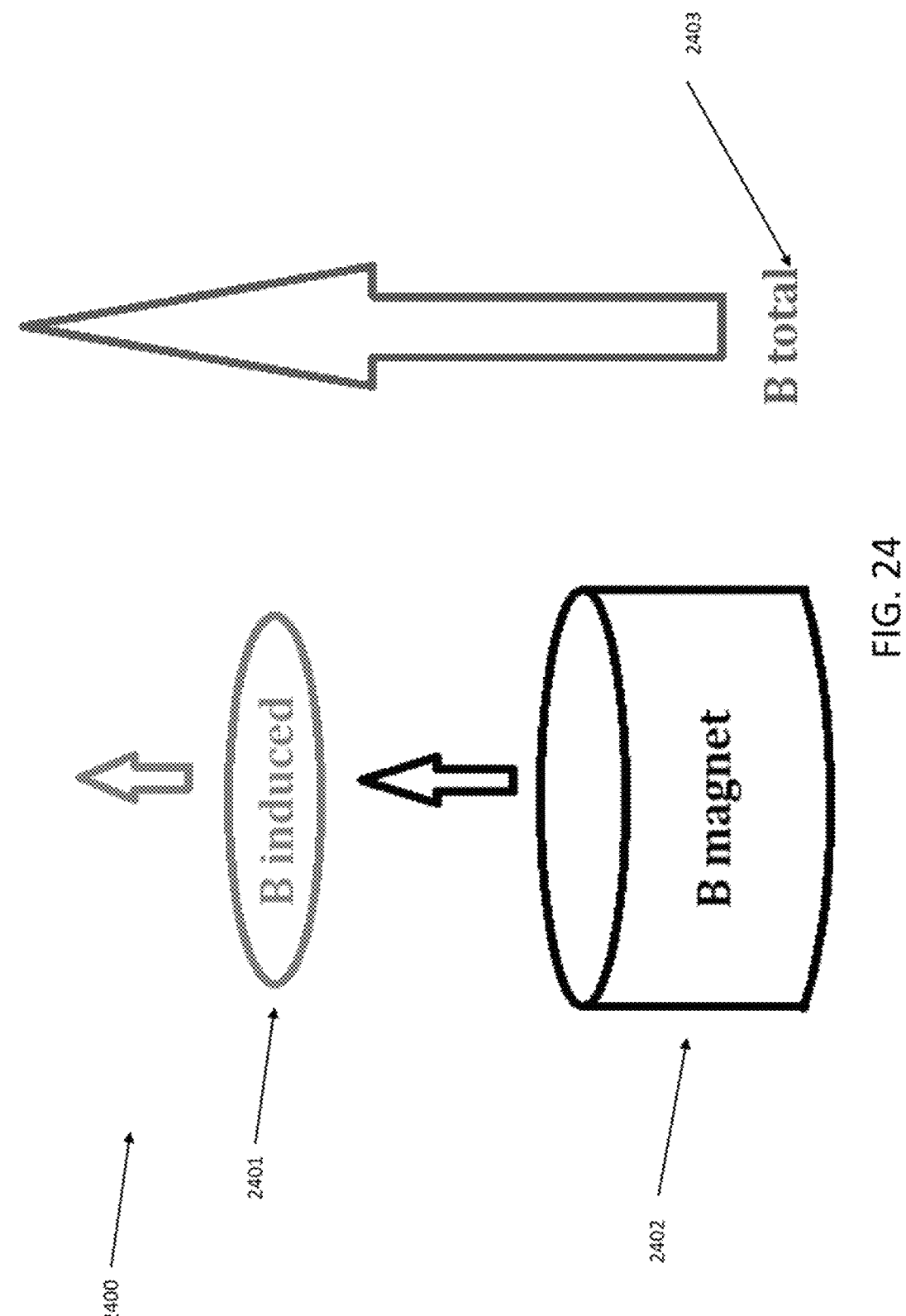
FIG. 24 depicts an illustration representing additive magnetic fields involved in the physics of the present invention.

FIG. 24 depicts a diagram representation of additive magnetic fields. The magnetic field induced by the eddy-current is depicted by 2401 and the magnetic field produced by the permanent is depicted by 2402. The additive magnetic field is represented by 2403.

Relating the underlying science from above the apparatus as disclosed above in the embodiment, we show how to calculate the induced magnetic force where the induced current must be calculated or measured first; since measuring the current is not generally possible, we disclose a method for calculating the current. The calculation starts with the Lorentz force on an electron.

$$F_L = qvB \qquad [070]$$

The velocity of the electron is assumed the be the tangential velocity of the disk which is derived from the angular velocity of the disk multiplied by the radial distance to the edge of the disk.

$$v = \omega r \qquad [071]$$

The angular velocity can be calculated from the frequency of the disk multiplied by $2\pi$.

$$\omega = 2\pi f \qquad [072]$$

The force of an electric potential is proportional to the charge and the radial derivative of voltage.

$$F_E = qE = q\frac{dV}{dr} \qquad [073]$$

The Lorentz forces and electric potential forces are at equilibrium and can be set equal to each other.

$$F_L = F_E \qquad [074]$$

$$q\omega rB = q\frac{dV}{dr} \qquad [075]$$

$$\frac{dV}{dr} = \omega rB \qquad [076]$$

The voltage derivative can then be integrated to find the emf induced in terms of magnetic field, radius, and angular velocity.

$$emf = \int_0^R \omega B r \, dr \qquad [077]$$

$$emf = \frac{\omega B r^2}{2} \qquad [078]$$

At a frequency of 0.5 Hz and an external magnetic field of 4.5 milli-tesla and a disk with radius 5.25 inches, the emf is calculated in the following equations.

$$emf = \frac{3.14\left(\frac{rad}{s}\right)4.5(mT)0.133(m)}{2} \qquad [079]$$

$$emf = 0.126 \text{ mV} \qquad [080]$$

Once the emf induced in the disk is known, current through the disk is calculated. Current can be calculated from Ohm's law. I is the current, V is the voltage, and $R_\Omega$ is the resistance.

$$I = \frac{V}{R_\Omega} \qquad [081]$$

$$I = \frac{emf}{R_\Omega} \qquad [082]$$

The resistance of a wire is known to be calculated by the following equation.

$$R_\Omega = \frac{\rho}{A}\int dl \qquad [083]$$

Where $R_\Omega$ is the resistance of a wire, $\rho$ is the resistivity of the material of the wire, A is the cross-sectional area of the wire, and L is the length of the wire. The line integral for a wire is the length L of the wire.

$$R_\Omega = \frac{\rho L}{A} \qquad [084]$$

In the case of a rotating conductive disk, the cross-sectional area and the length of the current in the rotating disk is difficult to calculate without numerical method representation. It is difficult to predict the exact path of the current inside the conducting disk. The resistance of the disk was imperially measured with a volt-ohm meter to be $0.01\Omega$. Once the overall resistance is known, the current induced can be calculated.

$$I = \frac{0.126 \text{ mV}}{0.01 \text{ }\Omega} \qquad [085]$$

$$I = 0.013 \text{ }(A) \qquad [086]$$

The magnetic field can now be calculated.

To calculate the magnetic field in a current carrying wire the equation is derived from the Biot-Savart Law. The magnetic field segment $d\vec{B}$ is equal to the permeability of free space $\mu_0$, multiplied by the current I, divided by $4\pi$, and multiplied by the cross product of the length segment $d\vec{l}$ and the directional unit vector to the point of measure divided by the distance from the current to the point of measure r.

$$d\vec{B} = \frac{\mu_o I}{4\pi} \frac{d\vec{l} \times \hat{r}}{r^2} \qquad [087]$$

Applying the Biot-Savart Law to a loop of current seen in FIG. 22 the equation can be rewritten in terms of r and $\theta$ using geometry and trigonometry.

$$B_{induced} = \int dB = \frac{\mu_o I}{4\pi} \int \frac{ds}{r^2} \sin \theta \qquad [088]$$

$$r^2 = R^2 + z^2 \qquad [089]$$

$$\sin \theta = \frac{R}{r} = \frac{R}{\sqrt{R^2 + z^2}} \qquad [090]$$

The equation reduces down to the integral of ds which is the circumference of the loop.

$$\int_0^R ds = 2\pi R \qquad [091]$$

$$\therefore \ B_{induced} = \frac{\mu_o I}{2} \frac{R^2}{\left(R^2 + z^2\right)^{\frac{3}{2}}} \qquad [092]$$

Plugging in the values for a distance of an inch above the disk.

$$B_{induced} = \frac{4\pi * 10^{-7}\left(\frac{Tm}{A}\right) * 0.013 \text{ }(A)}{2} \frac{0.133^2 (m)^2}{\left(0.133^2 + 0.0254^2\right)^{\frac{3}{2}}} \qquad [093]$$

$$B_{induced} = 0.06 \text{ }\mu T \qquad [094]$$

The field induced by the current induced in the disk for 0.5 Hz is 0.06 micro tesla.

Figure 25:
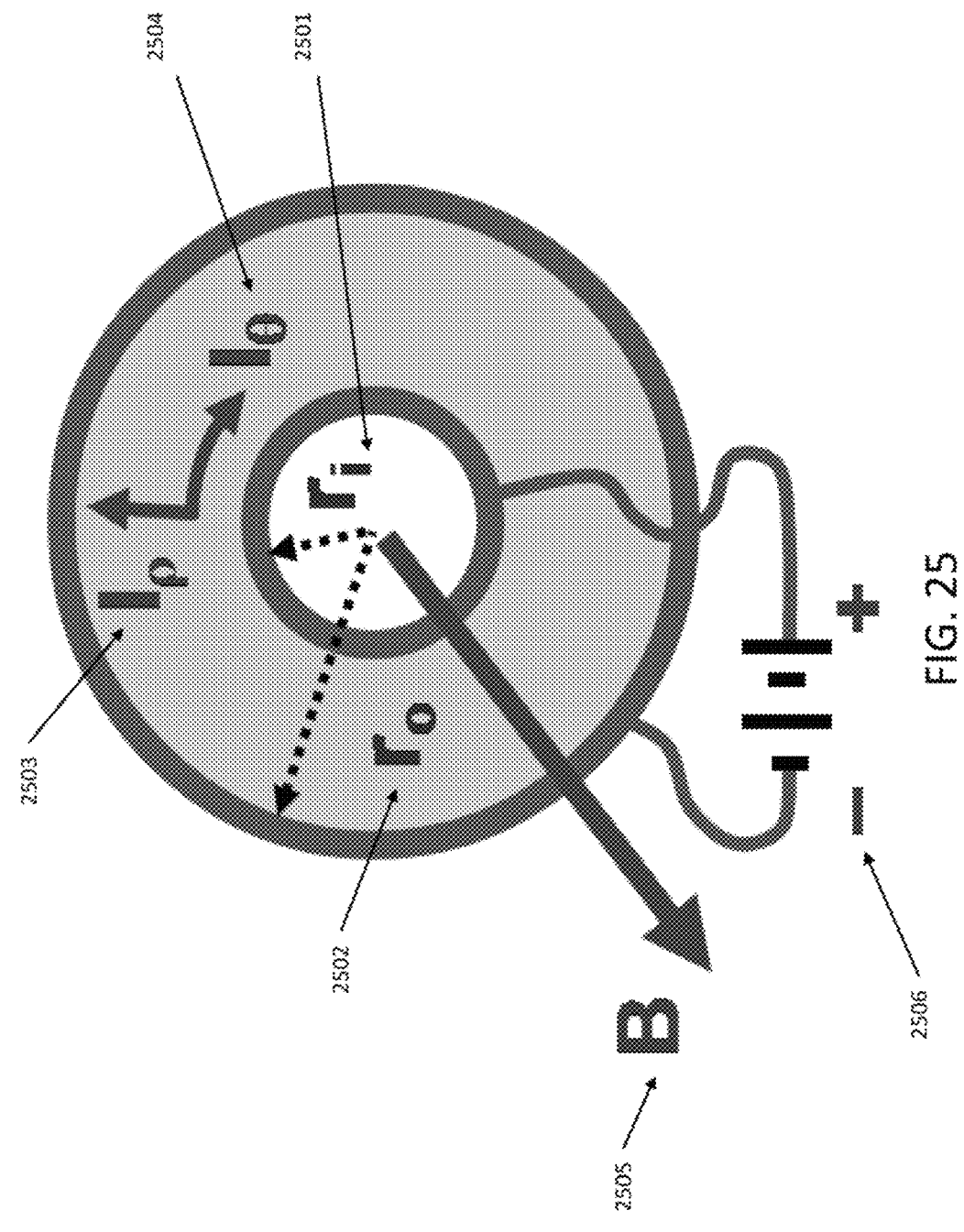
FIG. 25 depicts an illustration of a corbino disk which is a conducting annulus with perfectly conducting rims used to explain magnetoresistance.

Magnetoresistance is the tendency of a material to change the value of its electrical resistance in an externally applied magnetic field. An example of magnetoresistance due to direct action of magnetic field on electric current can be studied on a Corbino disk (FIG. 25). It consists of a conducting annulus with perfectly conducting rims. Without a magnetic field 2505, the battery 2506 drives a radial current 2503 between the inner rim 2501 and outer rim 2502. When a magnetic field 2505 perpendicular to the plane of the annulus is applied, (either into or out of the page) a circular component of current 2504 flows as well, due to Lorentz force.

FIG. 25 In a semiconductor with a single carrier type, the magnetoresistance is proportional to $1+(\mu B)^2$. Where B is the magnetic field and $\mu$ is the electron mobility. To understand the physics behind a faraday disk, an analysis of the corbino disk is useful.

In examination of the Corbino disk, as calculated before, the radial induced emf on a conductive disk from the center of the disk to the edge of the disk is shown in equation [095].

$$emf_{radial} = \tfrac{1}{2}\omega B r^2 \qquad [095]$$

To calculate the circular emf, the motion of the electrons is considered. J is the electric current density per unit area. I is the current and A is the cross-sectional area of the current. The current density is the amount of current that can flow through the cross-sectional area of a wire or conductor $$J = \frac{I}{A} \qquad [096]$$

For electric current in a copper wire, the charge carriers are the mobile electrons and the positively charged copper ions are essentially stationary in the metal lattice. Drift velocity is the velocity at which the electrons move through a conductor or wire. The drift velocity of electrons through copper wires is very slow. It is the change or "signal" which propagates along wires near the speed of light. The radial drift velocity can be calculated since it is directly proportional to the current and inversely proportional to the number of free electrons, the charge of a single electron, and the cross-sectional area of the current A.

$$v_{drift} = \frac{I}{n q_e A} \qquad [097]$$

The circular emf induced around a circle of radius r is given by the following equation.

$$emf_{circular} = \varphi_0^{2\pi r} (v_{drift} \times B) \cdot dr \qquad [098]$$

The circular emf is equal to the radial current $I_{radial}$ multiplied by the magnetic field B divided by the thickness of the disk s, the number of electrons n and the charge on a single electron $q_e$.

$$emf_{circular} = \frac{I_{radial} B}{s n q_e} \qquad [099]$$

The circular current flowing in a circular strip of radius r and a section of s·dr can be calculated by the following equation. In this equation $\rho$ is the electric resistivity of the material.

$$dI_{circular} = \frac{emf_{circular} \ s \ dr}{p \ 2 \ \pi \ r} \qquad [100]$$

$$dI_{circular} = \frac{\mu B}{2\pi} I_{radial} \frac{dr}{r} \qquad [101]$$

The electron mobility relation is inversely proportional to the electric resistivity of the material $\rho$ the number of electrons n and the charge of a single electron $q_e$.

$$\mu = \frac{1}{\rho n q_e} \quad [102]$$

The total circular current $I_{circular}$ is given by the following equation. In this equation, $r_1$ and $r_2$ are the inner and outer radius of the disk.

$$I_{circular} = \frac{\mu B}{2\pi} I_{radial} \ln \frac{r_2}{r1} \quad [103]$$

The power dissipated in the disk comes from ohms law.

$$W_{dissipated} = (I^2 R)_{radial} + (I^2 R)_{circular} \quad [104]$$

The following equation shows that the phenomenon may be described as due to an increased resistance as a result of the magnetoresistance effect.

$$W_{dissipated} = I_{radial}^2 R_{radial}(1 + \mu^2 B^2) \quad [105]$$

The following two equations are the circular and radial resistances derived from equation [083].

$$R_{radial} = \frac{\rho}{2\pi s} \ln \frac{r_2}{r_1} \quad [106]$$

$$R_{circular} = \frac{\rho^2}{s^2} \frac{1}{R_{radial}} \quad [107]$$

Considering a Faraday disc in which the circular symmetry is conserved. As shown above, the steady condition will be characterized by the flow of a radial and of a circular current. The mechanical power needed to keep the disc rotating with constant angular velocity $\omega$ is equal to the work per unit time done by the magnetic field on the rotating radial currents.

$$W_{mechanical} = \int_0^{2\pi} \int_{r_1} r^2 (J_{radial} r s d\theta)(B dr)(\omega r) \quad [108]$$

$$W_{mechanical} = I_{radial} \frac{1}{2} \omega B(r_2^2 - r_1^2) \quad [109]$$

$$W_{mechanical} = I_{radial} emf_{radial} \quad [110]$$

Figure 26:
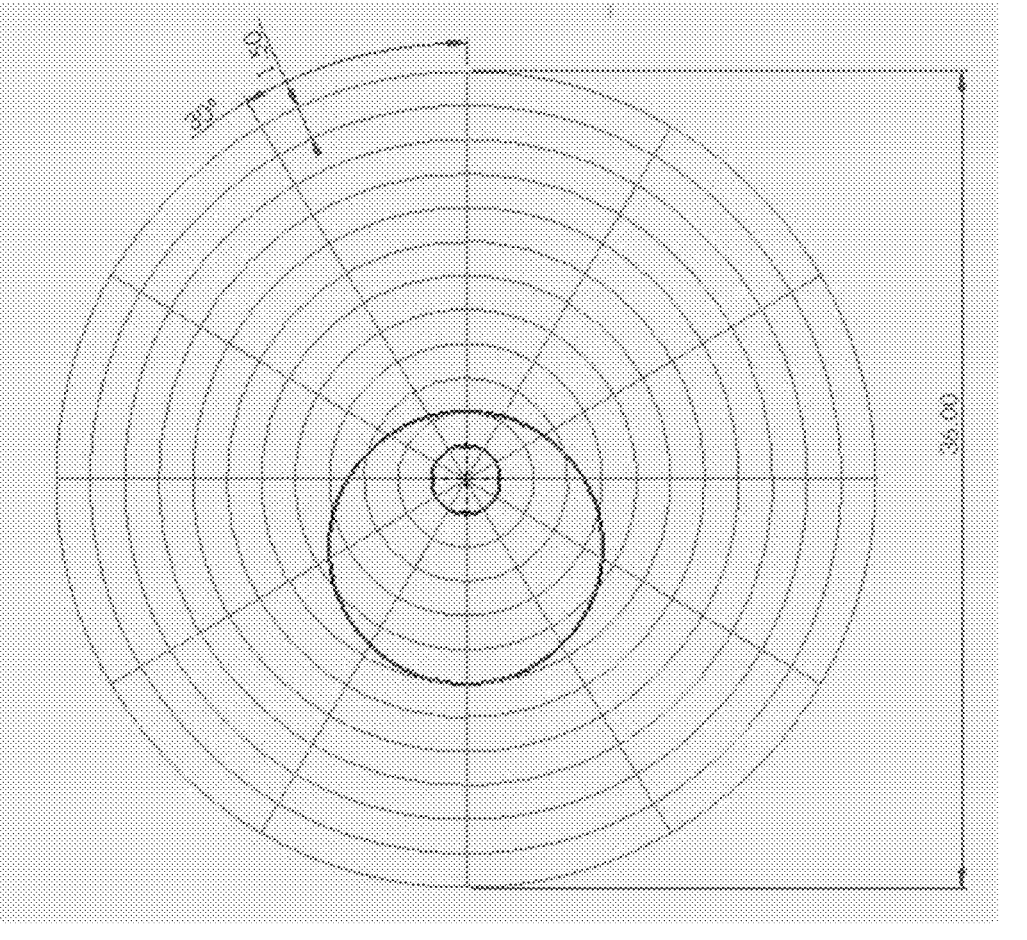
FIG. 26 depicts an illustration of the test grid that was used for the testing of the present invention

In order to better understand the capabilities of the test apparatus device as well as how it functions, a series of tests were performed. The setup of these tests featured the device place on a custom circular testing grid that is centered around the center of the neodymium magnet that is located within the device. The test apparatus device was aligned on the grid such that the point on the exterior edge of the device with the least distance to the center of the magnet is collinear with 0° on the grid. An illustration of this grid can be seen in FIG. 26.

Figure 27:
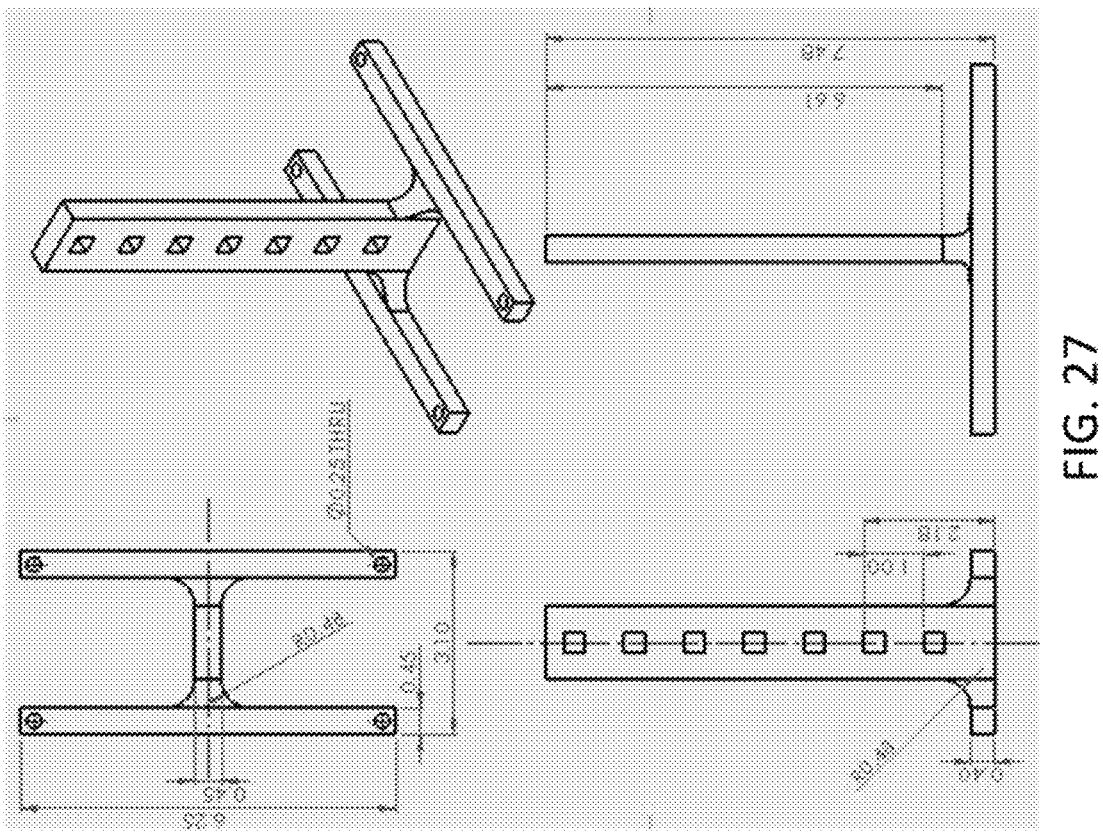
FIG. 27 depicts an illustration of the magnetic probe stand that was 3D printed and used for the testing of the present invention.
Figure 27:

Included with the test apparatus device and the grid, a Vernier Go Direct 3 Axis Magnetic Probe along with Vernier's Graphical Analysis 4 software were used to gather information about the magnetic field and magnetic pulses the device produces. A custom stand was designed, 3-D printed and used to position the magnetic probe over the course of the testing. Drawings of the custom probe stand can be seen in FIG. 27. The setup of the test featuring the test apparatus device, Test Grid, custom 3-D printed probe stand, and Vernier 3 Axis Magnetic Probe can be seen pictured in FIG. 28. Graphical Analysis 4 software was used for this test.

Upon preliminary testing it was discovered that there were some issues using the Vernier probe when measuring in the +/−5 mT range. The amplifiers within the probe displayed phase inversion as well as amplitude saturation. Thus, for better reliability of data, all tests were carried out using the measurement range of +/−130 mT.

The test apparatus device is outfitted with different configurations that it can be formatted to run with. Each configuration sets the start position of the disks that are within the device, the frequency at which these disks spin, the frequency at which the magnet rotates and lastly when the magnet is to rotate or oscillated from a position of +90° to −90°. A breakdown of each of configurations used for each test can be seen in FIG. 30.

For each test that was performed, at each point of measure data was collected for 120 seconds for total of 3 trials. Each of these trials were then averaged for the length of one cycle (4 seconds). Power spectral analysis was then performed by performing a Fast-Fourier Transform on the data transferring the data from each trial to the power range and frequency domain. The three resulting FFT's were then averaged and RMS power analysis was performed using Parseval's theorem to calculate the overall power produced by each signal. These power values were then used to compare the outcomes of different protocols that the test apparatus device can perform. Along with this a Welch Power Spectral Density Estimate was performed on the same data. Welch Power Spectral Density Estimates utilize windows and filters to help clear out noise that may be present in one's data, allowing one to solely see the frequencies present in their data. However, by using filters and windows reduces the overall power that is present in the signal. Thus, Welch Power Spectral Density Estimate only was used as a tool for the comparison on frequencies present in a signal. Quantitative power analysis was not conducted using the results from a Welch Power Spectral Density estimate.

Figure 29:
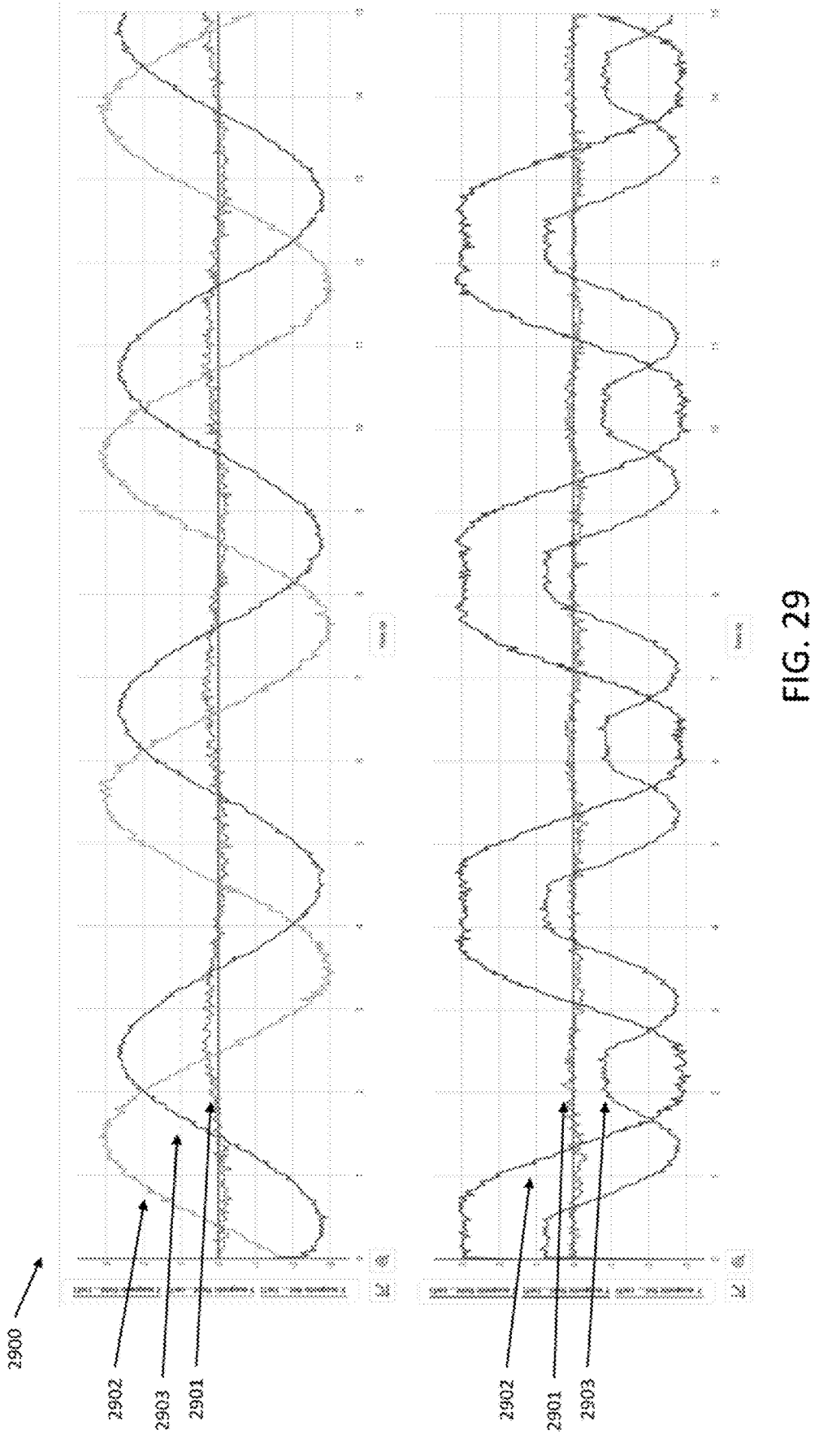
FIG. 29 depicts a waveform graph of the magnetic fields produced by the present invention through experimental testing.
Figure 42:
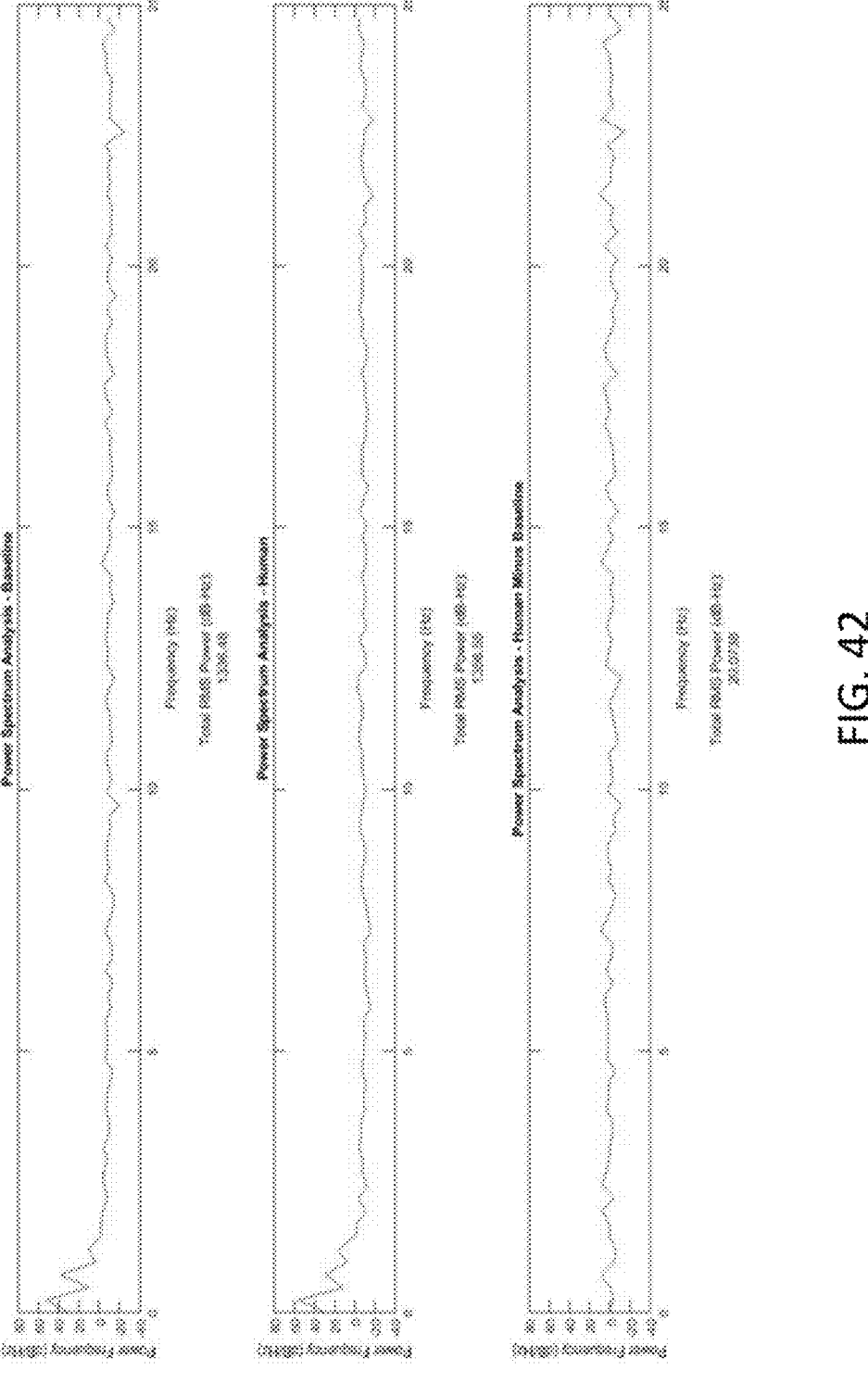
FIG. 42 depicts graphs of the net power spectrum analysis of the experimental magnetic field results for a test protocol with the device operating in the presence of a human subject, not in the presence of the human and difference between the two scenarios.

The following discussion addresses the waveforms Produced by Test Apparatus device. The first unique characteristic noted was when analyzing the data in the time domain and not performing any power spectral analysis on the signal. For this the magnetic probe was place 4.5" away from the center of the magnet that lies within the device and 4" up from the surface of test. The test apparatus the ran Test protocol 1 & 2, a description of these protocols is outlined in FIG. 42. Data was then gathered and analyzed for each protocol. It was found when the device has the magnet rotate it produces a sinusoidal signal in the X, Y & Z directions. When the Magnetic oscillates from +90 degrees to −90 degrees the device produces a repeating non-sinusoidal signal in the X, Y & Z directions. The waveforms produced for each of these cases can be seen on in FIG. 29. In FIG. 29, label 2901 corresponds to the magnetic field in the x direction. 2902 corresponds to the magnetic field in the y direction. 2903 corresponds to the magnetic field in the z direction.

Figure 31:
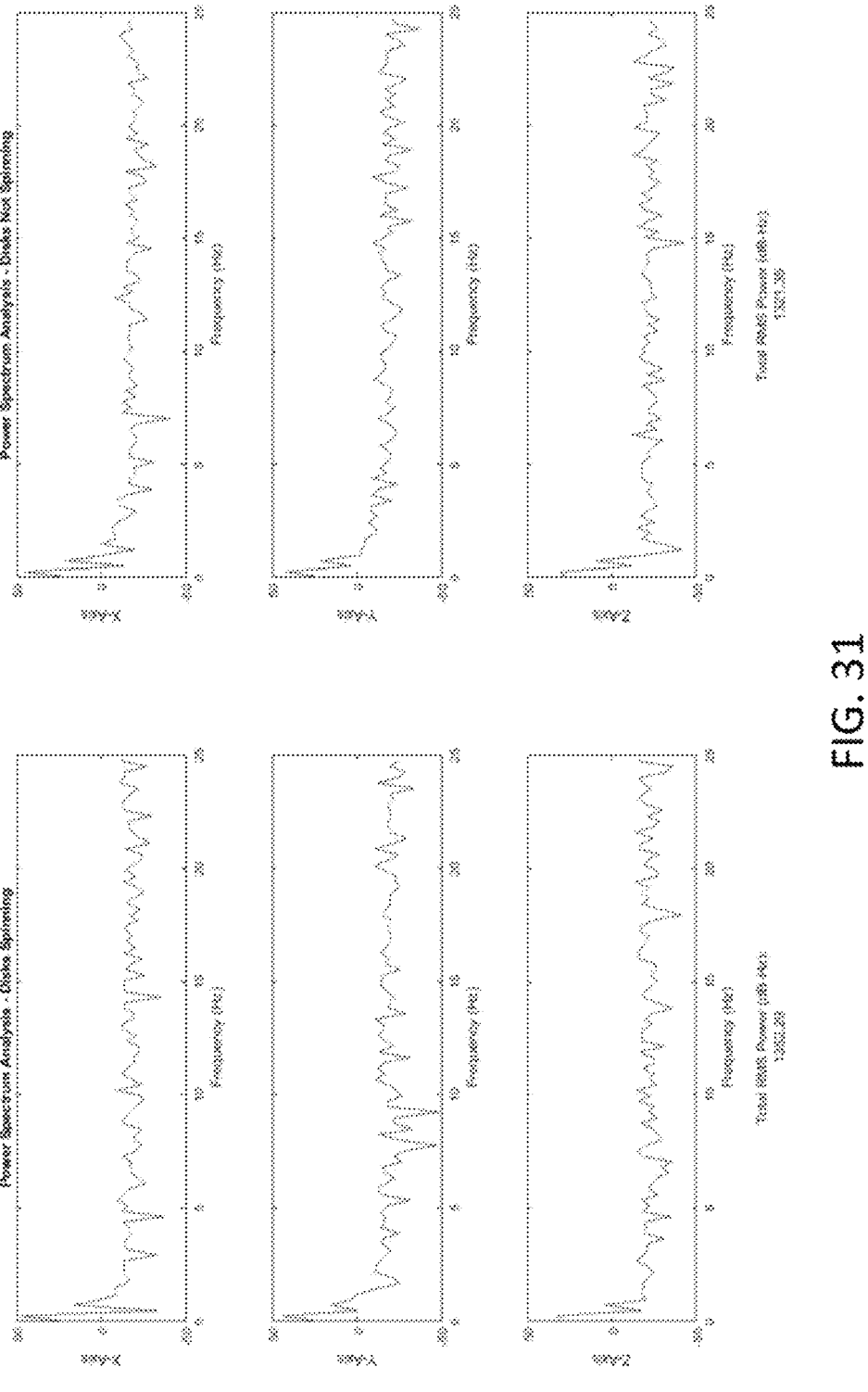
FIG. 31 depicts graphs of the Fast Fourier Transform analysis of the experimental magnetic field results for a test protocol.
Figure 32:
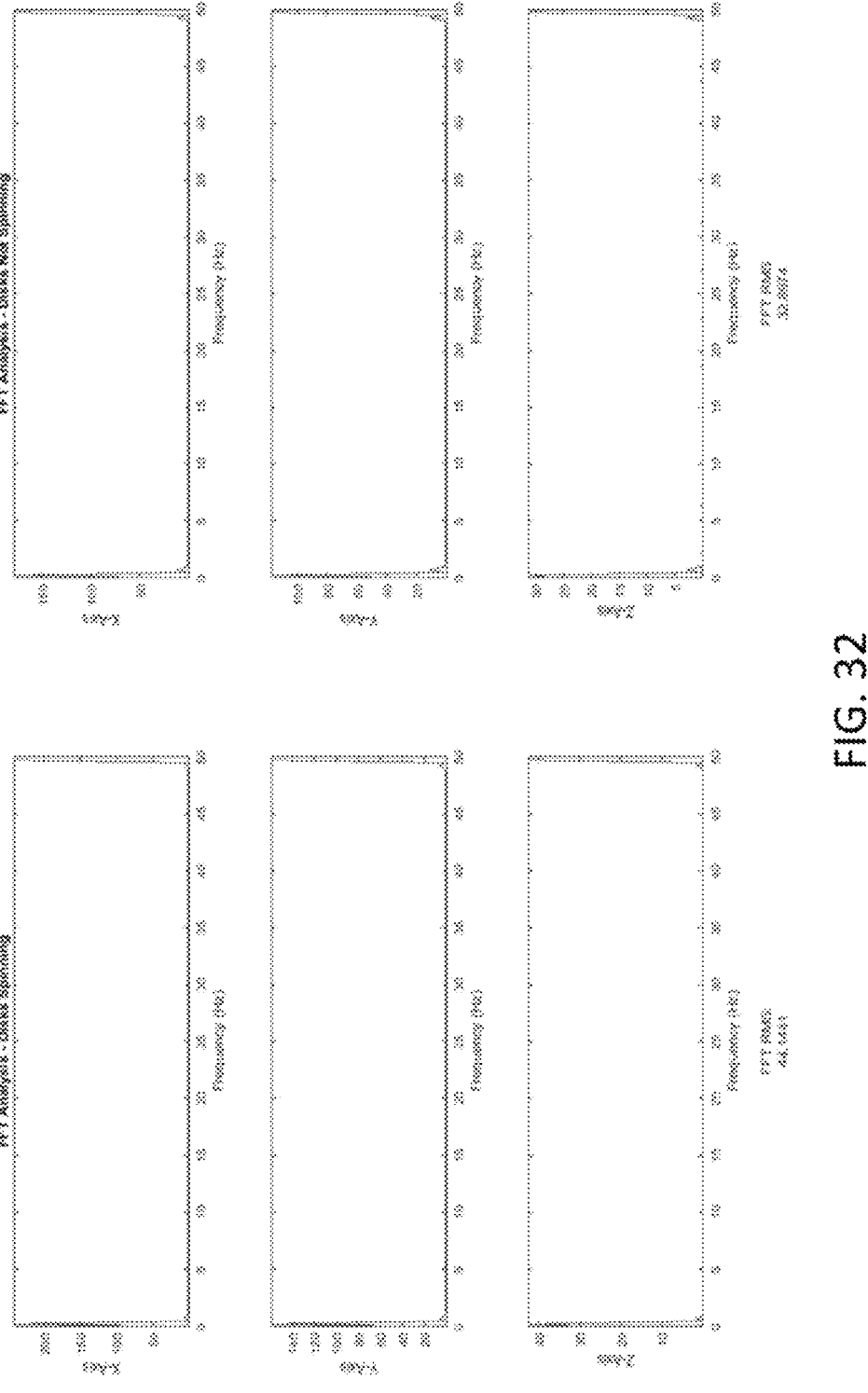
FIG. 32 depicts graphs of the Fast Fourier Transform analysis for the first and second cycle of the experimental magnetic field results from FIG. 31.

Non-ferrous Disks Spinning & Not Spinning. The next aspect of the test apparatus device that was tested was the power spectrum that the device produces when the non-Ferrous disks within the device are spinning and not spinning. This was done to determine their effect on the magnetic field produced by the test apparatus device. For this Test protocol 1 and 3 were analyzed (refer to FIG. 30 for protocol description). The magnetic probe was placed 4.5" inches away from the center of the magnet and 4" up from the test surface. Data was then gathered and analyzed for each protocol. When looking at the data in the time domain there was no significant different between the magnitudes of the signal produced. However, when looking at the Power Spectrum that the test apparatus device produced, there was a clear difference. When the non-ferrous disks within the device spin, it causes the amplitude of the signal at the frequency at which the magnet rotates to increase and the total power present in the signal to increase. This is depicted in both FIGS. 31 and 32.

Figure 33:
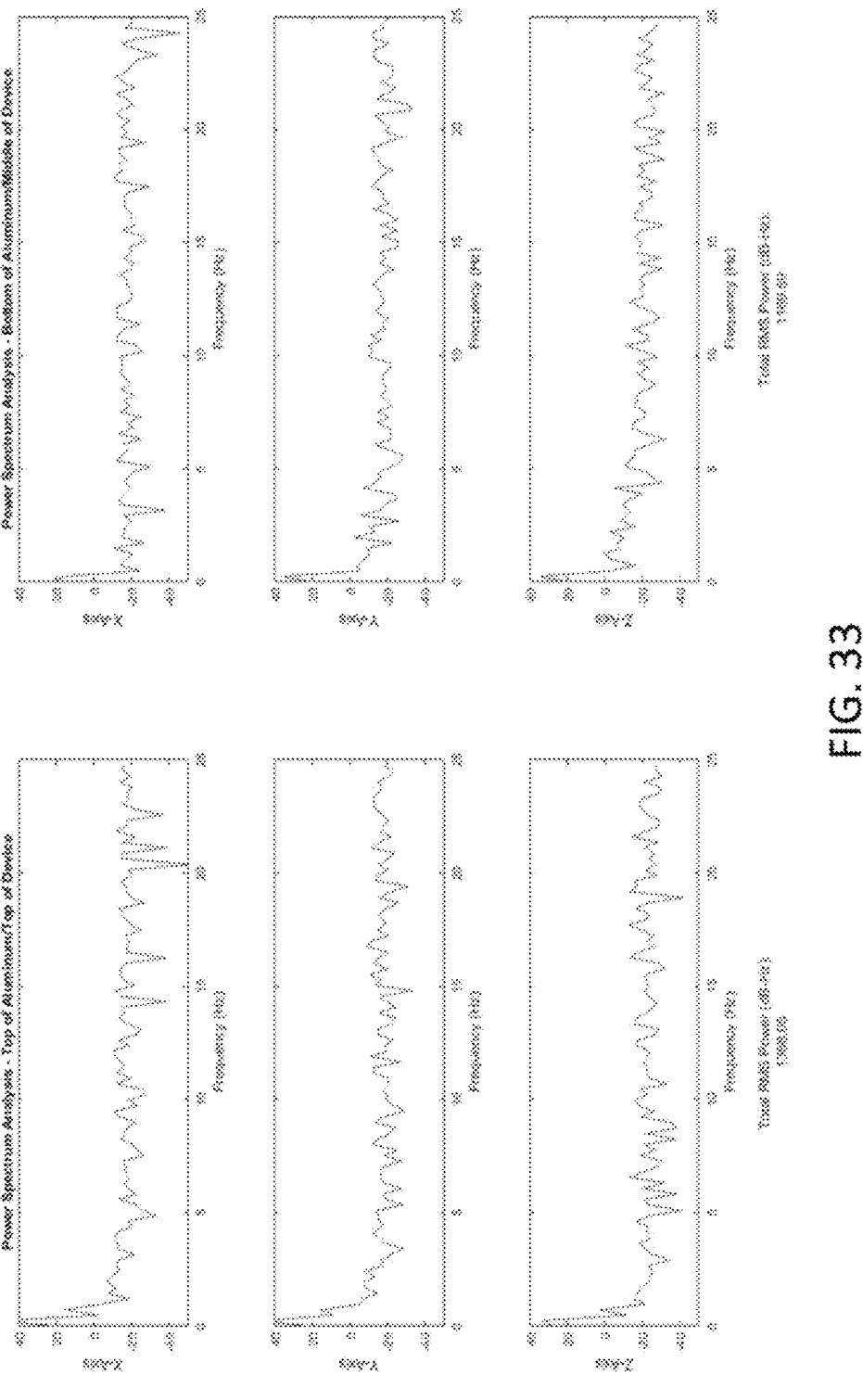
FIG. 33 depicts graphs of the Fast Fourier Transform analysis of the experimental magnetic field results for a test protocol measuring from different distances.
Figure 34:
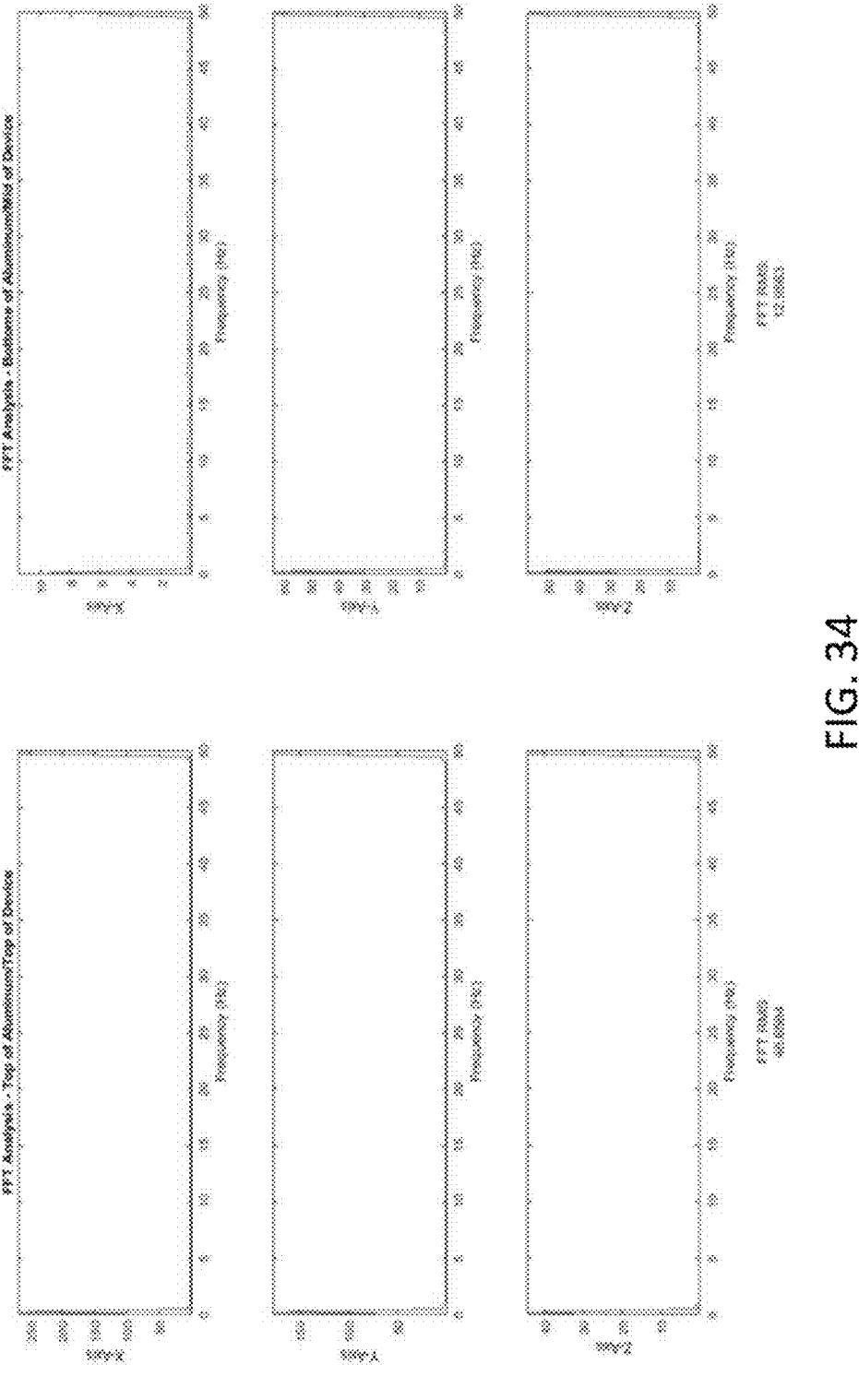
FIG. 34 depicts graphs of the Fast Fourier Transform analysis for a test protocol measuring from different heights from FIG. 33.

Eddying Effect. The next aspect of the test apparatus device was test was taking a look at the various power spectrums that the device produces at different heights. For this Test protocol 1 was analyzed (refer to FIG. 30 for protocol description). The magnetic probe was placed 4.5" inches away from the center of the magnet placed first 5" up from the test surface and then 7" up from the test surface. The significance of this is, these heights coincide with the bottom and top of the top aluminum cylinder that surround magnet within the test apparatus device. Data was then gathered and analyzed for each protocol. When looking at the Power Spectrum that the test apparatus device produced, there was a clear difference. There was a greater total power present in the signal produce at 7", the top of the aluminum cylinder and further from the magnet, than at 5" at the bottom of the aluminum cylinder and closer from the magnet. This phenomenon led us to entertain the possibility that this shift in magnetic field is due to an eddying effect that occurs within each aluminum cylinder that surrounds the magnet. The results of this analysis can be seen displayed in FIG. 33 and FIG. 34.

Figure 35:
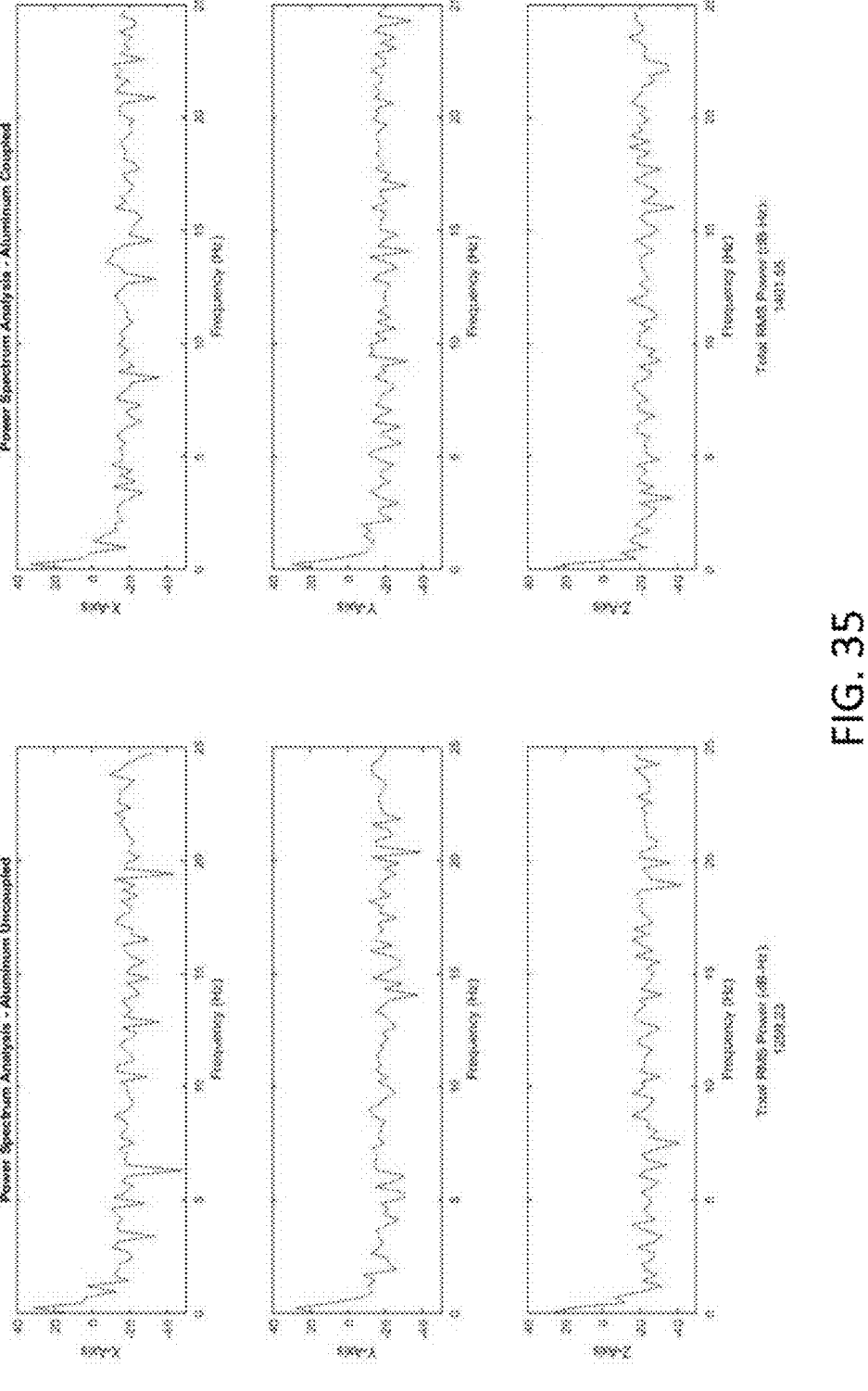
FIG. 35 depicts graphs of the Fast Fourier Transform analysis of the experimental magnetic field results for a test protocol with the device electrically coupled compared to not.
Figure 36:
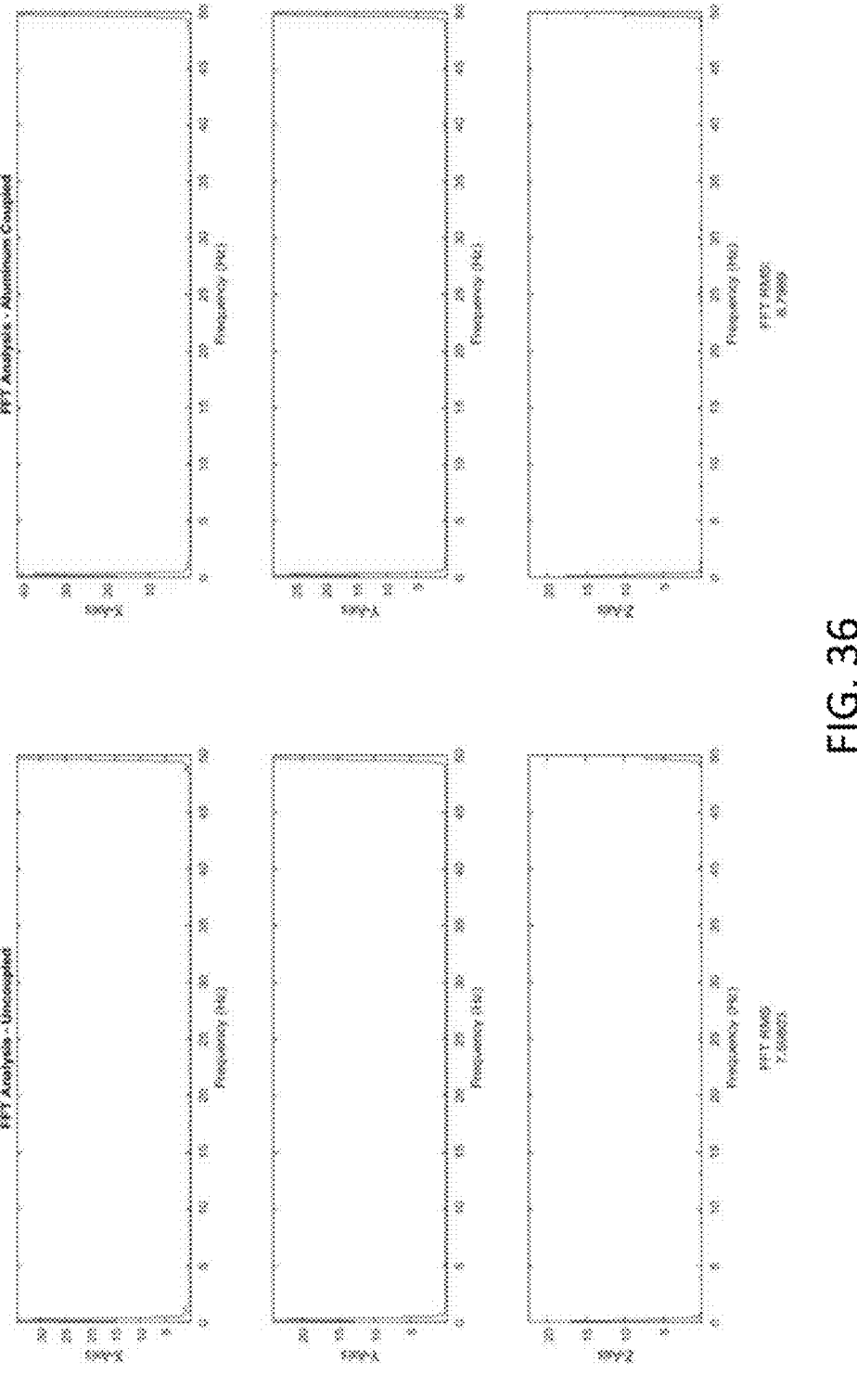
FIG. 36 depicts graphs of the Fast Fourier Transform analysis for a test protocol with the device electrically coupled compared to not from FIG. 35.

Electrical Coupling of Aluminum within the Test Apparatus Device. After seeing the Eddying effect occur in the aluminum surrounding the magnet, it was deemed necessary to further investigate this effect. Within the test apparatus device there are two aluminum cylinders that surround the magnet on either side. Based off previous findings, it was thought that eddying effects could possibly be occurring within each aluminum cylinder. Thus, it was thought if the cylinders were to be electrically coupled it would allow for a greater flow of electrons through the cylinders resulting in an increase in the overall power present in the signal. For this a wire was connected from the top on the bottom cylinder to the top of the top cylinder. The magnetic probe was placed 4.5" away from the center of the magnet and 7" up from the test surface, where the largest signal was produced. The test protocol 1 was the same protocol used in the previous test was used for this test (refer to FIG. 30 for protocol description). Data was then gathered and analyzed, and the test was then repeated for the device when the wire was removed. When looking at the data in the time domain there was no significant different between the magnitudes of the signal produced. However, when looking at the Power Spectrum that the test apparatus device produced, there was a clear difference. There was a greater total power present in the signal produce at 7", the top of the aluminum when it was electrically coupled top of one aluminum cylinder to the top of the other. This event further supported the possibility that eddying effects were occurring within the device. The results of this analysis can be seen displayed in FIG. 35 and FIG. 36.

Figure 37:
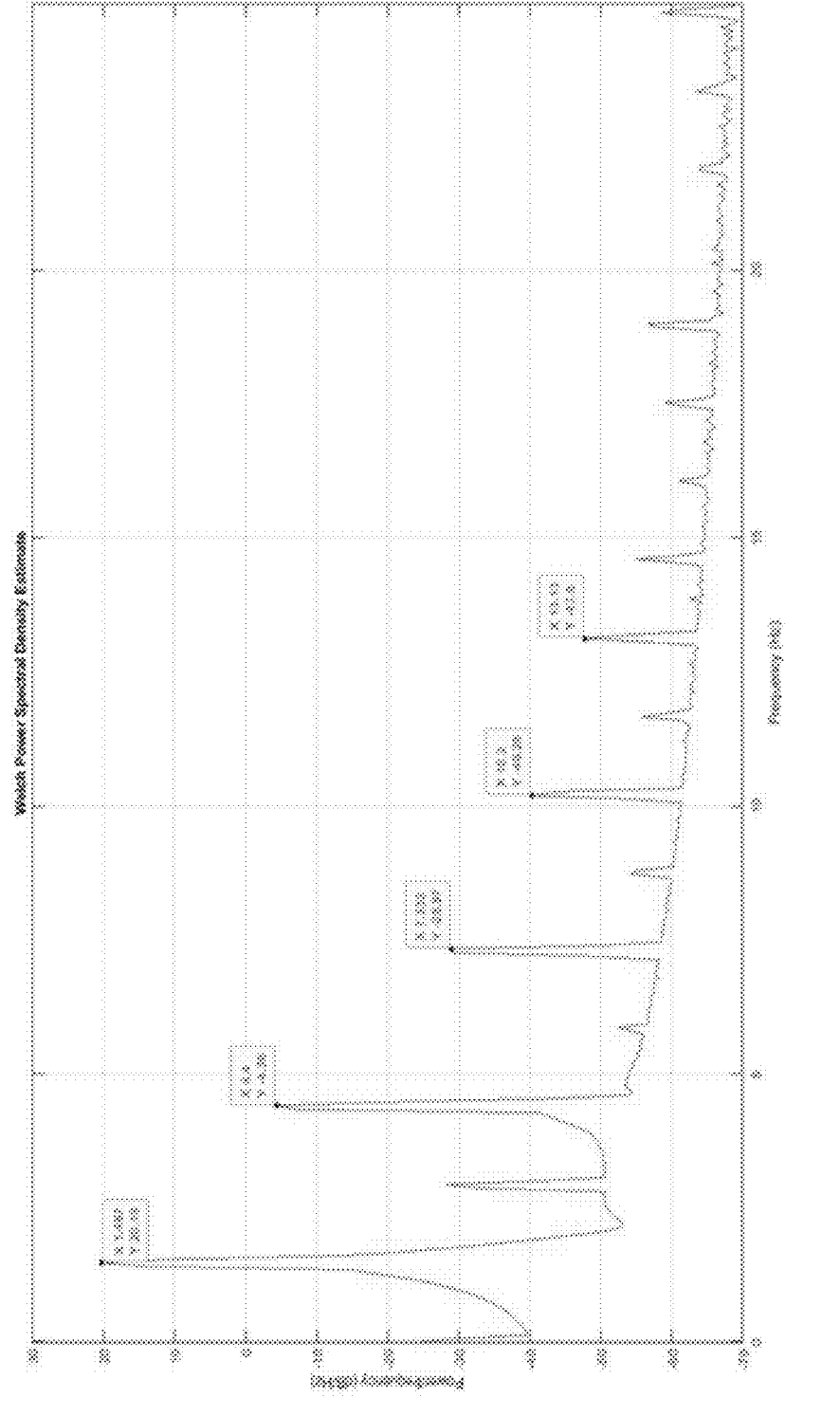
FIG. 37 depicts a graph showing the harmonics of the experimental data using the Welch Power Spectral Density analysis.

Harmonics Produced by Test Apparatus Device. Over the course of testing the magnetic pulse output and field testing, and looking at the power produced by each signal, it was decided that it would be beneficial to look at the frequencies that are produced by the device as well. To do so, test protocol 4 was analyzed (refer to FIG. 30 for protocol description). The magnetic probe was placed 4.5" inches away from the center of the magnet and positioned 7" up from the test surface. Data was then gathered and analyzed. A Welch Power Spectral Density Estimate was then performed on the data. This resulted in a power spectrum that filtered out the noise that was present in the data. After applying windows to reduce the noise it was clearly that the harmonic order frequencies were present in the signal and they were present at a lower harmonic level of the frequency at which the magnet rotates. The result of this analysis can be seen in FIG. 37.

Figure 38:
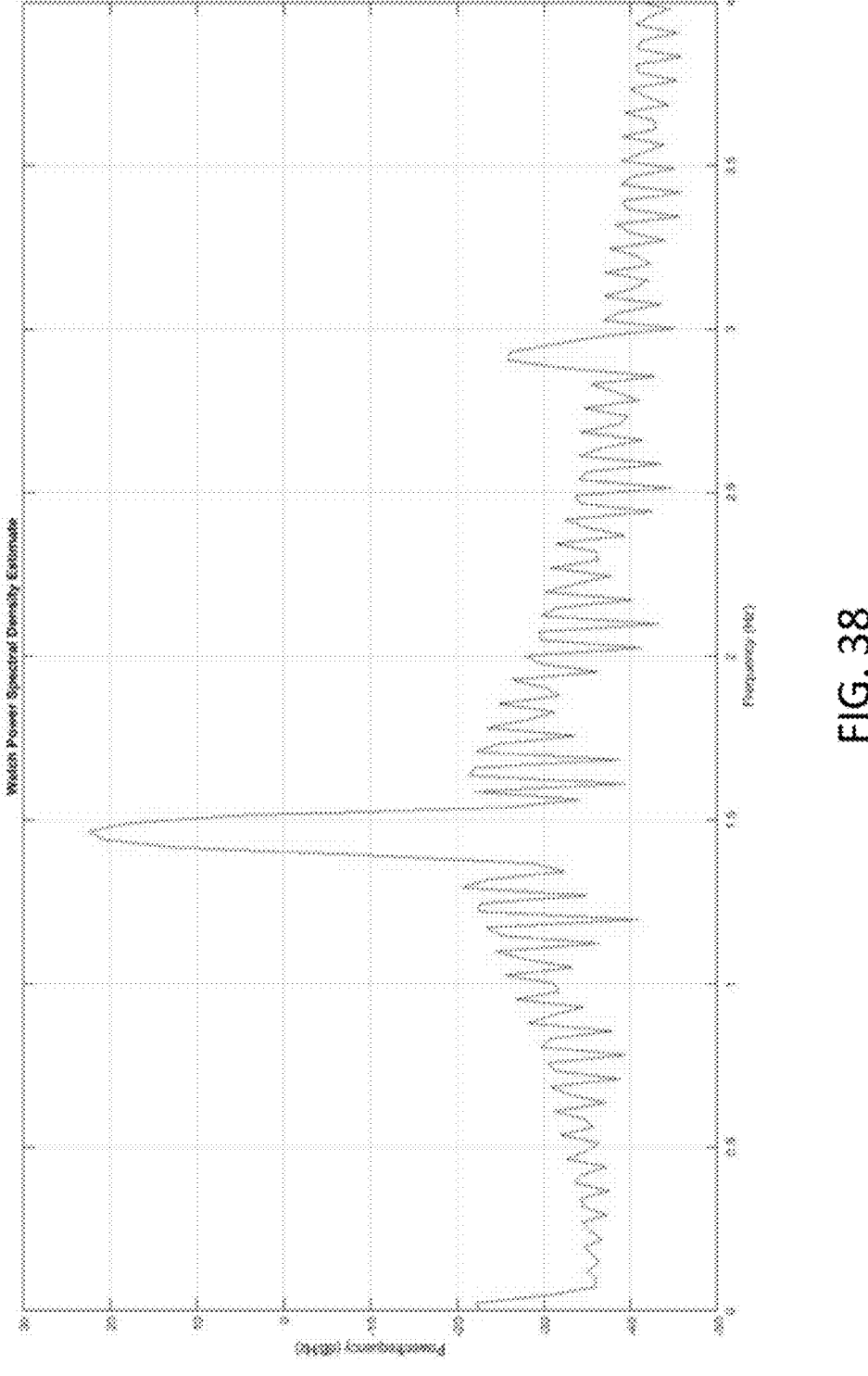
FIG. 38 depicts a graph of a power analysis of the experimental data using the Welch Power Spectral Density analysis.

Side Lobe Attenuation. While carrying out the analysis of the frequencies with the welch power spectral density analysis, it was found that accompanying each signal are side lobes. Using the same data that was recorded for the analysis of the harmonics produced by the test apparatus device, omitting the application of windows and filters it was clear that associated with each signal are side lobes or out of band attenuation. An example of this can be seen in FIG. 38. Of note, this energy repeats every 4 seconds, and looks like a pulse density modulation of 25 hz repeating every 4 seconds or 0.25 hz.

Figure 39:
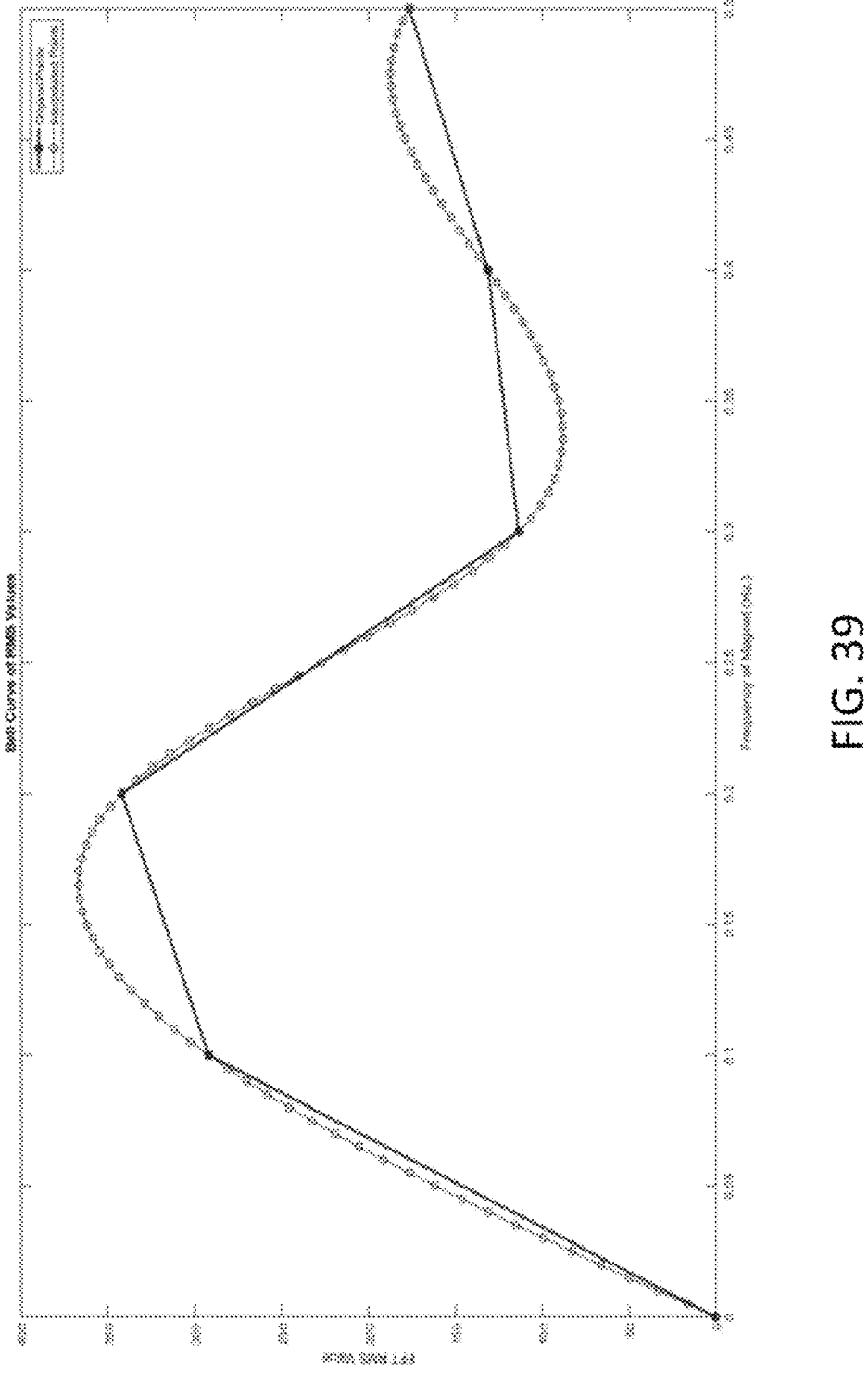
FIG. 39 depicts a graph of the comparison of RMS power value produced by the present invention when operating the magnet within the device at varying frequencies.

Changes in Magnetic Field due to frequency. With analyzing the power present in individual signals, it was also thought to compare the power of different signals. For this the magnetic probe was placed 4.5" inches away from the center of the magnet and positioned 7" up from the test surface. The test apparatus device was set to run at the frequencies of 0.1 Hz to 0.5 Hz incrementing by 0.1 Hz every time. These protocols are test protocols 5-9 (refer to FIG. 30) for a description for each of these protocols, data was then gathered and analyzed for each protocol. FFT RMS analysis was then performed on the data. This resulting spread of data can be seen in FIG. 39. From the data collected, the largest signal was present when the test apparatus device was running at slightly higher that 0.2 Hz.

Coupling with Human Subject. The final test that was carried out as an investigation into what the addition of a human subject would do in the to an isolated system test to determine any changes when the subject was proximate to the test apparatus. For this a wooden chair was added to the setup and placed in front of the test apparatus center on the side of the test apparatus device that is closest to the magnet that is within the device. The front of the chair was positioned even with the edge of the test apparatus device. The magnetic probe was placed on top of the eclipse device centered at the center of the magnet and positioned 1 inch above the top cover of the device. Test protocol 1 was used to test (refer to FIG. 30 for protocol description). The device was run for three two-minute trials with no human subject present to document a baseline energy and then repeated the test again with a human subject present.

Figure 40:
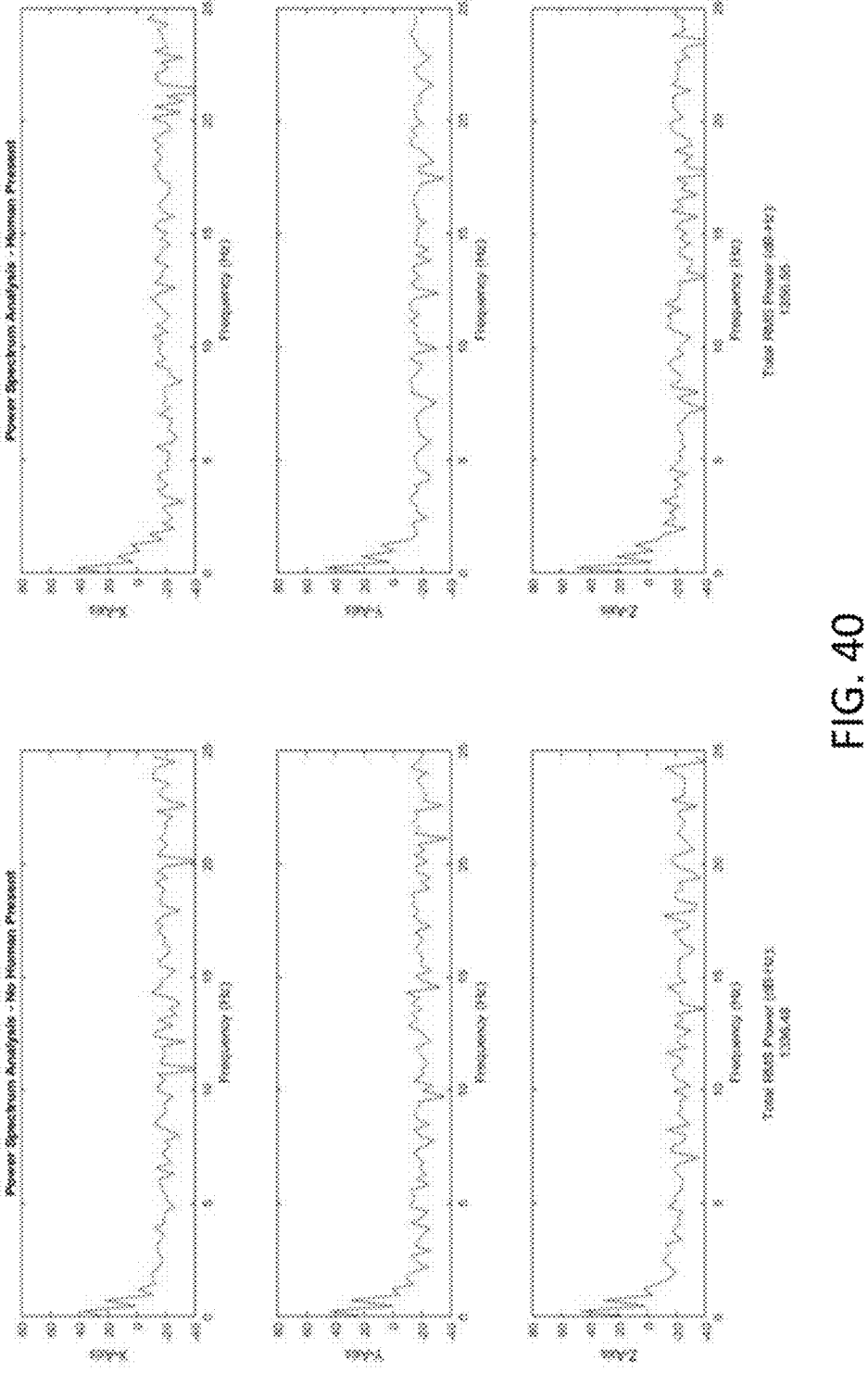
FIG. 40 depicts graphs of the power spectrum analysis of the experimental magnetic field results for a test protocol with the device operating in the presence of a human subject compared to not.
Figure 41:
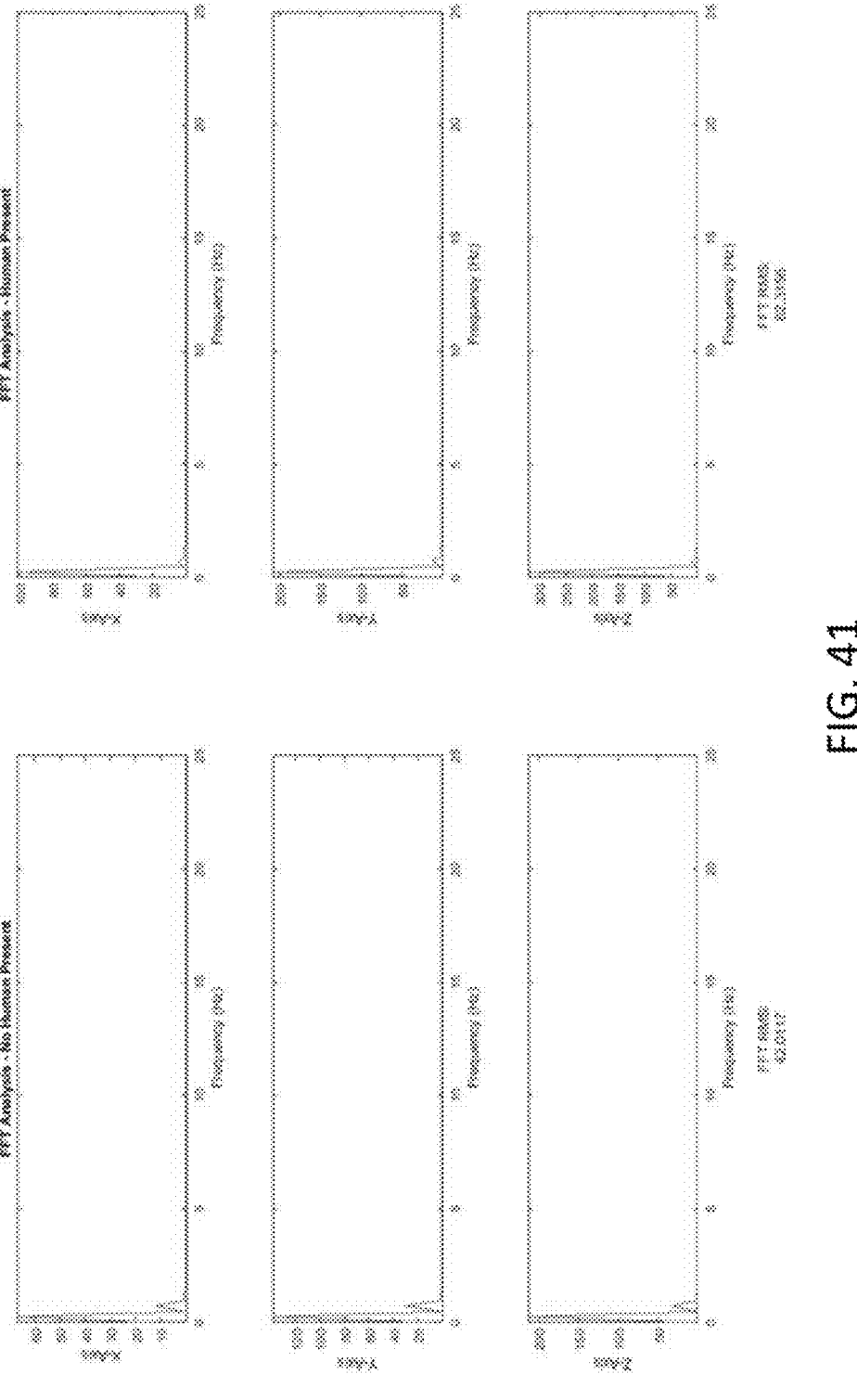
FIG. 41 depicts graphs of the Fast Fourier Transform analysis for a test protocol with the device operating in the presence of a human subject compared to not from FIG. 40.

The human subject placed his feet on either side of the device. For both scenarios the aluminum cylinders within the device were electrically coupled; data was then gathered and analyzed for each protocol. When looking at the data in the time domain there was no significant different between the magnitudes of the signal produced. However, when analyzed in the Power Spectrum the test apparatus device produced in each case; there was a clear difference. The total power observed was higher by approximately 50% when there was a human present. Also, when looking at the power of the signal when the human was present, we recorded the largest RMS power in in the entirety of our testing. The results of this analysis can be seen displayed in FIGS. 40, 41 and 42.

In summary, each of these tests were repeated the tests several times for confidence. Each time similar results were yield. Below is a summary list of the findings of this test apparatus device's characteristics as well as capabilities:

The test apparatus device creates sinusoidal and oscillating waveforms

When comparing the RMS power when the disks within the Eclipse device were spinning and not spinning, the largest power was seen when the disks were spinning.

When comparing the RMS power at different heights on the test apparatus device, the largest signal is found at the top of the device, which coincides with the top of the aluminum cylinder that is within the eclipse device.

When electrically coupling the two aluminum cylinders that sit within the test apparatus device and analyzing the RMS power present in that signal, a larger value was found versus when the aluminum was not coupled.

The test apparatus device produces a primary signal at the frequency at which the magnet rotates as well as secondary signals at frequencies that are at lower harmonics of the frequency of the magnet. Also, each of these signals have side lobes associated with the signals that they produce.

When comparing the RMS power at different frequencies the largest power was seen when the magnet rotated at a speed of 0.2 Hz.

When operating the test apparatus device in the presence of a human subject the RMS power found in the signal was larger than when no human subject was present.

Einstein's theory plays an important role in the modem theory of classical electromagnetism. First of all, it gives formulas for how electromagnetic objects, in particular the electric and magnetic fields, are altered under a Lorentz transformation from one inertial frame of reference to another. Secondly, it sheds light on the relationship between electricity and magnetism, showing that frame of reference determines if an observation follows electrostatic or magnetic laws. Moreover, it motivates a compact and convenient notation for the laws of electromagnetism, namely the "manifestly covariant" tensor form.

Maxwell's equations, when they were first stated in their complete form in 1865, would turn out to be compatible with special relativity. Moreover, the apparent coincidences in which the same effect was observed due to different physical phenomena by two different observers would be shown to be not coincidental in the least by special relativity. In fact, half of Einstein's 1905 first paper on special relativity, "On the Electrodynamics of Moving Bodies," explains how to transform Maxwell's equations.

The Joules-Bernoulli equation, considers two inertial frames. One of the fields is zero in one frame of reference, that doesn't necessarily mean it is zero in all other frames of reference. This can be seen by, for instance, making the unprimed electric field zero in the transformation to the primed electric field. In this case, depending on the orientation of the magnetic field, the primed system could see an electric field, even though there is none in the unprimed system. This does not mean two completely different sets of events are seen in the two frames, but that the same sequence of events is described in two different ways.

Figure 43:
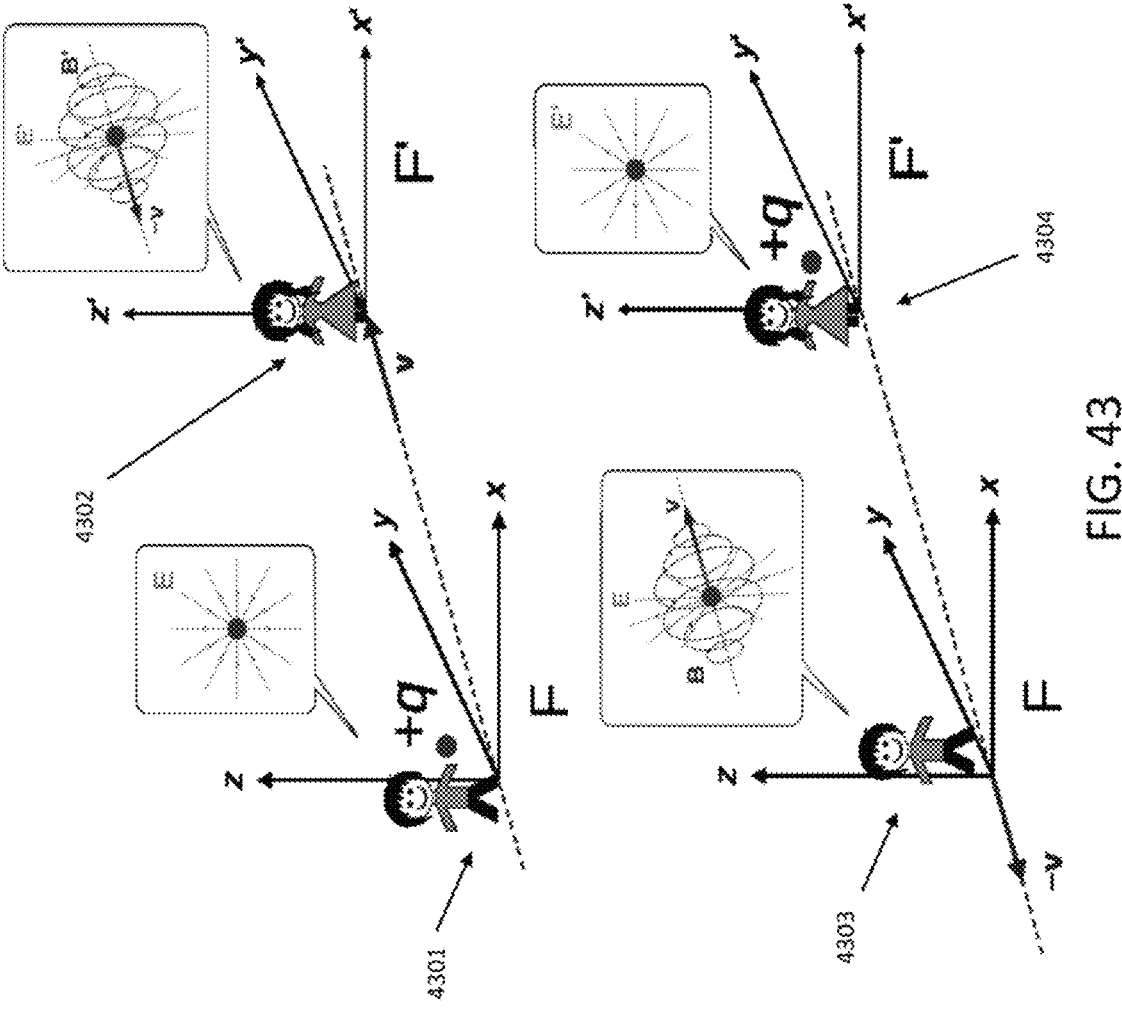
FIG. 43 depicts an illustration of a person sitting near the present invention receiving magnetic stimulation. This illustration also shows a line representing the human body nervous system.
Figure 43:

FIG. 43 depicts the Lorentz boost of an electric charge. The charge is at rest in frame F 4301, this observer sees a static electric field. An observer in another frame F' 4302 moves with velocity v relative to 4301, and sees the charge move with velocity −v with an altered electric field E due to length contraction and a magnetic field B due to the motion of the charge. The similar setup on the bottom of FIG. 43 shows 4303 in motion and the charge at rest in frame F' 4304.

The field components parallel to the velocity v are denoted by $E_{\parallel}$ and $B_{\parallel}$ while the field components perpendicular to v are denoted as $E_{\perp}$ and $B_{\perp}$. In these two frames moving at relative velocity v, the E-fields and B-fields are related by:

$$E_{\parallel}'=E_{\parallel} \tag{111}$$

$$B_{\parallel}'=B_{\parallel} \tag{112}$$

$$E_{\perp}'=\gamma(E_{\perp}+v\times B) \tag{113}$$

$$B_{\perp}'=\gamma(B_{\perp}+v\times E) \tag{114}$$

The Lorentz factor or Lorentz term $\gamma$ is the factor by which time, length, and relativistic mass change for an object while that object is moving. The expression appears in several equations in special relativity, and it arises in derivations of the Lorentz transformations. The name originates from its earlier appearance in Lorentzian electrodynamics.

$$\gamma = \frac{1}{\sqrt{1 - \frac{v^2}{c^2}}} \tag{115}$$

The RMS of a time history is a measure of the signal's overall energy and is often used when extracting features from a signal for prognosis and trending of vibration data. One important feature of using FFT, as defined by Parseval's theorem, is that total energy of the signal is preserved. Parseval's theorem states that the sum (or integral) of the square of a function is equal to the sum (or integral) of the square of its Fourier transform.

This is an aspect of Parseval's Theorem. Parseval's Theorem says the sum of squares in the time domain is equal to the sum of squares in the frequency domain. In the analog domain the sum of this is the area under the curve or the integral. In other words, total energy in the time domain equals total energy in the frequency domain. Equation [128] for $g_{RMS}$ represents the time domain energy and the integral represents the energy in the frequency domain. A similar result holds for power. The area under the power spectral density curve is equal to the total signal power.

$$g_{RMS}=\sqrt{\int_{f_1}^{f_2}PSD(f)df} \tag{116}$$

When the RMS of the power spectral density signal is squared, the overall power present in that signal is calculated. From this it can be stated that the RMS value of signals from the test data increase and that is an increase in the signal power.

The interpretation of this form of the theorem is that the total energy of a signal can be calculated by summing power-per-sample across time or spectral power across frequency. Thus, the sum the spectral power over the frequency of the sample calculates the power.

Taking the power found from the average signal and the frequency of the signal (the signal repeats approx. every 4 seconds) the total energy of a single signal is calculated.

$$Power = \frac{Work}{Time} \tag{117}$$

$$Work = Kinetic\ Energy \tag{118}$$

$$Frequency = \frac{1}{Time} \tag{119}$$

-continued $$\text{Power} = \text{Kinetic Energy} * \text{Frequency (Signal)} \qquad [120]$$

$$\therefore \text{Kinetic Energy} = \frac{\text{Power}}{\text{Frequency}} \qquad [121]$$

All functions in the human body are controlled by electrical signals. Each one of these electrical signals transfer information through the nervous system, brain, spinal cord, muscles, and organs. The human body sends billions of electrical signals a day.

A neuron is the basis structural unit of the nervous system. It allows the transmission and reception of electrical pulses for information transfer. A single neuron is a complex nerve fiber. It is built up of axons, nucleus, dendrites, and synapses. Many if not most neurons have a myelin sheath. The nucleus is the core which contains DNA information to control the operation of the cell. Dendrites receiver antenna of neurons. Synapses are contact points to other neurons and axons are the long fibers which allows the transmission of electrical signals.

The nervous system acts like electrical wires throughout the body. It is known in the art that these electrical signals can be mathematically modeled. In the case of the device, the magnetic field is believed to stimulate the electrical signals in the body. It is known in the art that a magnetic field will affect any current carrying wire.

The axon material has an electrical resistance, which is approximately $\rho \approx 1.1$ $\Omega$m. Knowing the radius of an axon which is approximately 5 micrometers and assuming the length is 1 meter long, the electrical resistance can be calculated.

The cross-sectional area of an axon is modeled as a circle.

$$A = \pi r^2 \qquad [122]$$

$$A = \pi (5*10^{-6} \text{ m})^2 = 7.85*10^{-11} \text{ m}^2 \qquad [123]$$

Now that the cross-sectional area is known, the resistance is calculated.

$$R = \frac{\rho l}{A} \qquad [124]$$

$$R = \frac{1.1\Omega m * 1m}{7.85*10^{-11} m^2} = 1.4*10^{10} \Omega \qquad [125]$$

The rotating magnet in the device can induce a current in a conducting wire. In this case the wire is the nervous system. The magnetic flux is depended on the number of wires N. The central nervous system has 43 strands that run throughout the body. In this model they are all assumed to be 1 meter long. This is shown in FIG. 44. FIG. 44 depicts a person 4401 sitting near the device 500 with the magnetic field of the device influencing the electrons in the nervous system 4402. The magnetic flux from the device is also dependent on the strength of the magnetic field B, the perpendicular area of the nerve to the magnetic field A and the cosine of the angle θ between the cross-sectional area to the magnetic field vector. The angle is also the angular velocity multiplied by time wt.

$$\Phi = NBA \cos(\theta) = NBA \cos(\omega t) \qquad [126]$$

An emf will be produced in the wires or nerves equal to the rate of change in magnetic flux. This is the time derivative of the magnetic flux.

$$emf = \frac{d\Phi}{dt} = NBA\omega \sin(\omega t) \qquad [127]$$

The frequency of the magnet is 0.25 Hz which is used to calculate angular velocity.

$$\omega = 2\pi f \qquad [128]$$

$$\omega = 2\pi (0.25 \text{ Hz}) = 1.57 \frac{rad}{s} \qquad [129]$$

Looking at the change in magnetic flux over a time of 1 second, the emf is calculated.

$$emf = 43(1.4T)(7.85*10^{-11} m^2)\left(1.57\frac{rad}{s}\right)\sin(1.57) \qquad [130]$$

$$emf = 7.42 \text{ } \mu V \qquad [131]$$

Now that the emf is calculated. The current and power can be calculated.

$$I = \frac{emf}{R} \qquad [132]$$

$$I = \frac{7.42 \text{ } \mu V}{14 \text{ } G\Omega} = 5.3*10^{-19} \text{ A} \qquad [133]$$

$$P = emf * I \qquad [134]$$

$$P = 3.94*10^{-27} \text{ W} \qquad [135]$$

From the power spectrum density data collected, power is in units of decibels per hertz $$\frac{db}{hz}.$$

This is power in watts on a logarithmic scale. The conversion is shown in equation [136].

$$P(dbW) = 10 \log_{10} P(W) \qquad [136]$$

$$P = -264 \text{ db} \qquad [137]$$

From the data collected with a subject and without, there was a jump in energy at 10.2 Hz. It is believed at that frequency the data shows the energy of the subject. 10.2 Hz is used to convert power from decibels to decibels per hertz.

$$P = \frac{-264 \text{ db}}{10.2 \text{ Hz}} = -25.9 \frac{db}{Hz} \qquad [138]$$

This is just the power shown a 1 second into the magnet's rotation. To consider 1 full rotation of the magnet, the summation of all the power over the total time of 4 seconds must be calculated. The plots of the emf, current, power in watts, and power in decibel-hertz is generated using Matlab shown in FIG. 45.

Figure 45:
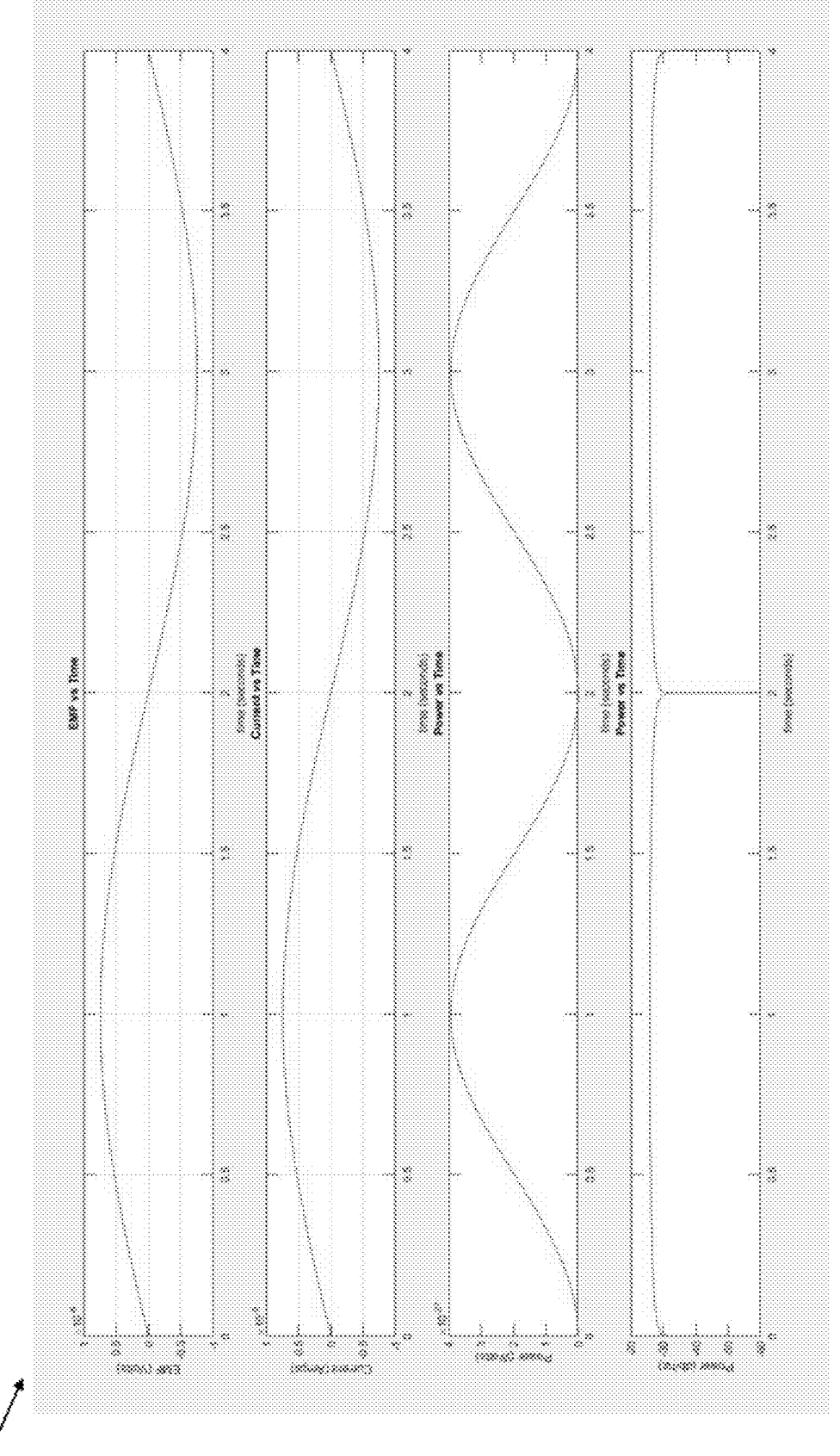
FIG. 45 depicts a graph showing how physics is linear up until the point to which it is not.

Looking at FIG. 45, when the magnet rotates, the flipping north and south poles creates an alternating emf as well as an alternating current. When the power is calculated results in a positive sinusoidal magnitude. The total power for the power graph is the area under the curve over the 4 second period. An integral can be computed over the 4 second period resulting in a power of $$P = -21.3 \frac{\text{db}}{\text{Hz}}.$$

This was integrated using Matlab's built in trapz numerical integration function.

To derive Einstein's energy equation, we must first look and the change in energy defined as the change in work which is a force multiplied by the distance of the force.

$$dE = F dx \qquad [139]$$

Force can be expressed in the change of momentum over the change in time.

$$dE = \frac{dp}{dt} dx \qquad [140]$$

Momentum p is equal to the mass multiplied by velocity.

$$p = mv \qquad [141]$$

The time differential of momentum can be expressed as the mass multiplied by the time derivative of velocity plus the velocity multiplied by the time derivative of mass.

$$\frac{dp}{dt} = \frac{d}{dt}(mv) = m\frac{dv}{dt} + v\frac{dm}{dt} \qquad [142]$$

The equation can be rearranged to equate the change in distance over the change in time to velocity.

$$dE = m\frac{dv}{dt} dx + v\frac{dm}{dt} dx \qquad [143]$$

$$dE = m\frac{dx}{dt} dv + v\frac{dx}{dt} dm \qquad [144]$$

$$v = \frac{dx}{dt} \qquad [145]$$

$$dE = mv\,dv + v^2 dm \qquad [146]$$

Relativistic mass describes how as a mass approaches the speed of light will increase in mass. Where $m_0$ is the mass at rest or invariant mass, v is the velocity, and c is the speed of light. This is also a concept of the Lorentz factor from equation [138].

$$m = \frac{m_o}{\sqrt{1 - \frac{v^2}{c^2}}} \qquad [147]$$

Taking the derivative with mass with respect to velocity the equation can be rearranged.

$$\frac{dm}{dv} = m_o * -\frac{1}{2}\left(1 - \frac{v^2}{c^2}\right)^{-\frac{3}{2}} * -\frac{2v}{c^2} \qquad [148]$$

-continued $$\frac{dm}{dv} = \frac{m_o v}{c^2}\left(1 - \frac{v^2}{c^2}\right)^{-\frac{3}{2}} \qquad [149]$$

$$\frac{dm}{dv} = \frac{m_o v}{c^2}\left(1 - \frac{v^2}{c^2}\right)^{-\frac{1}{2}}\left(1 - \frac{v^2}{c^2}\right)^{-1} \qquad [150]$$

$$\frac{dm}{dv} = \frac{mv}{c^2}\left(1 - \frac{v^2}{c^2}\right)^{-1} \qquad [151]$$

$$\frac{dm}{dv} = \frac{mv}{c^2}\left(\frac{c^2 - v^2}{c^2}\right)^{-1} \qquad [152]$$

$$\frac{dm}{dv} = \frac{mv}{c^2}\left(\frac{c^2}{c^2 - v^2}\right) \qquad [153]$$

$$\frac{dm}{dv} = \frac{mv}{c^2 - v^2} \qquad [154]$$

$$c^2 dm = (mv)dv + v^2 dm \qquad [155]$$

This equation can be substituted into the energy equation.

$$dE = c^2 dm \qquad [156]$$

To calculate the total energy, take the integral of both sides.

$$\int_{E_i}^{E_f} dE = \int_{m_i}^{m_f} c^2 dm \qquad [157]$$

The integral equals the change in energy equals the change in mass multiplied the speed of light squared.

$$E_f - E_i = (m_f - m_i)c^2 \qquad [158]$$

$$\therefore E = mc^2 \qquad [159]$$

In inertial reference frames other than the rest frame or center of mass frame, the equation [159] remains true if the energy is the relativistic energy and the mass is the relativistic mass. It is also correct if the energy is the rest or invariant energy (also the minimum energy), and the mass is the rest mass, or the invariant mass. However, connection of the total or relativistic energy with the rest or invariant mass requires consideration of the system's total momentum, in systems and reference frames where the total momentum (of magnitude p) has a non-zero value. The formula then required to connect the two different kinds of mass and energy, is the extended version of Einstein's equation, called the relativistic energy-momentum relation. To be able to describe a system with momentum the equation must be squared and manipulated.

$$E^2 = (mc^2)^2 \qquad [160]$$

Substituting equation [147] in for mass.

$$E^2 = \frac{m_o^2 c^4}{1 - \frac{v^2}{c^2}} \qquad [161]$$

Rearranging the terms to get energy in terms of momentum, mass, and the speed of light.

$$E^2 = \frac{m_o^2 c^4}{1 - \frac{p^2 c^2}{m_o^2 c^2 + p^2}} \qquad [162]$$

-continued $$E^2 = \frac{m_o^2 c^4 (m_o^2 c^2 + p^2)}{(m_o^2 c^2 + p^2) - p^2}$$ [163]

$$\therefore E^2 = m_o^2 c^4 + p^2 c^2$$ [164]

This form of the equation takes into consideration systems of mass and momentum.

The mass of an electron in kilograms is $9.109*10^{-31}$ kg. Plugging this into the energy equation [164] assuming the electron is at rest:

$$E = \sqrt{\left[(9.109*10^{-31}\,[kg])^2 \left(2.99*10^8 \left[\frac{m}{s}\right]\right)^4\right] + \left[0\left[\frac{kg*m}{s}\right]^2 \left(2.99*10^8 \left[\frac{m}{s}\right]\right)^2\right]}$$ [165]

The answer comes out to be $E=8.14*10^{-14}$J which is the electrons rest energy. This is how mass is related to energy.

With respect now to the laws of physics, one of the assumptions most scientists have about the universe is there are absolute physical laws that describe or govern the behavior of the universe, we typically call them the laws of physics; then there are the scientific theories developed over centuries of experiment and observation let's call these the observed laws of physics. The reality, the two aren't necessarily the same, which is why some new discoveries are said to "break the laws of physics", when in actuality they may fall into the category of newly observed laws of physics. In the spirit of the foregoing discussion regarding these laws and observations, certain theories or special theories we present, we conclude so with an open mind regarding the art of the possible.

Let's start with an understanding of the laws of the conservation of energy; it states that total energy of an isolated system remains constant and is conserved over time. This law means that energy can neither be created nor destroyed; rather, it can only be transformed or transferred from one form to another such that if one adds up all forms of energy in the isolated system, you would have the total energy of that system and that it remains constant. These energies would include the kinetic and potential energies of all the isolated system elements.

Next is understanding the definition of the word mass, it generally has two meanings from two frames of reference with respect to an observer:

the first in special relativity where rest mass or invariant mass is an invariant quantity which is the same for all observers in all reference frames, The second is relativistic mass which is dependent on the velocity of the observer.

According to the concept of mass-energy equivalence, the rest mass and relativistic mass are equivalent to the rest energy and total energy of the body, respectively. The term relativistic mass tends not to be used in particle and nuclear physics and is often avoided by writers on special relativity, in favor of using the body's total energy as propose by Einstein. In contrast, rest mass is usually preferred over rest energy because the measurable inertia and gravitational attraction of a body in a given frame of reference is determined by its relativistic mass, not merely its rest mass; a good example, light has zero rest mass but contributes to the inertia and weight in a gravitational field of any system containing it. So, if massless particles like a photon has inertia and can contribute to weight in a gravitational field, why can't we consider this in our simplified models?

As stated above, relativistic mass tends not to be used in particle physics and is often avoided by writers; but what if it was used? What if we were to simplify the system to just one set of rules; a single set of definitions; and a single set of assumptions. One where the mass of particles at rest do have energy as a function of mass, acceleration, time, and momentum? A system where the mass-energy equivalence is always a function of the system's total energy including momentum; and is the same in all frames of reference. This means that particles at rest in an expanding universe are moving and have a momentum, that momentum can be related to a second energy $E_k$, a kinetic energy that has a non-zero value.

Figures 46A, 46B:
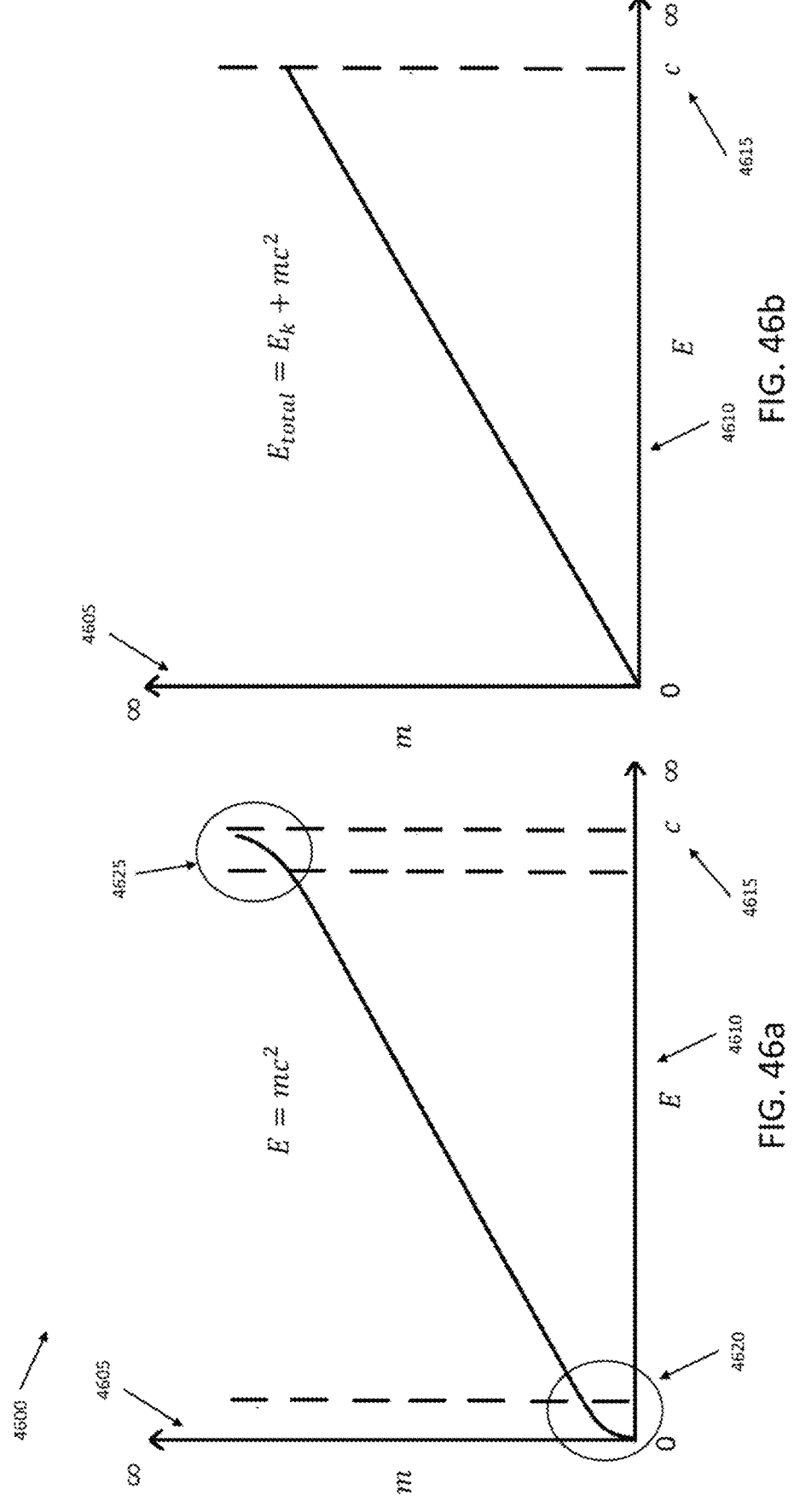
FIGS. 46*a* and 46*b* depict the power time domain relationship of a sine wave.

We start with how we arrive at our assumptions, FIGS. 46a and 46b depict 2 simple line drawings representing the relationship of energy and mass at the ratio of $c^2$; these graphics are not scaled proportionally, and was only done only to assist the reader in understanding the inventors approach in understanding and teaching certain aspects of the embodiment of the invention. Both FIG. 46a and FIG. 46b represents the mass-energy equivalence which for all intents and purposes is a linear function, by linear we mean that inputs scale to the outputs as a function of the ratio $c^2$. On either end of the mass energy graph at 4620 and 4625 there is an area where there is a possibility some aspects of the physics have some non-linearity aspect, where the rules need assumptions adjusted resulting in new theories, like the String Theory.

On both graphs mass is on the vertical axis 4605, starts at 0 and ends at infinity ($\infty$); the horizontal 4610 axis represents energy, it starts at zero and ends at infinity. The point 4615 marked as c represents the speed of light, the areas represented by 4625 represent a possibility of non-linearities in the theories as the mass of particle approaching the speed of light approaches $\infty$. At the lower end the mass at 4620 approaches 0. At 0, the particle is a massless particle, these are considered elementary particles. An example of the massless particle is the photon, the carrier of electromagnetism; it is massless but oddly enough it has inertia and a relationship to gravity as an attractive force:

$$F_g = G\frac{m_1 m_2}{r^2}$$ [166]

$$G = 6.67 \times 10^{-11} \frac{m^3}{kg*s^2}$$ [167]

Where G is the universal gravitational constant. The point is we are working in the realm of classical physics greater than 0 and less than infinity and assume everything is measurable, so for our isolated system of mass-energy we say that mass and energy have one of 3 values:

$m=0;0<m<\infty;m=\infty;$ [168]

$E=0;0<E<\infty;E=\infty;$ [169]

Since there is a relationship between mass and Gravity, then one could say that Gravity exists as a value as:

$G=0;0<G<\infty;G=\infty;$ [170]

The following discussion goes into a detailed discussion of measured energy in an isolated system, where the total energy of the system is energy transferred not energy transformed. In the first case the isolated system comprises the apparatus of the invention, connected to an external energy source, the energy transferred is through the connection and was measured at 0.5 amps at 24 volts; these tests yielded a total energy of the isolated system as $E_1=E_{Apparatus}$ in Joules. In the second case, a human subject was placed into the isolated system along with the test apparatus, the expectation was that energy would be transferred into the test subject during the magnetic stimulation test and the measured energy was expected to result in a total energy of the isolated system as $E_2=E_{Apparatus}-E_{Transferred}$ in Joules as a function of energy transferred into the subject; this was consistent with earlier tests conducted with an electrolyte fluid where absorbed energy resulted in a lower total isolated system energy.

However, when the subject was introduced into the isolated system, where there was a measured change in the isolated system total energy such that $E_2=E_{Apparatus}+E_{Transferred}$; where the energy transferred into the system apparatus remained constant. The total energy with the apparatus and the subject measured can be represented as $E_2=1.5E_1$; an increase in total energy of the isolated system of approximately 50%. The laws of the conservation of energy tells us that energy can only be transformed or transferred from one form to another, therefore it can only mean the human subject was now part of the isolated system, and that energy was transferred from the subject into the system; the energy measured was not as a result of energy gain from the transformation of mass during the conduct of the test. The question is what energy was transferred into the isolated system that was measured and documented, where did it come from.

As stated above, when a human comes into the system. There is a noticeable jump in energy from the measured data. A human is its own system of energy from all the chemical reactions happening in the human body. Energy signals in the human body rely on the movement of electrons. It is believed that the changing magnetic flux stimulates the nervous system similar to an electrical wire. As it is known in the art of physics, a changing magnetic flux will induce a current in a wire by the movement of electrons. That force moving the electrons is the Lorentz force produced by the changing magnetic field.

In the laws of the conservation of energy, energy is neither created nor destroyed. There is only energy transferred or energy transformed. For this system, adding a human body into the isolated system with the device is an addition of energy. The total energy is the sum of all the energies in the system.

$$E_{total}=E_{Transfered}+E_{Transformed} \qquad [171]$$

$$E_{total}=E_k+mc^2 \qquad [172]$$

With the earlier discussion regarding mass- and energy in a system where momentum carries down to particles like electrons, equation [172] shows the total energy of a system that has a kinetic energy component $E_k$. The kinetic energy component is equal to the momentum multiplied by the speed of light.

$$E_k=pc \qquad [173]$$

This component of energy could be released back into the isolated system during the input of energy from the test apparatus and is assumed to be energy from the human body. The human and device both operate at 0.25 Hz. We see a jump in energy at that frequency on a PSD plot.

As for other forms of energy, the average human consumes 2000 calories a day. One calorie is equal to 4184

Joules. Thus, per day the average human produces 8,368,000 joules of energy. This can be converted into watts for an energy value.

$$8,368,000\frac{Joules}{day}*\frac{1\ day}{24\ hours}*\frac{1\ hour}{60\ minutes}*\frac{1\ minute}{60\ seconds}=96.9\ Watts \qquad [174]$$

This energy generated is an element of the total energy that a human body uses. In the isolated system of the human body and the device it is possible this energy is a factor of the measured energy. In an alternate discussion of energy, all functions in the human body are controlled by electrical signals. Each one of these electrical signals transfer information through the nervous system, brain, spinal cord, muscles, and organs. The human body sends billions of electrical signals a day.

A neuron is the basis structural unit of the nervous system. It allows the transmission and reception of electrical pulses for information transfer. A single neuron is a complex nerve fiber. It is built up of axons, nucleus, dendrites, and synapses. The nucleus is the core which contains DNA information to control the operation of the cell. Dendrites receiver antenna of neurons. Synapses are contact points to other neurons and axons are the long fibers which allows the transmission of electrical signals.

The plasma membrane of neurons, like all other cells, has an unequal distribution of ions and electrical charges between the two sides of the membrane. The outside of the membrane has a positive charge, inside has a negative charge. This charge difference is a resting potential and is measured in millivolts. Passage of ions across the cell membrane passes the electrical charge along the cell. The voltage potential is −65 mV (millivolts) of a cell at rest (resting potential).

Resting potential results from differences between sodium and potassium positively charged ions and negatively charged ions in the cytoplasm. Sodium ions are more concentrated outside the membrane, while potassium ions are more concentrated inside the membrane. This imbalance is maintained by the active transport of ions to reset the membrane known as the sodium potassium pump. The sodium-potassium pump maintains this unequal concentration by actively transporting ions against their concentration gradients.

Since the nervous system has an electric potential and relies on the movement of electrons, this is another element of energy when considering the total energy of the system. The amount of energy of this element is difficult to calculate since it varies person to person and depends on the state of that person. Never the less it is known that the energy is present.

In electrical engineering, two conductors are said to be inductively coupled or magnetically coupled when they are configured such that a change in current through one wire induces a voltage across the ends of the other wire through electromagnetic induction. A changing current through the first wire creates a changing magnetic field around it by Ampere's circuital law. The changing magnetic field induces an electromotive force (EMF or voltage) in the second wire by Faraday's law of induction. The amount of inductive coupling between two conductors is measured by their mutual inductance.

It is believed that the human and the device are inductively coupled when the device is running. The nervous system relies on the movement of electrons. In the art of physics, it is known that the movement of electrons induce a magnetic field by Ampere's circuital law. The rotating magnet also assembly helps moves electrons in the human body through the Lorentz force. Both systems operate at the same frequency of 0.25 Hz which causes an additive magnetic field by vector mathematics, the Biot-Savart law, and an additive power level by superposition. If there is such a coupling then we have a transfer of energy. This potentially why there is a jump in energy with a human body in the system compared to the isolated system with just the device producing a magnetic field.

In a discussion with respect to Non-Transitory Computer Readable Medium: The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general-purpose processor may be a microprocessor, but in the alternative, the processor may be any commercially available processor, controller, microcontroller or state machine. A processor may also be implemented as a combination of two computing components, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Thus, in some aspects, a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Processes or steps described in one implementation can be suitably combined with steps of other described implementations.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device.

For the sake of convenience, the operations are described as various interconnected functional blocks or distinct software modules. This is not necessary, however, and there may be cases where these functional blocks or modules are equivalently aggregated into a single logic device, program or operation with unclear boundaries. In any event, the functional blocks and software modules or described features can be implemented by themselves, or in combination with other operations in either hardware or software.

Having described and illustrated the principles of the systems, methods, processes, and/or apparatuses disclosed herein as an embodiment thereof, it should be apparent that the systems, methods, processes, and/or apparatuses may be modified in arrangement and detail without departing from such principles. Claim is made to all modifications and variation coming within the spirit and scope of the following claims.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The embodiments of the invention in which an exclusive property or privilege is claimed are defined as follows:

1. An apparatus for producing a polarizing magnetic field stimulation comprising:

a magnet mounted within a tube, wherein the tube comprises at least one non-magnetic conductive metal alloy, wherein the tube is comprised of two or more segments and the two or more segments are electrically isolated from each other, and wherein the tube is mounted within a housing;

a first motor attached to the magnet such that when operated, rotates the magnet within the tube, wherein a rotation of the magnet is transverse to a north-south pole axis resulting in switching polarity of a magnetic field of the magnet;

a first processor mounted within the housing, configured to:

use a wireless communication protocol to connect a wearable second processor, to the first processor mounted within the housing, wherein the wearable second processor is located in a wearable device;

responsive to connecting the wearable second processor to the first processor mounted within the housing, select a preconfigured motor control protocol to operate the first motor, wherein the preconfigured motor control protocol causes the first motor to rotate the magnet to produce a polarizing magnetic field and controls at least one of motor phase, frequency, amplitude, and duration;

responsive to selecting the preconfigured motor control protocol, transmit the preconfigured motor control protocol from the wearable second processor to the first processor mounted within the housing;

responsive to transmitting the preconfigured motor control protocol, operate the first motor using the preconfigured motor control protocol, wherein operating the first motor generates the polarizing magnetic field by rotating the magnet, wherein the polarizing magnetic field results in a magnetic stimulation, wherein the magnetic stimulation comprises an element of phase, frequency, amplitude and power of a medical therapy.

2. The apparatus of claim 1, wherein the non-magnetic conductive metal alloy of the tube is used to produce eddy currents to modify the polarizing magnetic field.

3. The apparatus of claim 1, wherein the two or more segments of the tube are electrically coupled to the first processor and controlled by preconfigured motor control protocol, wherein each segment is individually coupled to the first processor, and wherein the segments are coupled and decoupled using electrical leads attached to each tube segment.

4. The apparatus of claim 1, wherein the wireless protocol is at least one of IEEE 802.11 WIFI; IEEE 802.15.4 LR-WPANS; ISO/IEC 18092; ISO/IEC 18092 NFC Personal Health Data Exchange Protocol AND ISO/IEEE 17073-20601.

5. The apparatus of claim 1, wherein the at least one preconfigured protocol controls at least one of the magnet's rotation frequency, and degrees the magnet rotates.

6. A method for producing a polarizing magnetic field stimulation comprising:

mounting a magnet within a tube of an apparatus, wherein the tube has at least one opening, and the tube comprises at least one non-magnetic conductive metal alloy, wherein the tube is comprised of two or more segments and the two or more segments are electrically isolated from each other, and wherein the tube is mounted within a housing;

attaching a first motor to the magnet such that when operated, rotates the magnet within the tube, wherein a rotation of the magnet is transverse to a north-south pole axis resulting in switching polarity of a magnetic field of the magnet;

mounting a first processor within the housing, configured to:

use a wireless communication protocol to connect a wearable second processor, to the first processor mounted within the housing, wherein the wearable second processor is located in a wearable device;

responsive to connecting the wearable second processor to the first processor mounted within the housing, select a preconfigured motor control protocol to operate the first motor, wherein the preconfigured motor control protocol causes the first motor to rotate the magnet to produce a polarizing magnetic field and controls at least one of motor phase, frequency, amplitude, and duration;

responsive to selecting the preconfigured motor control protocol, transmit the preconfigured motor control protocol from the wearable second processor to the first processor mounted within the housing;

responsive to transmitting the preconfigured motor control protocol, operate the first motor-using the preconfigured motor control protocol, wherein operating the motor generates the polarizing magnetic field by rotating the magnet, wherein the polarizing magnetic field results in a magnetic stimulation, wherein the magnetic stimulation comprises an element of phase, frequency, amplitude and power of a medical therapy.

7. The method of claim 6, wherein the magnetic field is received by at least one of neural components and perineural components of a human body.

8. The method of claim 6, wherein the polarizing magnetic field is generated by at least one of a static magnetic field and an electro-magnetic fields of the magnet.

9. The method of claim 6, wherein the preconfigured motor control protocol generates a pulse density of magnetic energy that corresponds to a frequency of rotation of the magnet, and wherein the pulse density-of magnetic energy is altered by addition of inductive energy from an electrical connection of the tubes.

10. The apparatus of claim 6, wherein the wireless protocol is at least one of IEEE 802.11 WIFI; IEEE 802.15.4 LR-WPANS; ISO/IEC 18092: ISO/IEC 18092 NFC Personal Health Data Exchange Protocol AND ISO/IEEE 17073-20601.

11. The method of claim 6 wherein the wearable second processor is coupled to a first sensor, wherein the coupled first sensor is configured to determine heart rate variability.

12. An apparatus for producing a polarizing magnetic field stimulation, comprising:

a magnet mounted within a tube, wherein the tube comprises at least one non-magnetic conductive metal alloy, wherein the tube is comprised of two or more segments and the two or more segments are electrically isolated from each other, and wherein the tube is mounted within a housing;

a first motor coupled to the magnet;

a first processor mounted within the housing, configured to:

connect to a wearable second processor of a wearable device;

select, when connected to the wearable second processor, a preconfigured motor control protocol to operate the first motor, wherein the preconfigured motor control protocol includes instructions to:

cause the first motor to rotate the magnet transverse to a north-south pole axis within the tube to produce a polarizing magnetic field; and control at least one of motor phase, frequency, amplitude, and duration; and operate the first motor using the preconfigured motor control protocol;

wherein the polarizing magnetic field results in a magnetic stimulation, wherein the magnetic stimulation comprises an element of phase, frequency, amplitude and power of a medical therapy.

13. The apparatus of claim 12, wherein the polarizing magnet field is produced by switching a polarity of a magnetic field of the magnet via rotation of the magnet.

14. The apparatus of claim 12, wherein the non-magnetic conductive metal alloy of the tube is used to produce eddy currents to modify the polarizing magnetic field.

15. The apparatus of claim 12, wherein the two or more segments of the tube are electrically coupled to the first processor and controlled by the preconfigured motor control protocol, wherein each segment is individually coupled to the first processor, and wherein the segments are coupled and decoupled using electrical leads attached to each segment.

16. The apparatus of claim 12, wherein the at least one preconfigured protocol controls at least one of the magnet's rotation frequency and degrees the magnet rotates.

17. The apparatus of claim 12, wherein the magnet is an electromagnet or a permanent magnet.

* * * * *